(12) United States Patent
DeBusk et al.

(10) Patent No.: US 6,581,204 B2
(45) Date of Patent: Jun. 17, 2003

(54) MODULAR TRACKING AND PROFILING SYSTEM

(75) Inventors: Brian C. DeBusk, Clinton, TN (US); Mark W. Shanks, Clinton, TN (US); Michael C. Cofer, Knoxville, TN (US); W. Francis Lukens, Knoxville, TN (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 90 days.

(21) Appl. No.: 09/734,824

(22) Filed: Dec. 12, 2000

(65) Prior Publication Data

US 2001/0016821 A1 Aug. 23, 2001

Related U.S. Application Data

(63) Continuation-in-part of application No. 09/382,710, filed on Aug. 24, 1999.

(51) Int. Cl.$^7$ .................................................. G06F 9/45
(52) U.S. Cl. ........................................... 717/120; 705/2
(58) Field of Search .............................. 717/120; 705/2

(56) References Cited

U.S. PATENT DOCUMENTS

| | | | |
|---|---|---|---|
| 4,737,910 A | 4/1988 | Kimbrow | 705/28 |
| 5,072,383 A | 12/1991 | Brimm et al. | 705/2 |
| 5,295,067 A | 3/1994 | Cho et al. | 705/29 |
| 5,301,320 A | 4/1994 | McAtee et al. | 705/9 |
| 5,307,261 A | 4/1994 | Maki et al. | 705/29 |
| 5,319,543 A | 6/1994 | Wilhelm | 705/3 |

(List continued on next page.)

OTHER PUBLICATIONS

Sethi, Ravi. Programming Languages. New York: Addison Wesley, 1989, pp. 169–173 and 178–185.
Biggerstaff et al. Software Reusability. New York: Addison Wesly. 1989, vol. 2, pp. 269–287.

Primary Examiner—Gregory Morse
Assistant Examiner—John Q. Chavis
(74) Attorney, Agent, or Firm—Fletcher, Yoder & Van Someren

(57) ABSTRACT

An information management system for tracking and analyzing information relating to medical supply usage on a procedural level in a clinical setting includes a general purpose computer system with storage means, processing means, display means, and input means. Information management software installed on the general purpose computer includes node software objects providing a health care information management function. The node software object includes a clinical pathway node software object, a case management node software object, and a resource utilization tracking node software object. The clinical pathway node software object creates clinical pathway module software objects, including resource software objects and container software objects. The resource utilization tracking node software object performs an analysis to determine supply request and actual usage patterns on a procedural level over a given time period for a particular health care provider, by comparing the issued, consumed, returned, and scrapped amounts, and modifying the provider-specific procedural templates to more fully conform to the actual usage patterns based on the analysis.

6 Claims, 35 Drawing Sheets

U.S. PATENT DOCUMENTS

| | | | |
|---|---|---|---|
| 5,321,605 A | 6/1994 | Chapman et al. | 705/29 |
| 5,359,509 A | 10/1994 | Little et al. | 705/2 |
| 5,398,336 A * | 3/1995 | Tantry et al. | 700/9 |
| 5,412,576 A | 5/1995 | Hansen | 705/29 |
| 5,557,514 A | 9/1996 | Seare et al. | 705/2 |
| 5,583,758 A | 12/1996 | McIlroy et al. | 705/2 |
| 5,594,638 A | 1/1997 | Lliff | |
| 5,596,502 A | 1/1997 | Koski et al. | 700/95 |
| 5,610,811 A | 3/1997 | Honda | 705/28 |
| 5,671,362 A | 9/1997 | Cowe et al. | 705/28 |
| 5,682,728 A | 11/1997 | DeBusk et al. | 705/28 |
| 5,696,702 A * | 12/1997 | Skinner et al. | 702/178 |
| 5,721,913 A | 2/1998 | Ackroff et al. | 707/103 |
| 5,724,575 A | 3/1998 | Hoover et al. | 707/10 |
| 5,727,161 A | 3/1998 | Purcell, Jr. | 705/30 |
| 5,732,401 A | 3/1998 | Conway | 705/29 |
| 5,748,907 A | 5/1998 | Crane | 705/2 |
| 5,752,234 A | 5/1998 | Withers | 705/2 |
| 5,771,172 A | 6/1998 | Yamamoto et al. | 705/29 |
| 5,777,877 A | 7/1998 | Beppu et al. | 700/97 |
| 5,799,286 A * | 8/1998 | Morgan et al. | 705/30 |
| 5,826,239 A | 10/1998 | Du et al. | 705/8 |
| 5,835,897 A * | 11/1998 | Dang | 705/1 |
| 5,835,910 A | 11/1998 | Kavanagh et al. | 707/103 |
| 5,842,173 A | 11/1998 | Strum et al. | 705/1 |
| 5,845,254 A | 12/1998 | Lockwood et al. | 705/2 |
| 5,978,771 A * | 11/1999 | Vandiver, III, | 700/99 |
| 5,991,728 A * | 11/1999 | DeBusk et al. | 705/2 |
| 6,003,006 A * | 12/1999 | Colella et al. | 700/237 |
| 6,021,392 A * | 2/2000 | Lester et al. | 705/2 |
| 6,049,776 A * | 4/2000 | Donnelly et al. | 700/100 |
| 6,314,556 B1 * | 11/2001 | DeBusk et al. | 705/2 |
| 6,370,511 B1 * | 4/2002 | Dang | 705/2 |
| 6,381,509 B1 * | 4/2002 | Thiel et al. | 382/282 |

* cited by examiner

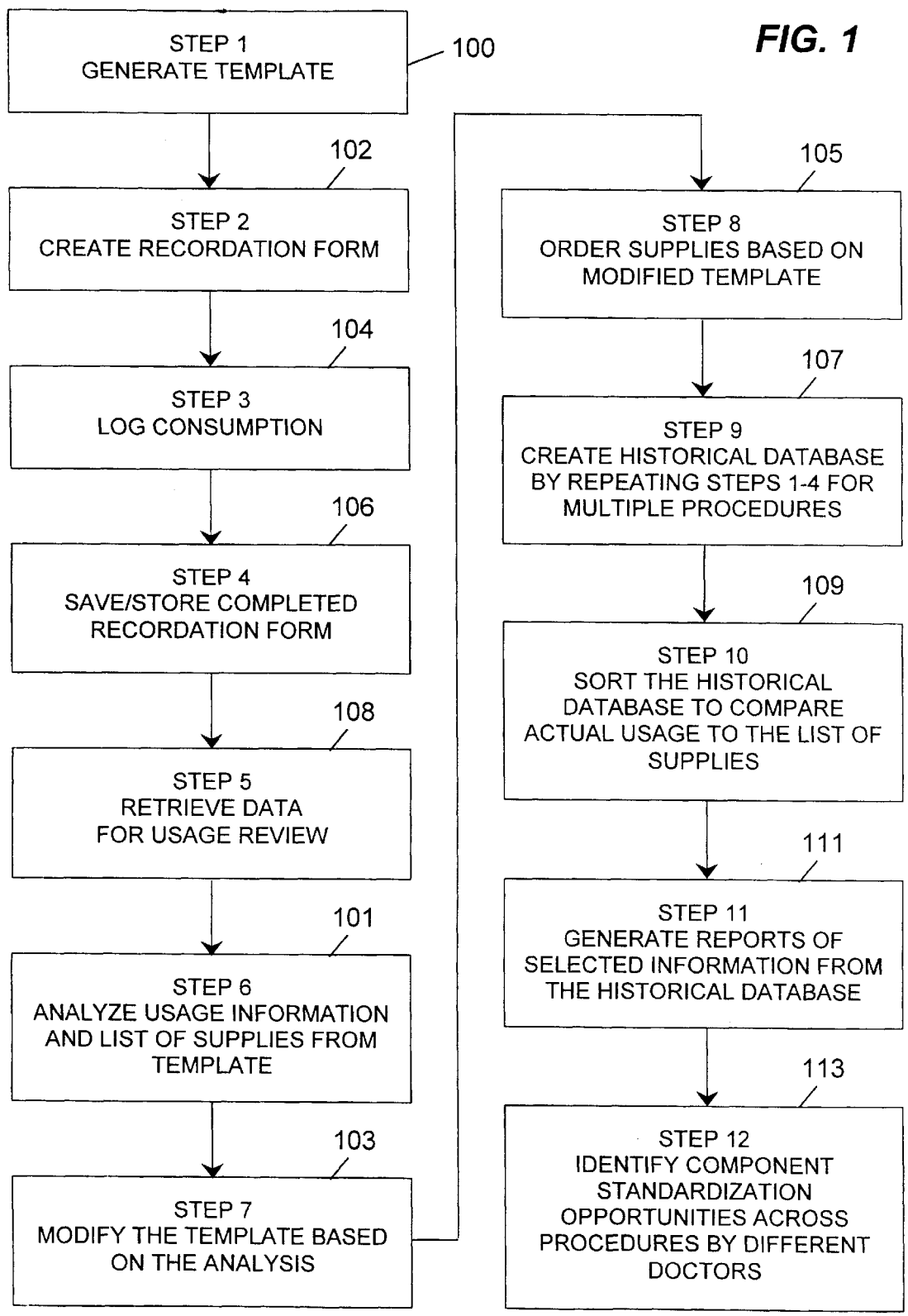

```
                                              ┌─ 110
                            mdl_report.out   /
    90-0542                  MINOR SPINE TRACEPAK                    1.00
       56-11210              BOX,TRACECART 20.5X19X27.5"             1.00
       56-11360R             BASE,RETRACE TRACECRT,30 GAL            1.00
       56-52346        113   LID,RETRACE,TRACECART                   1.00
       91-ANES00010542       ANES CARE EVENT                         1.00
          92-DER0542ANES  \  DER SUPPLY BNDL FOR ANES                1.00
             86-001502  114  KIT, ANES CUST CONCORD HOSPITA          1.00
   ┌─ 91-OPER00010542        OPER CARE EVENT.                        1.00
112    92-DER0542OPER         DER SUPPLY BNDL FOR OPER               1.00
       ┌─ 25-3001    120      STPLR,SKIN,35W,FIX,ST                  1.00
   ┌─ 89-0308                 MINOR SPINE                            1.00
118      89-0308P             PHANTOM PART                           1.00
            5-003             DRSNG,COVADERM 4X8"                    1.00
            5-0504            NDL CTR, FOAM BLOCK/ADH 40CT           1.00
            5-1175            GZE,4X4 16 PLY XR BANDED 10S          20.00
            5-12200           MKR,SKIN STD TIP W/RULER               1.00
            5-12314           LAP,4X18   WSHD,LOOP,XR SP FLD        15.00
            5-14779           PAD,INSTR MAGNETIC 10 X 16             1.00
            5-1583            BAG,STERILIZATION 27X34" 4 MIL         1.00
            5-16991           SPG,NEURO .5X1.5  PATT 10CR XR         1.00
            5-16994           SPG,NEURO .75X.75 PATT 10CR XR         1.00
            5-16995           SPG,NEURO .5X.5   PATT 10CR XR         1.00
            5-17499           DRP, FLAT 43 X 58,HALF-II              6.00
            5-17507           CVR,BK TBL 50 X 90                     1.00
            5-17537           TWL,ABS 15X21,WTE                      4.00
            5-17537           TWL,ABS 15X21,WTE                      2.00
            5-18042           WIPE, INSTRUMENT 4" X 4"               1.00
            5-1828            TRAY,FLAT PLATFORM 15X13.5X1"          1.00
            5-1829            TRAY,LG DEEP 9.72X5.4X2                1.00
            5-18413           GWN,XLG STD NON-REIN LINE-EXT          2.00
            5-1918            LAP,18X18 WSHD,LOOP,XR 5S WLP          5.00
            5-204             EPISEAL,1/2X4" WHITE 3 STR/CRD         2.00
            5-2994            NDL,18GX3-1/2"SPINAL                   1.00
            5-3006            NDL,20GX1-1/2" (ST 305176)             1.00
            5-3011            NDL,22GX1-1/2" (ST 305156)             1.00
            5-3033            SYR,5CC,LL (ST#309603)                 1.00
            5-3050            SYR, IRRIG 50CC BULB                   2.00
            5-3054            SYR,CNTRL,10CC (ST#309695)             1.00
            5-3107            BAG,SUT 6.5X11.3 WT NON-LATEX          1.00
            5-3200            BLD,10,CRBN,R-B,ST                     2.00
            5-3210            BLD,15,CRBN,R-B,ST                     1.00
            5-3244            TBG,SUCT 1/4X12 NC FEMALE/CONN         1.00
            5-3323            TIP CLNR FOR CAUTERY PNCL 2X2          1.00
            5-3998            DRSNG,XEROFORM 1X8 SHERWD              1.00
            5-5262            CVR,MAYO STD 23 X 54                   1.00
            5-5271            DRP,UTILITY 15 X 26,W/TAPE             4.00
            5-6445            TAPE STRIP,2X5" W/DEROYAL LOGO         1.00
            5-6663            CVR,O/H TBL 85 X 76,W/EXT              1.00
   122      5-9159            DRP,SPLIT 76 X 120,W/TAP 12X30         1.00
     \      5-9230            DRP,BAR 62 X 106,W/TAPE & ABC          1.00
        ─ SA89-0308P-1        CAUTERY PENCIL W/HLSTR.                1.00
            5-3214              HNDCTRL PNCL, RCKR BLD STD PLG       1.00
            5-3373              HLSTR ONLY FOR CAUTERY PENCIL        1.00
         SA89-0308P-2         EASYFOLD BTC.                          1.00
            5-17440             CVR,BK TBL 44 X 90                   1.00
         TRLAB-001            LBL:DEROYAL 1-UP TRAY  STER            1.00
   92-DLR0542OPER ┐           DLR SUPPLY BNDL FOR OPER               1.00
   TPAK-LAB       │           LBL:8"BLNK WTE RL"TRCPK CONTE"         1.00
                 116

Page 1
```

FIG. 2

RCL Pick List

| Stamp Patient Imprint Here | Lot Number 198645<br>Serial #: 1<br>Part: 90-0542  Rev#: 3<br>Description: MINOR SPINE TRACEPAK |
|---|---|

| DATE | ROOM NO. | BEGIN TIME | END TIME |
|---|---|---|---|
| NOTES | | | |

| Part Number: | Description: | Issued: | Consumed | Scrap: | Return: |
|---|---|---|---|---|---|
| 92-DER0542ANES | DER SUPPLY BNDL FOR ANES | | | | |
| 86-001502 | KIT, ANES CUST CONCORD HOSPITA---- | 1.00 | | | |
| 92-DER0542OPER | DER SUPPLY BNDL FOR OPER | | | | |
| 89-0308 | MINOR SPINE--------- | 1.00 | | | |
| 25-3001 | STPLR,SKIN,35W,FIX,ST--------- | 1.00 | | | |
| 89-0308 | MINOR SPINE | | | | |
| 89-0308P | PHANTOM PART--------- | | | | |
| 89-0308P | PHANTOM PART | | | | |
| 5-1583 | BAG,STERILIZATION 27X34" 4 MIL------- | 1.00 | | | |
| 5-3107 | BAG,SUT 6.5X11.3 WT NON-LATEX-------- | 1.00 | | | |
| 5-3200 | BLD,10,CRBN,R-B,ST--------- | 2.00 | | | |
| 5-3210 | BLD,15,CRBN,R-B,ST--------- | 1.00 | | | |
| SA89-0308P-1 | CAUTERY PENCIL W/HLSTR.--------- | | | | |
| 5-17507 | CVR,BK TBL 50 X 90--------- | 1.00 | | | |
| 5-5262 | CVR,MAYO STD 23 X 54--------- | 1.00 | | | |
| 5-6663 | CVR,O/H TBL 85 X 76,W/EXT--------- | 1.00 | | | |
| 5-9230 | DRP,BAR 62 X 106,W/TAPE & ABC--------- | 1.00 | | | |
| 5-17499 | DRP,SHT 43 1/2 X 58,HALF-II--------- | 6.00 | | | |
| 5-9159 | DRP,SPLIT 76 X 120,W/TAP 12X30--------- | 1.00 | | | |
| 5-5271 | DRP,UTILITY 15 X 26,W/TAPE--------- | 4.00 | | | |
| 5-003 | DRSNG,COVADERM 4X8"--------- | 1.00 | | | |
| 5-3998 | DRSNG,XEROFORM 1X8 SHERWD--------- | 1.00 | | | |
| SA89-0308P-2 | EASYFOLD BTC.--------- | | | | |
| 5-204 | EPISEAL,1/2X4" WHITE 3 STR/CRD--------- | 2.00 | | | |
| 5-18413 | GWN,XLG STD NON-REIN LINE-EXT------ | 2.00 | | | |
| 5-1175 | GZE,4X4 16 PLY XR BANDED 10S--------- | 20.00 | | | |
| 5-1918 | LAP,18X18 WSHD,LOOP,XR 5S WLP-------- | 5.00 | | | |
| 5-12314 | LAP,4X18 WSHD,LOOP,XR SP FLD-------- | 15.00 | | | |
| 5-12200 | MKR,SKIN STD TIP W/RULER--------- | 1.00 | | | |
| 5-0504 | NDL CTR, FOAM BLOCK/ADH 40CT------ | 1.00 | | | |
| 5-2994 | NDL,18GX3-1/2"SPINAL--------- | 1.00 | | | |
| 5-3006 | NDL,20GX1-1/2" (ST 305176)--------- | 1.00 | | | |
| 5-3011 | NDL,22GX1-1/2" (ST 305156)--------- | 1.00 | | | |
| 5-14779 | PAD,INSTR MAGNETIC 10 X 16--------- | 1.00 | | | |
| 5-16995 | SPG,NEURO .5X.5 PATT 10CR XR--------- | 1.00 | | | |

*FIG. 3a*

| RCL Pick List | | |
|---|---|---|
| 5-16991 | SPG,NEURO .5X1.5 PATT 10CR XR--------- | 1.00 _____ _____ _____ |
| 5-16994 | SPG,NEURO .75X.75 PATT 10CR XR------ | 1.00 _____ _____ _____ |
| 5-3050 | SYR, IRRIG 50CC BULB------------------- | 2.00 _____ _____ _____ |
| 5-3033 | SYR,5CC,LL (ST#309603)----------------- | 1.00 _____ _____ _____ |
| 5-3054 | SYR,CNTRL,10CC (ST#309695)------------ | 1.00 _____ _____ _____ |
| 5-3244 | TBG,SUCT 1/4X12 NC FEMALE/CONN---- | 1.00 _____ _____ _____ |
| 5-3323 | TIP CLNR FOR CAUTERY PNCL 2X2------ | 1.00 _____ _____ _____ |
| 5-1828 | TRAY,FLAT PLATFORM 15X13.5X1"------ | 1.00 _____ _____ _____ |
| 5-1829 | TRAY,LG DEEP 9.72X5.4X2--------------- | 1.00 _____ _____ _____ |
| 5-17537 | TWL,ABS 15X21,WTE---------------------- | 6.00 _____ _____ _____ |
| 5-18042 | WIPE, INSTRUMENT 4" X 4"--------------- | 1.00 _____ _____ _____ |
| SA89-0308P-1 | CAUTERY PENCIL W/HLSTR. | |
| 5-3373 | HLSTR ONLY FOR CAUTERY PENCIL---- | 1.00 _____ _____ _____ |
| 5-3214 | HNDCTRL PNCL, RCKR BLD STD PLG---- | 1.00 _____ _____ _____ |
| SA89-0308P-2 | EASYFOLD BTC. | |
| 5-17440 | CVR,BK TBL 44 X 90--------------------- | 1.00 _____ _____ _____ |
| 92-DLR0542OPER | DLR SUPPLY BNDL FOR OPER | |
| 1608135166 | CORD-------------------------------------- | 1.00 _____ _____ _____ |
| 3642089611 | CVR TABLE BACK  88--------------- | 1.00 _____ _____ _____ |
| 4509001179 | ELECTRODE ADH CONDU 2 SPLIT LG---- | 1.00 _____ _____ _____ |
| 00134302401 | LINER W/LID 2000ML  43024-01------------ | 2.00 _____ _____ _____ |
| 4509008630 | SOL SURG DURA PREP--------------------- | 1.00 _____ _____ _____ |
| 4509006650 | SYS PREP SKIN IOBAN ANTIMICROB---- | 1.00 _____ _____ _____ |

*FIG. 3b*

Print Date: 2/13/97

Powell Regional Medical Center
Resource Consumption Log — 319
Component Volatility Report — 330
Period 11/26/96 to 1/13/97

| ICD9 | Physician | TracePak | Occurrences | | | Components | | | Under-Use | | | Over-Use | | |
|---|---|---|---|---|---|---|---|---|---|---|---|---|---|---|
| | | | Exp | Var | Pct | Sch | Use | Qty Exp | % of Exp. | Avg. Under | Qty | Exp | % of Exp | Avg. Over |

0

BERNARD, GARY
90-0412   C-SECTION TRACEPAK — 328

| | | | 324 | | 326 | 332 | 334 | 338 | 340 | 342 | 344 | 336 | | 346 |
|---|---|---|---|---|---|---|---|---|---|---|---|---|---|---|
| 4917404002 | SYR IRRG BULB W/TIP PROT | | 3 | 2 | 66% | 3 | 1 | 2 | 66% | 1.00 | 0 | 0 | 0% | 0.00 |
| 5-17884 | TOWEL, PAPER, ABSORBENT | | 3 | 2 | 66% | 6 | 2 | 4 | 66% | 2.00 | 0 | 0 | 0% | 0.00 |
| 5-18099 | STRAINER,BASIN | | 3 | 1 | 33% | 3 | 2 | 1 | 33% | 1.00 | 0 | 0 | 0% | 0.00 |
| 5-1873 | BOWL, 16 OZ 500CC | | 3 | 1 | 33% | 3 | 2 | 1 | 33% | 1.00 | 0 | 0 | 0% | 0.00 |
| 5-1892 | CUP,MEDICINE 2 OZ | | 3 | 1 | 33% | 3 | 2 | 1 | 33% | 1.00 | 0 | 0 | 0% | 0.00 |
| 5-1918 | LAP SPONGES, 18 X 18 | | 3 | 2 | 66% | 62 | 60 | 2 | 66% | 1.00 | 0 | 0 | 0% | 0.00 |
| 5-3035 | SYRINGE, 10CC | | 3 | 1 | 33% | 3 | 2 | 1 | 33% | 1.00 | 0 | 0 | 0% | 0.00 |
| 5-3208 | BLADE #20 | | 3 | 1 | 33% | 6 | 4 | 2 | 33% | 2.00 | 0 | 0 | 0% | 0.00 |
| 5352030480 | GLV BIOGEL SURGEONS SZ 8 | | 3 | 2 | 66% | 3 | 1 | 2 | 66% | 1.00 | 0 | 0 | 0% | 0.00 |
| 5-9543 | BOWL, 80 OZ SPONGE BLUE | | 3 | 1 | 33% | 3 | 2 | 1 | 33% | 1.00 | 0 | 0 | 0% | 0.00 |

LEE, CHANG
90-0412   C-SECTION TRACEPAK

| 07076551530 | SUCTION CANNISTER | | 3 | 1 | 33% | 3 | 2 | 1 | 33% | 1.00 | 0 | 0 | 0% | 0.00 |
| 4917033320P | TB CONN OXYG.W/TAPER.CON | | 3 | 1 | 33% | 3 | 2 | 1 | 33% | 1.00 | 0 | 0 | 0% | 0.00 |
| 4917404002 | SYR IRRG BULB W/TIP PROT | | 3 | 1 | 33% | 3 | 2 | 1 | 33% | 1.00 | 0 | 0 | 0% | 0.00 |
| 5-0801 | NEEDLE COUNTER, FOAM 30CT | | 3 | 1 | 33% | 3 | 2 | 1 | 33% | 1.00 | 0 | 0 | 0% | 0.0* |
| 5-10022 | SKIN STAPLER 35W | | 3 | 1 | 33% | 3 | 2 | 1 | 33% | 1.00 | 0 | 0 | 0% | 0.0. |
| 5-1198 | DRESSING, ADAPTIC 3 X 8 | | 3 | 2 | 66% | 3 | 2 | 1 | 33% | 1.00 | 0 | 0 | 0% | 0.00 |
| 5-17874 | CUP,DENTURE 8 OZ | | 3 | 2 | 66% | 6 | 2 | 4 | 66% | 2.00 | 0 | 0 | 0% | 0.00 |
| 5-17884 | TOWEL, PAPER, ABSORBENT | | 3 | 1 | 33% | 6 | 2 | 4 | 66% | 2.00 | 0 | 0 | 0% | 0.00 |
| 5-18220 | BELT, OB | | 3 | 1 | 33% | 3 | 2 | 1 | 33% | 1.00 | 0 | 0 | 0% | 0.00 |
| 5-1873 | BOWL, 16 OZ 500CC | | 3 | 1 | 33% | 3 | 2 | 1 | 33% | 1.00 | 0 | 0 | 0% | 0.00 |
| 5-1892 | CUP,MEDICINE 2 OZ | | 3 | 2 | 66% | 3 | 1 | 2 | 66% | 1.00 | 0 | 0 | 0% | 0.00 |
| 5-1918 | LAP SPONGES, 18 X 18 | | 3 | 3 | 100% | 63 | 60 | 3 | 100% | 1.00 | 0 | 0 | 0% | 0.00 |
| 5-2219 | GLOVES LATEX, SIZE 7 | | 3 | 1 | 33% | 3 | 1 | 1 | 33% | 1.00 | 0 | 0 | 0% | 0.00 |
| 5-3035 | SYRINGE, 10CC | | 3 | 2 | 66% | 3 | 1 | 2 | 66% | 1.00 | 0 | 0 | 0% | 0.00 |
| 5-3107 | BAG, SUTURE | | 3 | 1 | 33% | 3 | 2 | 1 | 33% | 1.00 | 0 | 0 | 0% | 0.00 |

Page: 1

*FIG. 14*

Print Date:2/13/97

Powell Regional Medical Center
Resource Consumption Log — 348
Component Usage Report
Period 11/26/96 to 1/13/97

| ICD9 | Physician | TracePak | Component | Component Description | Vendor | Total Consumption |
|---|---|---|---|---|---|---|
| 0 | BERNARD, GARY | | | | | |
| | 90-0412 | C-SECTION TRACEPAK | | | | |
| | | | 07076565 1530 | SUCTION CANNISTER | | 3.00 |
| | | | 491703320P | TB CONN OXYG.W/TAPER.CONN.84 | | 3.00 |
| | | | 4917404002 | SYR IRRG BULB W/TIP PROT | | 1.00 |
| | | | 50-10775 | C-SECTION PROCEDURE PACK | | 3.00 |
| | | | 5-0801 | NEEDLE COUNTER, FOAM 30CT | | 3.00 |
| | | | 5-10022 | SKIN STAPLER 35W | | 3.00 |
| | | | 5-1198 | DRESSING, ADAPTIC 3 X 8 | | 3.00 |
| | | | 5-1307 | PAD, MATERNITY | | 6.00 |
| | | | 5-1578 | BAG,STERILIZATION 21X20" 3 MIL | | 3.00 |
| | | | 5-1583 | BAG,STERILIZATION 27X34" 4 MIL | | 3.00 |
| | | | 5-16656 | WRP,12 X 12,KIMG REG | | 3.00 |
| | | | 5-17481 | KIT, DURA PREP | | 3.00 |
| | | | 5-17748 | BACK TABLE COVER | | 3.00 |
| | | | 5-17777 | BASIN, PLACENTA | | 3.00 |
| | | | 5-17874 | CUP,DENTURE 8 OZ | | 6.00 |
| | | | 5-17884 | TOWEL, PAPER, ABSORBENT | | 2.00 |
| | | | 5-18099 | STRAINER,BASIN | | 2.00 |
| | | | 5-18198 | CAUTERY PENCIL | | 3.00 |
| | | | 5-18199 | HLSTR ONLY FOR CAUTERY PENCI | | 3.00 |
| | | | 5-18220 | BELT, OB | | 3.00 |
| | | | 5-1828 | TRAY,FLAT PLATFORM 15X13.5X1" | | 3.00 |
| | | | 5-1829 | TRAY, LG DEEP 9.72X5.4X2 | | 3.00 |
| | | | 5-1866 | BASIN,RING 6000CC | | 6.00 |
| | | | 5-18664 | GZE, 6 X 6.75 10TR FLUFTEX | | 1.00 |
| | | | 5-1873 | BOWL, 16 OZ 500CC | | 2.00 |
| | | | 5-1892 | CUP, MEDICINE 2 OZ | | 2.00 |
| | | | 5-1918 | LAP SPONGES, 18 X 18 | | 60.00 |
| | | | 5-2219 | GLOVES LATEX, SIZE 7 | | 3.00 |
| | | | 5-3035 | SYRINGE, 10CC | | 2.00 |
| | | | 5-3051 | SYRINGE, EAR, 2 OZ | | 3.00 |
| | | | 5-3107 | BAG, SUTURE | | 3.00 |
| | | | 5-3208 | BLADE #20 | | 4.00 |
| | | | 5-3238 | TUBING SUCTION 1 1/4 IN X 10FT | | 3.00 |

Page: 1

FIG. 15

Print Date: 2/13/97

Powell Regional Medical Center
Resource Consumption Log 350
Procedure Variance Report
Period 11/26/96 to 1/13/97

| Icd9 Code | Physician | TracePak | Total Procedures | Total Cost | Minimum | Average | Maximum | Standard Dev. |
|---|---|---|---|---|---|---|---|---|
| | | | 352 | 356 | 354 | 356 | 358 | 360 362 |
| 0 | | Totals | 66 | $8,154.05 | $59.26 | $126.94 | $185.75 | $18.09 |
| | BERNARD, GARY 90-0412 | C-SECTION TRACEPAK | 3 | $390.25 | $129.31 | $130.08 | $131.63 | $1.10 |
| | LEE, CHANG 90-0412 | C-SECTION TRACEPAK | 3 | $390.33 | $127.07 | $130.11 | $131.63 | $2.16 |
| | JOSEPH, CELESTINE 90-0412 | C-SECTION TRACEPAK | 9 | $1,093.37 | $59.26 | $125.42 | $131.63 | $16.01 |
| | HEBERT, JOHN 90-0412 | C-SECTION TRACEPAK | 7 | $903.83 | $127.07 | $129.12 | $131.63 | $1.85 |
| | HOLMES, JAY 90-0412 | C-SECTION TRACEPAK | 2 | $261.39 | $129.76 | $130.70 | $131.63 | $0.94 |
| | DOWD, CLINTON 90-0412 | C-SECTION TRACEPAK | 4 | $519.49 | $127.29 | $129.87 | $131.63 | $1.86 |
| | JONES-SINGER, MICHELLE 90-0412 | C-SECTION TRACEPAK | 4 | $520.46 | $129.31 | $130.12 | $131.63 | $0.90 |
| | METZ, JOSEPH 90-0412 | C-SECTION TRACEPAK | 1 | $129.76 | $129.76 | $129.76 | $129.76 | $0.00 |
| | MORENO, EDILBERTO 90-0412 | C-SECTION TRACEPAK | 3 | $386.36 | $127.29 | $128.79 | $129.76 | $1.08 |
| | NEUBECK, JAMES 90-0412 | C-SECTION TRACEPAK | 4 | $520.91 | $129.76 | $130.23 | $131.63 | $0.81 |
| | 90-0414 | D&C TRACEPAK | 1 | $59.26 | $59.26 | $59.26 | $59.26 | $0.00 |
| | PYATT, DAVID 90-0412 | C-SECTION TRACEPAK | 2 | $258.47 | $127.29 | $129.24 | $131.18 | $1.95 |
| | SUBRAMANIAN, MYTHILI 90-0412 | C-SECTION TRACEPAK | 1 | $129.76 | $129.76 | $129.76 | $129.76 | $0.00 |
| | WEST, GEORGE 90-0412 | C-SECTION TRACEPAK | 2 | $258.62 | $129.31 | $129.31 | $129.31 | $0.00 |
| | YOUNG, LARRY 90-0412 | C-SECTION TRACEPAK | 8 | $1,030.97 | $127.29 | $128.87 | $131.63 | $1.43 |
| | AGABIGUM, MEHMET 90-0413 | TONSILECTOMY & ADNOIDECTO | 3 | $232.80 | $67.93 | $73.06 | $92.35 | $7.75 |
| | SHUKAIRY, KHALED 90-0413 | TONSILECTOMY & ADNOIDECTO | 1 | $72.52 | $72.52 | $72.52 | $72.52 | $0.00 |
| | LECEA, GREG | | | | | | | |

*FIG. 16*

Page: 1

MODULAR TRACKING AND PROFILING SYSTEM

This application is a continuation in part of prior pending application Ser. No. 09/382,710 filed Aug. 24, 1999.

FIELD OF THE INVENTION

This invention relates generally to the field of systems for tracking supplies, and particularly to a computer implemented system for tracking and profiling supply usage at the procedural level in the health care field.

BACKGROUND OF THE INVENTION

One important consideration in the provision of health care is the allocation, utilization and consumption of resources such as labor, durable equipment, reusable supplies and disposable supplies. For example, one way for supplies to be obtained by hospitals is for a central supply service to order the individual supplies anticipated to be needed for a given time period. These supplies are maintained in a supply room until needed for a given procedure. Once a procedure is scheduled, a pick list (a list of supplies) is generated. A hospital employee then uses the pick list to withdraw the desired items from inventory and place them in the operating room where the procedure takes place. After the procedure is completed, unused supplies are returned to inventory, a list of used supplies is provided to the billing department, and the used supplies are disposed of or re-sterilized. However, this system is costly and inefficient.

For example, a relatively large inventory of supplies has to be maintained, particularly for standard items such as drapes, sponges, sutures, clamps, etc., which could be used in a large variety of procedures. The inventory of such items has to be large in order to insure that sufficient quantities are on hand for every procedure. Furthermore, the act of picking items for surgery and, later, restocking unused items, is onerous and expensive since relatively highly skilled labor is utilized to insure that the proper items were collected and that the restocked items are placed in the proper location. In particular, the restocking of unused items is a substantial burden on the hospital. Each item pulled from inventory has to be either used and billed for, or restocked and not billed for. If an item is not used during the procedure and is billed for anyway, the billing for that product could be considered fraud on the reimbursing party. Since items are often individually wrapped, the restocking procedure could be very time consuming, particularly where sufficient quantities of items are picked from inventory to cover any situation during surgery. For example, it is not uncommon to withdraw ten clamps from inventory and use only three or four, except in situations where heavy bleeding is encountered, which might necessitate the use of all ten.

What is needed, therefore, is an integrated information system for use in healthcare institutions for managing, optimizing and analyzing the use of resources within that institution.

SUMMARY OF THE INVENTION

The above and other needs are provided by an information management system for tracking and analyzing information relating to medical supply usage on a procedural level in a clinical setting. Included is a general purpose computer system with storage means for storing data corresponding to the information, processing means for processing instructions relating to tracking and analyzing the information, display means for presenting the information in a human perceptible format, and input means for receiving user input relating to tracking and analyzing the information.

Information management software is installed on the general purpose computer. Node software objects each provide a health care information management function. A clinical pathway node software object selectively creates, manages, and maintains user-defined, user-configurable clinical pathway module software objects adapted to function with the clinical pathway node software object, and represents provider-specific procedural templates of the information relating to health care services procedures.

The clinical pathway module software objects include resource software objects that correspond to resources to be used in providing health care services. This includes a list of supplies that is predetermined to be preferred by a particular healthcare provider for use during a given medical procedure. Also included is a recordation form for the given procedure based upon at least one of the provider-specific procedural templates for the given procedure. The recordation form includes at least a partial listing of the supplies predetermined to be preferred by a particular healthcare provider for use during the given procedure, based upon the at least one provider-specific procedural template. The recordation form also includes a scheduled amount of each of the supplies included in the procedural template to be used during the given medical procedure.

The clinical pathway modules software objects also include container software objects for containing software objects having at least one common characteristic.

A case management node software object selectively creates, manages, and maintains a user-defined, user-configurable case management module software object from the clinical pathway module software object. The case management module software object is adapted to function with the case management node software object. The case management module software object represents a selected clinical pathway module software object as modified to reflect a prospective patient specific case, and contains patient specific information. The case management module software object is also adapted to receive additional patient specific information.

A resource utilization tracking node software object selectively creates, manages, and maintains a user-defined, user-configurable model module software object from the case management module software object. The model module software object is adapted to function with the resource utilization tracking node software object. The model module software object represents a case management module software object as modified by at least the patient specific information to reflect a historical patient specific case. This is accomplished by recording on the recordation form actual usage information that reflects actual usage of supplies during the given procedure.

The items recorded on the recordation form include an issued amount of each of the supplies included in the procedural template, where the issued amount is an amount issued for use in the given procedure. A consumed amount of each of the supplies included in the procedural template is also recorded, where the consumed amount is an amount actually consumed during the given procedure. A returned amount of each of the supplies included in the procedural template is recorded, where the returned amount is an amount returned to storage after the given procedure. Also, a scrapped amount of each of the supplies included in the procedural template is recorded, where the scrapped amount is an amount disposed of but not consumed during the given procedure nor returned to storage.

The resource utilization tracking node software object further selectively creates, manages, and maintains a user-defined, user-configurable utilization study module software object from at least one model module software object. The resource utilization tracking node software object is also for analyzing the utilization study module software object to determine supply request and actual usage patterns on a procedural level over a given time period for the particular healthcare provider. This is done by comparing the issued, consumed, returned, and scrapped amounts, and modifying the provider-specific procedural template to more fully conform to the actual usage patterns based on the analyzing.

BRIEF DESCRIPTION OF THE DRAWINGS

The foregoing embodiments of the present invention may be best understood with reference to the following Detailed Description of the Preferred Embodiments and the drawings in which:

FIG. 1 is a block diagram showing the basic process steps of the preferred embodiment, FIG. 2 depicts a print-out of a procedural template/bill of materials, FIGS. 3a and 3b depict a print-out of a recordation form, FIGS. 14–16 are examples of reports generated by the software of the example.

DETAILED DESCRIPTION OF THE PREFERRED EMBODIMENTS

Figure 4:
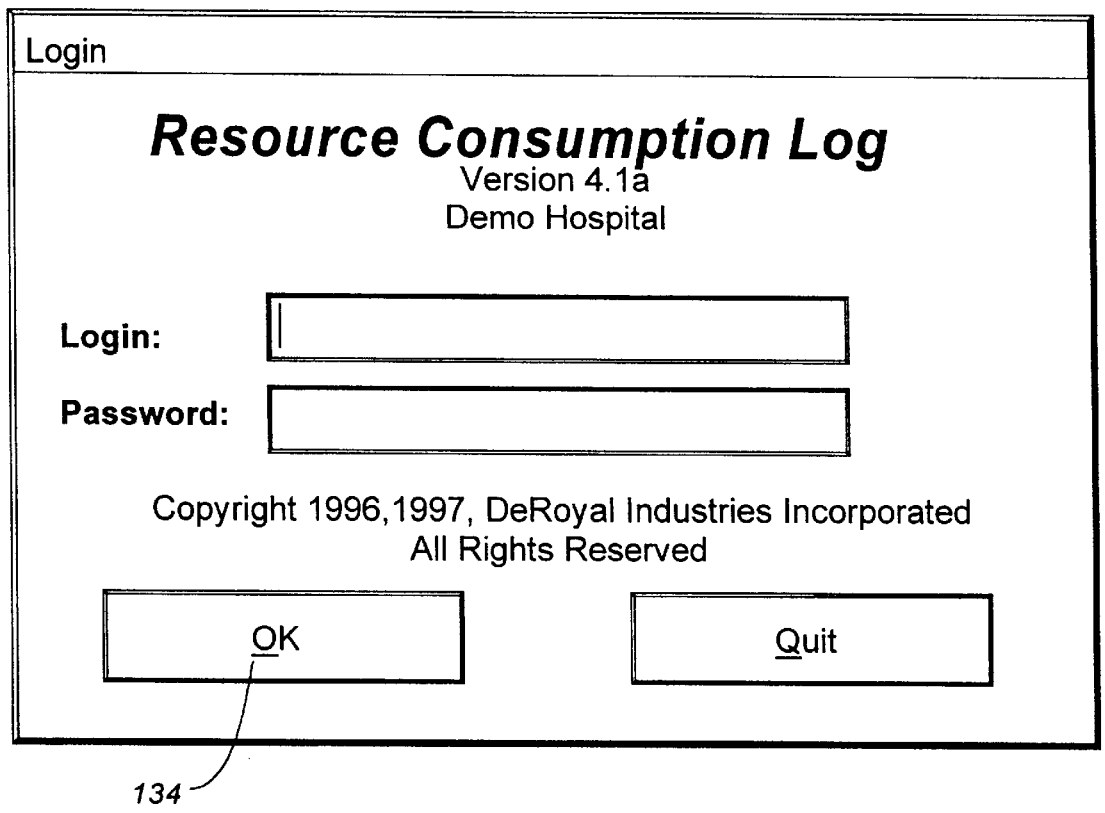
FIG. 4 depicts a screen shot of the login screen of the example.

In the provision of medical services, one way of describing the process by which medical services are provided is through the concept of a clinical pathway. Any given treatment regime or clinical procedure, may be easily described as a related series of care events. Each care event has a some relation to the preceding and/or following care events that is logical and reasonable. For example, take a simple procedure such as suturing a wound. The task of suturing a wound can be described as a series of care events: (1) examination of the wound; (2) cleansing of the wound; (3) anesthesia; (4) suturing of the wound; and (5) dressing the sutured wound. Thus, each of these related care events, make up a clinical pathway for the procedure of suturing a wound. To a person familiar with the medical environment, it will be apparent that each of the care events could be broken down into a more detailed series of sub-care events. Thus, the concept of the clinical pathway is scaleable; that is, any given care event may be made of a series of care events and can therefore be described as a clinical pathway.

The concept of the clinical pathway may also be expanded to more involved procedures. For example, a patient might go to her doctor complaining of particular symptoms. The doctor might then make an examination, or order tests. Based upon the result of the examination and/or tests, the doctor makes a diagnosis and prescribes a treatment regime. Assume that the treatment regime included a surgical procedure to be performed in a hospital, as well as follow-up care. In this case, the clinical pathway might look like:

(1) patient induction (basic administration getting the patient into the doctor's system); (2) examination; (3) testing; (4) diagnosis; (5) prescription of treatment; (6) admission to the hospital; (7) pre-surgical testing; (8) pre-operative preparation; (9) anesthesia; (10) surgery; (11) post-operative recovery; (12) discharge from hospital; (13) follow-up treatment; and (14) final discharge.

Once again, it is obvious that each care event in the given example might be further broken down into smaller incremental care events and, thus, represent a clinical pathway of its own. For example, the surgery could be broken down into each step associated with the surgery from the initial incision until the incision is closed.

In addition to the fact that each care event represents the provision of some type of medical (or administrative) service, each care event also requires the allocation of some type of resources in order to be performed. These resources may be in the form of labor (doctor, nurse, technician, data clerk, etc.), equipment (x-ray machine, respirator, vital signs monitors, etc.), or supplies (sponges, surgical instruments, drapes, x-ray film, sutures, medications, etc.). Thus, for each care event it is possible to identify the allocation of resources necessary for completion of the care event. For example, for the examination step described in the second example, the allocation of resources could be: 15 minutes of doctor's time, use of a specimen collector, use of a specimen container, and the use of a blood collection kit. Likewise, the testing step might include the use of an imaging device (such as an x-ray or MRI machine), 30 minutes of technicians time, use of x-ray film, use of an x-ray developer and associated chemical supplies, and 15 minutes of a radiologist's time to interpret the images.

By describing events in the context of a procedural pathway, a framework is provided which allows for the systematic classification of the steps necessary to treat a particular patient as well as identifying the resource allocation necessary to properly complete the clinical pathway. In the current healthcare environment of cost control and containment, the use of the clinical pathway framework provides an effective and efficient method for characterizing and analyzing the provision of health-care services in the clinical environment.

One important consideration in the provision of healthcare is the allocation, utilization, and consumption of resources such as labor, durable equipment, reusable supplies and disposable supplies. The provision of medical supplies for use in the clinical environment, most particularly in the hospital environment, has evolved over time as the nature of health care provision and, importantly, cost reimbursement, has changed. For example, in the past, the most common way for supplies to be obtained by hospitals was for a central supply service to order the individual supplies anticipated to be needed for a given time period. These supplies would be maintained in a supply room until needed for a given procedure. Once a procedure had been scheduled, a pick list (a list of supplies) would be generated based on the procedure and the doctor performing the procedure. A hospital employee would then use the pick list to withdraw the desired items from inventory and place them in the operating room where the procedure would take place. After the procedure was completed, unused supplies would be returned to inventory, a list of used supplies provided to the billing department, and the used supplies disposed of or re-sterilized. However, this system was costly and inefficient.

For example, a relatively large inventory of supplies had to be maintained, particularly for standard items such as drapes, sponges, sutures, clamps, etc., which could be used in a large variety of procedures. The inventory of such items had to be large in order to insure that sufficient quantities were on hand for every procedure. Furthermore, the act of picking items for surgery and, later, restocking unused items, was onerous and expensive since relatively highly skilled labor was utilized to insure that the proper items were collected and that the restocked items were placed in the proper location. In particular, the restocking of unused items was a substantial burden on the hospital. Due to the then current mode of reimbursement for supply costs, each item pulled from inventory had to be either used (and billed for) or restocked (and not billed for). If an item was not used during the procedure and was billed for anyway, the billing for that product could be considered fraud on the reimbursing party. Since items were often individually wrapped, the restocking procedure could be very time consuming, particularly where sufficient quantities of items were picked from inventory to cover any situation during surgery (i.e., it would not be uncommon to withdraw 10 clamps from inventory and use only 3 or 4, except in situations where heavy bleeding is encountered, which might necessitate the use of all 10).

This situation led to the development of the procedural pack. Initially, suppliers started noting that certain combinations of supplies were used in almost all surgeries. For example, a series of drapes would almost always be used. Thus, a procedural drape pack was developed which included a collection of the most commonly used drapes in numbers commonly used. These drapes were packaged and sterilized as a unit, so that the use of any portion of the unit constituted use of the entire unit. For example, the pack might contain five drapes, but only four might be used during surgery. However, since the package was opened, and sterility was thereby compromised, the entire unit could legitimately be considered used. Although some waste occurred, this system cut out the required re-stocking cost.

Initially, small procedural packs were developed for common events. Incision packs, anesthesia packs, suture kits and a variety of other procedural packs, or supply bundles, were developed. As hospitals grew more used to the concept of procedural packs, the demand for more comprehensive supply bundles increased. The procedural pack ultimately evolved into a large bundle, differentiated by surgical procedure, that included all disposable components for that procedure.

In the era of cost-plus reimbursement, the hospitals had an incentive to use ever growing, comprehensive procedural packs. Use of a large pack, with all possible components present, served to minimize the amount of labor required to pick items from inventory and restock unused item. Additionally, it allowed hospitals to greatly reduce their inventory since such packs could be ordered on an as-needed basis, instead of maintaining a large inventory supplies. However, in order to increase these efficiencies, the packs had to be able to cover any possibility that might reasonably be encountered during the procedure, and often included a large amount of supplies which were not often used in most procedures.

With the advent of cost-containment in the health-care environment, the care providers are required by the reimbursing parties to minimize expense and cost wherever possible. Under the tenets of managed care, if a supply is not used during a procedure, then the reimbursing party is not willing to pay for that supply. This environment leads back toward the concept of having an inventory of supplies which are pulled and then restocked when unused. However, reimbursing parties do realize that some waste in the use of supplies is justified in order to minimize labor expenses concerned with the pulling and restocking of supplies. Thus, the pressure on suppliers led to the development of "custom procedural packs." These custom packs attempt to be comprehensive, but are tailored to the circumstances to attempt to minimize waste. For example, there is a "parts list" or supply list generated by each doctor for each procedure performed by that doctor in a given hospital. Thus, doctors are able to specify the supplies desired, the quantities desired and, if a preference is felt, the brand and type of the desired supply. Thus, if Doctor A uses more lap sponges than Doctor B, their preference cards will differ. Under the cost-plus reimbursement scenario, a procedural pack would have been developed which just had the maximum number of lap sponges used by any doctor. The extra lap sponges in a pack provided to Doctor B would just be wasted. However, under managed care, a custom procedural pack could be developed for Doctor A and Doctor B which allowed for the differing preferences. Once again, however, the more specialized the custom procedural pack, the more inventory will have to be maintained. Since there is the potential for each doctor to have a different custom procedural pack for each different procedure performed by the doctor, there would be no standardization of packs in inventory and, therefore, a number of each custom procedural packs would be required for each doctor.

In the final analysis, a balance must be met between standardization and customization of procedural packs, where standardization allows for the greatest savings in inventory because more standardized packs can be used for more different doctors and procedures, and where customization minimizes the waste developed due to usage differences from doctor to doctor and procedure to procedure. It will be apparent to one skilled in the art that the proper balance of standardization and customization will result in the minimum cost, by minimizing both waste and inventory. Thus, with proper balancing, both the reimbursing party will save money, due to decreased waste, and the care provider will save money, due to inventory control.

Custom procedural packs have been present in the medical supply industry almost since the inception of the procedural pack. As a marketing technique, the pack manufacturers were willing to customize packs to gain a competitive advantage over other manufacturers and gain an entree to new accounts. However, recently, the industry has become more sophisticated in developing custom packs and packs with the cooperation of the customers. Initially, custom procedural packs were slight variations of standard packs or packs already offered by the manufacturer. However, with increasing customization demands and ever changing product offerings, a more sophisticated method of developing custom procedural packs was required.

The procedure for developing the types of custom procedural packs described herein includes a starting point based upon historical usage. For example, say that the hospital already has a standard procedural pack for a laparoscopic gall bladder surgery. The supply list for this standard procedural pack could provide the template for developing the custom procedural packs for that hospital. After first organizing the template supply list into a nested bill of materials, the template is modified by each doctor's preference card to develop a custom nested bill of materials for each doctor who performs that procedure in the hospital. The step of organizing this initial bill of materials for each doctor requires some judgment in order that minor differences in supply usage are minimized (i.e., if one doctor uses two units of a low cost item, and another doctor uses three units of the same item, it is probably cheaper to standardized both bills of materials to three units; conversely, if the item is a high cost item, it is best to differentiate the bills of materials). The result is that a bill of materials for a procedural pack is developed for each doctor for each procedure.

With a bill of materials developed for each procedural pack for each procedure, the various suppliers of the products can then develop supply bundles for each step set out in the clinical pathway. Typically, not all of the supplies are provided by a single supplier or manufacturer, so that multiple supply sources develop supply bundles for inclusion into the procedural pack for a given customer. A container may be shipped to each source of supplies and the supplies provided by that source can be added to the container, thus reducing the time and shipping costs associated with collecting and shipping various components to a single assembly location. In operation, the initial source of the container develops a work order based on the nested bill of materials which each supplier uses to add the appropriate supply bundles to the container. Alternatively, each supplier could ship its supply bundle to a centralized assembly location for assembly of the container and shipment to the ultimate customer. This supply paradigm provides the customer and the suppliers with a framework within which the suppliers can respond very rapidly to an order by the hospital for a custom procedural pack. Thus, even though there exists the possibility that a large number of different packs may be developed for each hospital, the hospital need not maintain a large inventory of such custom procedural packs since the supply process has been streamlined. With proper implementation of the system, a very small number of custom procedural packs may be kept in inventory by the hospital (maybe one week's worth) which will obviously reduce the inventory costs of the hospital. Similarly, since the parts list, or nested bill of materials for each pack has been analyzed, waste is minimized and efficiency is enhanced.

In this supply paradigm, an attempt is made at the time of the development of the nested bill of materials for each custom procedural pack to minimize waste while maximizing standardization to ultimately reduce the overall cost to the care provider. However, this initial analysis is not sufficient to insure that the bill of materials remains optimized. For example, doctors are constantly revising their supply usage based upon new surgical techniques. Similarly, manufacturers are constantly updating their products to incorporate new products and developments. Also, prices are constantly changing in the marketplace.

Upon review of the foregoing, there are several areas where intervention is necessary to insure that the process results in the best balance between waste minimization and standardization, in addition to the ultimate requirement that all of the supplies required during a procedure are actually available when the procedure is conducted. First, the clinical pathway must be developed. Second, bills of materials must be developed in the context of the clinical pathway and balanced to account for doctor preferences, standardization and waste minimization. Finally, usage of materials must be tracked in order to insure that the bills of materials currently in use are optimized to continue to minimize waste while maximizing standardization, as well as providing a basis for documenting resource usage during a procedure in order to allow for proper billing of the procedure to the party responsible for paying for the procedure.

An additional element that must be considered in the clinical pathway is not only the optimization of the bill of resources through utilization review and standardization, is the scheduling of the resources so that the proper resource is in the proper location at the proper time. Prior art methods of scheduling resources have been organized around OR scheduling programs such as the OR scheduling program available from DeRoyal Business Systems, LLC, an affiliate of the assignee hereof. This software is typical of OR scheduling software in that it provides a calendaring function for reserving OR's for use by doctors, and allows for the scheduling of various related items such as durable medical equipment, etc. Also, some OR scheduling packages provide a database function for maintaining doctor "preference cards," which are lists of specific supplies that a given doctor will require during the surgery.

However, such software, usually marketed as a stand-alone package, does not function under the clinical pathway management and is not integrated with resource management. Thus, information is typically unnecessarily entered multiple times, in multiple locations, on multiple information systems. For example, a bill of materials may be generated for a given medical procedure for use by the supply department of a hospital in order to insure that the needed supplies will be available; separately, the doctor preference card from the OR scheduling package will be used to make sure that the supplied materials matches the doctor's preferences; the availability and provision of labor resources will be handled by a different department with a different information system. Usually, these information systems are not integrated and their use results in a myriad of duplication of data entry, along with substantial opportunities for error. Finally, these information systems do not typically provide a basis for calculating medical procedure costs in an efficient manner, so that cost recovery and cost reductions processes must be done on an ad hoc basis.

Returning to the top level of the clinical pathway analysis, the performance of a medical procedure represented by the clinical pathway requires that all of the necessary resources be brought together at the appropriate time and place, which requires that supplies be accounted for and personnel and other resources be scheduled. Once the procedure has been performed, it is important that resource consumption/utilization be recorded for the purposes of cost recovery and utilization review. Finally, it is important that the information be available for analysis in order to allow the process to be analyzed in order to facilitate more efficient resource utilization and to identify economies which may be realized in the clinical pathway.

To date, no hospital information system has provided an integrated package for OR scheduling/preference card management, resource consumption logging/storage and resource utilization analysis/bill of resource standardization. Furthermore, even the most comprehensive hospital information systems are written in monolithic style which either represents a 100% custom application written specifically for the customer, or an off-the-shelf application that does not meet all of the needs of the customer. Neither situation fits the current health-care environment of reform, cost-cutting and change. Monolithic software packages require the review and revision of large blocks of source code, and a small change at one point may well affect the functioning of other portions of the code. In large applications, hundreds of thousands, if not millions, of lines of code must be reviewed for every change, even if relatively minor. This state of affairs often results in health-care institutions refusing to adopt cost-saving and efficiency enhancing measures, since the potential benefits are often outweighed by the cost and problems which would be involved in adapting their current information systems to the better processes. Also, since different institutions are different sizes, serve different populations, use different doctors, have different areas of core competency, etc., the one-size-fits-all approach to off-the-shelf information systems often results in some institutions adopting procedures which, while they may work well in some environments, are not the most efficient for that institution just to enable the use of a given information system. However, such a system is in actuality backwards, since the institution should be able to determine the most efficient way to operate and then have an information system which is adaptable, at no great expense, to the needs of the institution.

Typically, the use of a custom procedural pack results in a variety of benefits to the hospital such as ease of ordering, ease of cost accounting, ease of use for doctors and other care providers, etc. However, it was often difficult to track the efficiency of the usage of the supplies provided in such trays to determine if all of the necessary products were present in the tray, if there were supplies in the tray that were not routinely used, or if there were sources of supplies for the tray which could provide a lower cost than the manufacturer of the tray.

Furthermore, hospitals typically have a multitude of information systems relating to the usage and ordering of supplies for procedures. For example, the hospital billing system is often used to track costs to be billed to patients for the purposes of generating billing statements. Another system might be used to submit information to insurers and other payment providers to submit claims for payment for particular services and costs. A further system might be used to control the hospital supply inventory. Finally, an additional system might be used to keep track of doctors procedural supply preferences and the contents of custom procedural packs.

With such a plurality of information systems, often a hospital or clinic has trouble tracking exactly what supplies are being provided for a given procedure, what supplies are actually used in a given procedure, and trending historical usage for the purposes of projecting future usage as well as fine tuning the contents of custom procedural packs.

One system which has been used in the past, either as a computer maintained list, or on paper, has been a resource consumption log. This system basically provides a list of supplies provided during a given procedure and, either as they are used, or after the procedure, a simple tally is made to determine if the quantity of usage of the listed supplies. These types of supply usage counts typically are nothing more than lists generated from the packing list of the custom procedural pack and the supply preference list provided by the doctors and care givers associated with each procedure. Typically, this type of tally is used primarily for the purposes of cost recovery and inventory replenishment. However, the lists associated with such previous logs are sometimes unwieldy and difficult to use. Furthermore, these systems require entry of the data into multiple systems and, typically, the data is not used for analysis or trending.

In the current health care environment, there is increased pressure to track and minimize costs associated with the delivery of health care. One of the major areas of cost in any healthcare facility is the supplies used during medical procedures. Often, hospitals and clinics utilize procedural packs which are designed to have all of the supplies that a surgeon or other caregiver might need to use during the procedure. However, when these procedural packs are designed to be comprehensive, there can be considerable waste of supplies simply because they are not used during a particular procedure. Conversely, sometimes a supply is used frequently is not included in a procedural pack, thus requiring that hospital or clinic supplied labor be used to keep an inventory of such supplies and make sure that such supplies are delivered to the care site for the procedure. However, prior art supply tracking methods and systems do not provide an integrated package for the tracking of anticipated usage and actual usage.

Information systems in the health-care environment have used the paradigm of the patient record in managing information. That is, the primary identifying feature was the patient for information which was stored about resource allocation, supply utilization, resource scheduling, supply ordering, cost accounting, etc. Obviously, this paradigm has worked for some time owing in large part to the fact that cost reimbursement is done on a per patient basis, and all cost recovery and accounting needed to be allocable to an individual patient.

However, as health-care reform debate has forced healthcare providers to focus on streamlining the provision of medical services, the focus has turned from patient-centered information systems to procedure-based management and accounting. Basing an information system around the procedural pathway, as opposed to just tying services, supplies and other resources used to the patient, with no real relation to the pathway, provides an inherent ability to use the information more efficiently and to allow for greater cost accountability in the provision of medical services.

To illustrate the efficiency of the procedural pathway, it is best to analyze generally a hospital stay for a given patient. Initially, the patient is admitted, has some blood work done, is assigned a room, is possibly subjected to some diagnostic screenings, possibly have a procedure done, spends a period of time recovering from the procedure, and is discharged. Also, the clinical pathway may extend beyond the hospital stay and include follow-up care such as periodic check-ups and/or rehabilitation. Each step along the procedural pathway can be broken down into increasingly fine detail as series of more and more detailed sub-procedures. For example, the surgical procedure can be further broken down into surgical prep, anesthesia, the surgical procedure, closing, and post-op anesthesia recovery. Obviously, each of these sub-procedures could be further broken down into specific tasks to be performed at each stage.

As can be seen from the procedural pathway model, each stage of the procedural pathway is going to require the utilization of resources. These resources may be labor resources, consumable supply items, durable equipment, reusable supply items, particular rooms (i.e. patient rooms, Operating Rooms (OR's), recovery rooms, etc.) or services. For example, the blood work requires a technician to draw the blood, the disposable equipment for drawing blood, a labor resource to deliver the blood to the laboratory, the consumable and reusable supplies for handling and testing the blood, durable medical equipment for testing the blood, labor resources for testing the blood and generating the report, and a labor resource for providing the report to the patient's chart. As can be seen, each resource can be analyzed and tied to a particular care event along the procedural pathway.

Each procedural pathway is going to have some unique characteristics which vary based upon the reason the patient is in the health-care facility (the type of procedure), the doctor performing the procedure, and the characteristics of the patient. Obviously, the clinical pathway is different for someone having heart-bypass surgery than it is for someone having out-patient orthopedic surgery. Likewise, preferences vary from one doctor to another in performing the same surgery; i.e. one doctor may prefer the feel of one brand of scalpel while another doctor may prefer another. Finally, the patient often dictates variation within a given procedure; i.e. one patient may have certain physical characteristics that require using certain supplies and equipment, and another patient may require different supplies and equipment.

The present invention provides an information system for use in the health-care environment that utilizes the procedural pathway paradigm for the input of data, the organization of data, the retrieval of data and the analysis of the data. In addition to storing unique data for each clinical pathway (historical data), the present invention also provides for the development of clinical pathways for certain medical procedures which have been analyzed and standard pathways developed. These clinical pathways, which are created from modular software objects configured by the user of the software, associate the anticipated resource allocation to a given procedure and allow for the anticipation of resource consumption for each upcoming standard procedure. For example, if a clinical pathway has been developed for a hip replacement surgery, the clinical pathway for a given patient coming in for hip surgery is easily developed from the template. The information system user merely needs to enter the identifying information about the patient and the surgeon performing the procedure, and the standard template generates a clinical pathway showing the resources that should be required for that patient. At a further level of detail, departure points from the standard template can be identified and the alternate resource allocation for the departure points may also be provided in the information system. For example, this feature may be described as a conditional bundle. For example, in the hip replacement surgery described above, variations in resource requirements may vary from doctor to doctor because of differing techniques, requirements, and subjective preferences. Thus, the standard template for a hip replacement surgery may be substantially the same for two different doctors, but vary on a few items. The conditional bundles can be used to account for the departure from the standard template for each doctor and, by entering the doctor performing the procedure, the information system can automatically associate the appropriate conditional bundle with the standard template to form the clinical pathway for a given patient.

In terms of resource management, there are two basic types of resources which are needed to perform a medical procedure at a given location: (1) those resources which are brought in from outside the location for the procedure, and (2) those resources which are maintained by the location and which must be scheduled for a given procedure. For the purposes of this application, although doctors are not usually employed by the hospital, we will assume that they are resources associated with the location, since they are typically driving the scheduling of a procedure at a location. The management of outside and inside resources requires the consideration of two different sets of problems. Typically, the outside resources primarily include the supplies which must be ordered from outside vendors, be delivered to the location, and be provided at the appropriate time and place for the performance of the procedure. The inside resources include the labor resources, equipment owned and maintained by the location, and facilities at the location such as OR's, radiology, laboratories, etc.

In managing the outside resources there are two competing interests: (1) the desire to have sufficient quantities of everything readily available, which necessitates a large inventory of supplies along with skilled personnel to maintain the inventory and deliver it for performance of the procedure, and (2) the desire to minimize inventory, which minimizes inventory carrying costs, the risk that inventory will expire before use, tied-up capital, and the skilled labor necessary to maintain the inventory and pull it for each procedure.

In managing inside resources the goal is to maximize the utilization of each available resource while carrying only the minimum amount of required resources to get the job done. Management of these resources necessitates that efficient resource allocation tools be used so that the location is not carrying costs associated with labor, equipment and facilities which are not being fully used, while insuring that all of the procedures can be performed in a timely fashion. For example, idle employees, equipment, OR's, etc. all carry a substantial cost. However, overworked employees, overused equipment and overbooked facilities reduce the efficiency and efficacy of the performance of the procedures and result in additional costs. Thus, precise scheduling and resource utilization management software is necessary to allow for the maximum productivity from resources, while minimizing inefficiency caused by overbooked resources and overworked employees. Additionally, software that provides detailed analysis of historical resource utilization allows for the prediction of when new labor and other resources will be needed, and provides for the most effective way of acquiring those resources, often saving money as opposed to the last minute recognition and rush acquisition of such resources.

DESCRIPTION OF THE PREFERRED EMBODIMENT

The preferred embodiment of the information management system consists of a series of software objects implemented using Microsoft ActiveX controls which may be configured and linked by a user to build a custom-configured health-care information management system. Preferably, the information system is implemented on a Windows NT or Windows 95 based personal computer, which may or may not be networked. In order to maintain a database of information related to this information system, a database program such as Microsoft SQL/Server or Microsoft Access is used in the background. The information system of the preferred embodiment generates data and communicates through an interface compatible with the background database program. Preferably, the software objects described herein are coded in Visual C++ or Visual Basic, and adhere to the framework of ActiveX or OLE controls so as to maintain the ability to be implemented as compatible software objects in a component-based software architecture.

In general, the software provides a number of "nodes," each of which corresponds to a particular function of the information system. For example, if the system has functions for developing and maintaining software based clinical pathways, maintaining and logging resource consumption on a case by case basis, and studying resource consumption for logged cases, each of these functions represents one node. Each of these nodes uses the feature of ActiveX controls to allow objects created in one node to provide necessary information or form the basis for a new object in another node. The interaction of objects from one node to another will be described more fully hereinafter.

Figure 33:
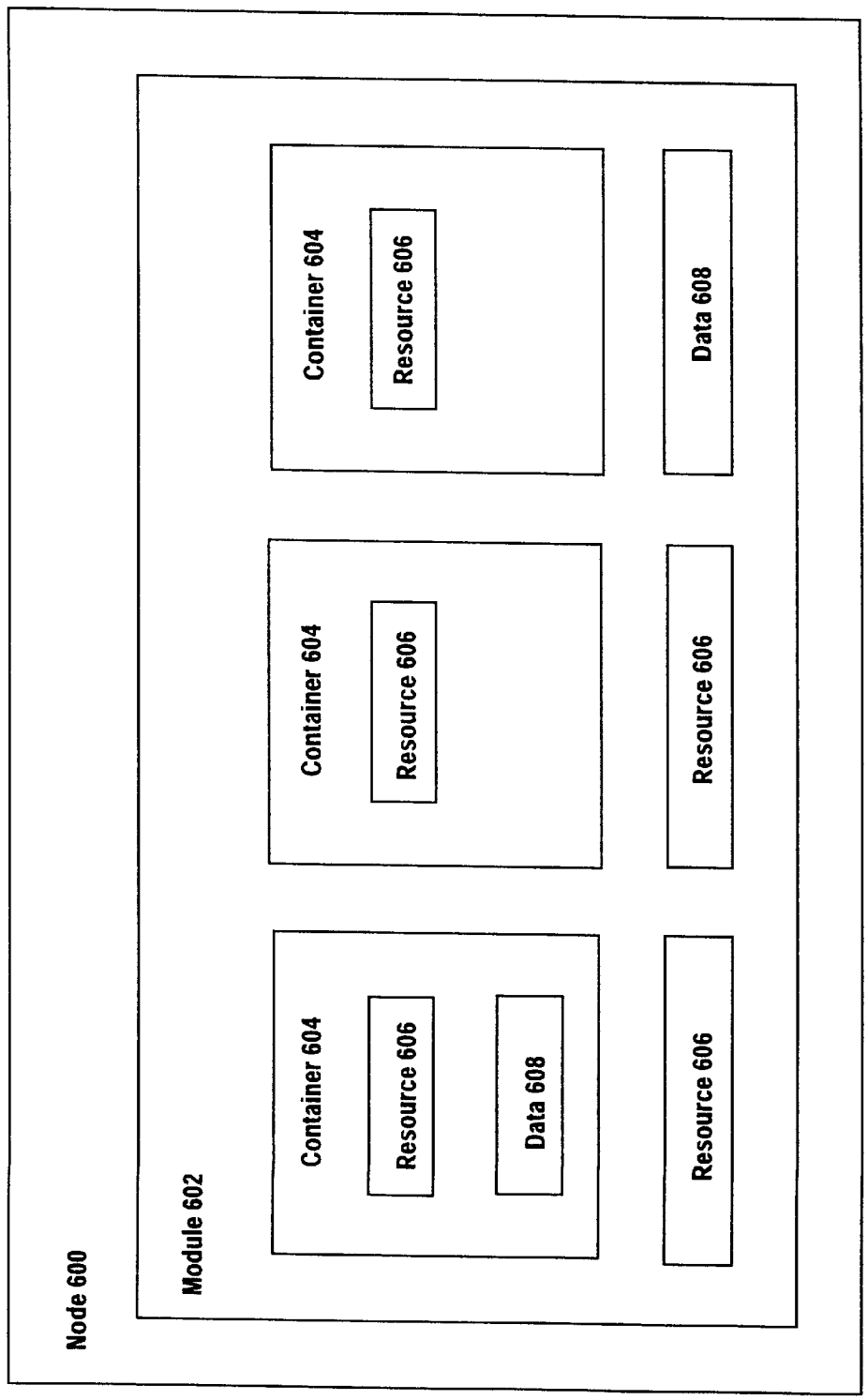
FIG. 33 is a block diagram showing the generic form of the present invention.

Referring now to FIG. 33, each node 600, as described, provides for a particular information management function in the present invention. Also, each node 600 represents a software object which will allow the user to perform certain functions and tasks relative to the information system function provided by the node 600. In general, the function of each node is to allow the user to generate specific templates, or software object modules 606 which organize additional software objects into custom configurations representative of the information to be managed. Under each node 600, the user has access to further software objects, or by copying from previously generated templates, by creating the objects or from an object library, in order to access the functionality of the node 600. The software objects available to the user are preferably of three specific types: (1) container objects 604, (2) resource objects 606, and (3) data objects 608. Each of these objects represent ActiveX software objects which function as miniature software programs to perform a specific function. Container objects 604 function as receptacles of other objects and act to organize the other objects in accordance with the user's specifications. Additionally, container objects 604 are customized by the input of data from the user based upon what the container object 604 is designed to hold, the specific use to which the container object is subjected by the user, and other usage specific data which the user provides.

Resource objects 606 are software objects which represent resources to be utilized in the provision of the health-care. Resource objects 606 typically represent supplies, or kits of supplies, equipment, personnel, pharmaceuticals, or any other resource which will be utilized during the provision of health-care. Each resource object 606 is populated with data relevant to that object and communicates that information as required.

Data objects 608 are software objects that are used by the user to collect specific information for use by the template or the information system. For example, it may be necessary to gather certain procedure-specific information at some point in a clinical pathway, and a data object 608 may be inserted at that point in a module 602 to collect such data and make it available to the appropriate software objects.

Figure 34:
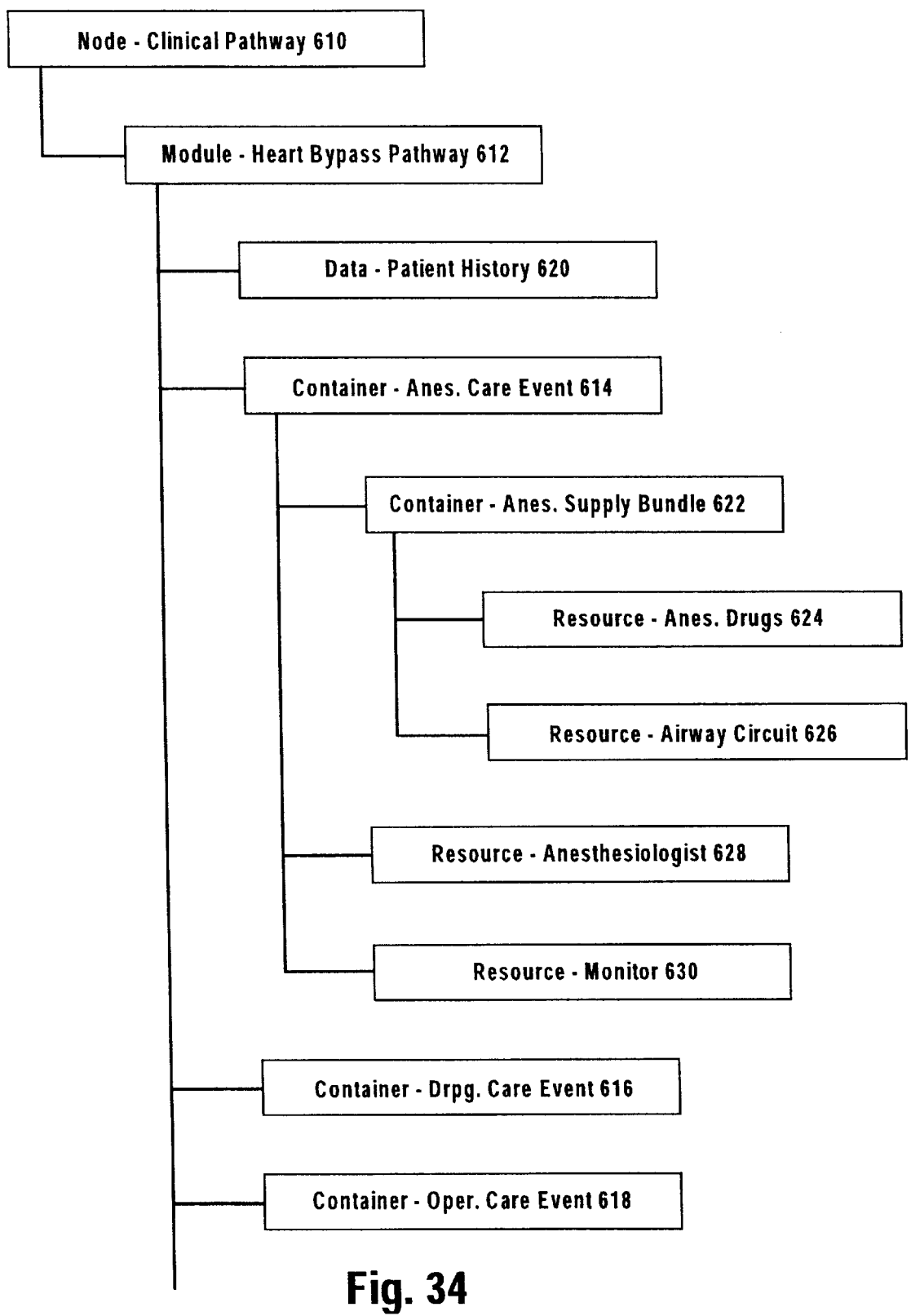
FIG. 34 is a tree diagram showing the organization of a preferred form of the present invention.

Use of the software objects is best understood by a general reference to one function of the information system. Referring now to FIG. 34, the first node 610 of the software represents the function of generation, modification, and maintenance of software templates for clinical pathways using the objects previously described. This node 610 allows the user to create software modules 612, made up of user selected objects, which represent in software a health-care procedure or clinical pathway. In general, as described previously, the clinical pathway is broken down into a series of related care events, representing discrete sub-procedures along the clinical pathway. Using the functionality provided by the clinical pathway node 610, the user is able to develop a new module 612 by making the appropriate menu selection. The user is prompted to input information relevant to the clinical pathway generally, such as the name of the clinical pathway, any hospital or other codes used to identify the type of procedure, doctors who perform that type of procedure, etc.

Once the module 612 is defined and created, the user breaks the procedure down into a series of care events. For example, if the procedure is a heart bypass operation, various care events can be identified such as (1) anesthesia care event, (2) draping care event, and (3) the operative care event. Each of these care events are implemented in the clinical pathway module 612 by the selection or creation of care event container objects corresponding to each care event 614, 616, and 618. These objects require the input of information relevant to the care event and function as containers for additional container, resource, or data care events.

Once the care event containers 614, 616, and 618 have been created in the module 612, the user fills out each of the associated care events for the module. For example, a patient history data object 620 might be associated with the module 612 which prompts the user to obtain patient-specific data when the clinical pathway is used relative to a particular patient. Resources are then associated with each care event.

For example, the Anesthesia Care Event container 614 may contain an anesthesia supply bundle container 622, which in turn can contain resources such as anesthesia drugs 624 and an airway circuit 626. Other resources, provided by a resource object, such as an anesthesiologist 628 and patient monitor 630, are also associated with the anesthesia care event 614. In the example, the anesthesia drugs resource 624 represents a pharmaceutical resource object, which contains certain information relevant to the specific drugs to be delivered, while the airway resource 626 represents specific supplies to be used in the anesthesia care event 614; these two items, because they will be used together, are combined in a supply bundle container 622 which may be reused for other procedures which include an anesthesia care event. The anesthesiologist resource 628 represents a personnel resource object, and contains information concerning the anesthesiologist including identification, time to be allotted for the procedure, and scheduling information. The patient monitor resource object 630 represents an equipment resource, which contains information about its availability and utilization.

This process is repeated until each of the remaining care events 616 and 618 for the clinical pathway is complete. The user of the information system then has a software module 612 configured for the heart bypass clinical pathway which consists of container, resource and data objects. Each of the software objects encapsulates information particular to that object and communicates that information via a standard interface to other software objects as such information is required.

For example, after constructing a particular clinical pathway module, the user might desire to schedule a procedure for a particular patient using the clinical pathway. By utilizing a node designed to manage information for individual cases, the user selects the appropriate clinical pathway module which transfers the data from the clinical pathway module for that procedure into a case module. The case module then contains all of the information from the objects from the selected clinical pathway module and provides a ready listing of resources to be utilized in performing the procedure. With this information, schedules of supplies, equipment, etc. are generated in order to facilitate the performance of the procedure.

Additionally, as is described more fully hereinafter, by creating a case module, the user has available the case node functionality which allows for the tracking of resource utilization in performing the procedure, creating a consumption record for use in analyzing resource utilization, generating cost information for cost recovery, and other case node specific functions. Also, to the extent that objects created in the clinical pathway have utility for other clinical pathways, the created objects may be reused to develop additional clinical pathways.

As described in greater detail below, the various types of objects are predefined in the overall software system. Container objects are available to represent care events, supply bundles, and conditional supply bundles. Each type of container may be configured by the user to reflect the particulars of the clinical pathway to be represented. Care event containers are configured with specific information for each care event in the clinical pathway and contain information relevant to that care event. Supply bundles are provisioned with supply resource objects and have information specific to that supply bundle contained therein. Conditional supply bundles are provisioned with supplies and a condition which will determine if that conditional supply bundle will be used. For example, a conditional supply bundle developed for a particular surgeon has supplies used only by that surgeon provided therein. If the condition is met when a case is scheduled, such as the particular surgeon is assigned to the case, that conditional bundle is automatically added to the list of objects associated with that case.

Similarly, various types of resource objects are provided as standard templates for configuration by the user. Examples of such types of resource objects are supplies, kits (which are pre-packaged groups of supplies), equipment, personnel, and pharmaceuticals. When configuring resource objects for a clinical pathway, the user selects the appropriate supply type for the resource to be represented, and inputs the prompted information. For example, the user might be able to look up a database of listed supplies and select a particular supply for inclusion in the clinical pathway. Alternatively, the user could create a new supply from scratch by inputting prompted information to create a new supply resource object. The type of information varies from resource type to resource type, but a standard template is provided for each resource type to prompt the user to input the appropriate information for each resource to be added.

Additionally, while the user has the option to create various container, resource, and data objects from scratch for use in the information system, the user, to the extent appropriate, would be able to reuse previously created objects. For example, the user might create a library of standard pre-configured objects which are frequently re-used in various clinical pathways. Thus, when a new pathway is created, these library objects may be selected for inclusion in the new pathway. Likewise, information concerning a variety of resources may be maintained in various database systems maintained by a health-care institutions. The supply department may maintain a database of available supplies, or dealers may provide databases of available supplies, by providing standard database program interfaces for these sources of information, data from these sources may be automatically read into the present system in order to configure resource software objects for use therein.

As described, the use of software objects to represent events, bundles, resources and data objects in a health-care information management system allows the user to readily create software modules which represent specific health-care procedures, which are much more functional than with traditional health-care database systems. Furthermore, the module object approach to the system makes it more readily customizable for particular installations. For example, if the standard configuration of any software object is not readily adapted for a particular installation, a programmer is not required to modify a monolithic source code listing to implement the new configuration. For customization, the programmer preferably rewrites the code only for a particular object. As long as the programmer retains the standardized data interface for the object, there is no need for any change in configuration in the remaining source code for the system.

Additionally, the use of the software object framework allows for the ready implementation of new functionality, without requiring the rewrite of the majority of the code for the system. For example, if a new functionality is required, a new functional node may be added which utilizes, to the extent possible, already existing software objects.

The preferred embodiment of the present invention adds such new functionality by introducing a resource utilization tracking node software object to the above-described software to provide for analyzing and tracking information relating to medical supply usage on a procedural level. Most of the resource utilization information for any given procedure is available in the clinical pathway module for that procedure. Thus, to create the resource utilization tracking node, the programmer creates a software object that queries existing software objects for information relevant to resource utilization, and that analyzes that information as described below to determine supply request and actual usage patterns on a procedural level over a given time period for a particular health care provider. In implementing such a node, individual procedural pathways may be copied from a clinical pathway constructed as described above with reference to FIG. 34.

Referring now to FIG. 1, there is shown a block diagram representing the basic method of the present invention. In the most basic embodiment of the present invention, the first step, shown at 100, represents the creation of a template for a given procedure. This template includes at least a partial listing of resources required for a given medical procedure and is organized based on a procedural or clinical pathway. Once the template is created and a procedure corresponding to the procedure of the template is scheduled, a recordation form is created (Step 2, 102) which represents a list of all resources provided to the care site. Either as the procedure is performed, or soon thereafter, actual consumption of resources is entered onto the recordation form (Step 3, 104). Recordation of actual consumption will include the entry of resources consumed during the procedure, whether such resources were included in the template or not. Additionally, the failure to consume scheduled resources during the procedure is logged on the recordation form. In fact, in the preferred embodiment, supply usage is logged by exception; that is, the recordation form shows the scheduled usage and, unless a deviation from the scheduled usage occurs, no entry is made, it is assumed that actual usage conformed to scheduled usage. The recordation form may be a printed item generated by the manufacturer, distributor or user, or it may reside on a computer.

The template and the recordation form are both saved (Step 4, 106) in a retrievable manner. Finally, at a desired time, the template and/or recordation form is retrieved (Step 5, 108) for use resource utilization analysis.

The simplest form of resource utilization analysis consists of reviewing the recordation form to generate a list of supplies used during a procedure for the purpose of billing the recipient of the healthcare services. Other forms of analysis could include a comparison of the recordation form to the template to determine how actual usage during the procedure compared to the anticipated usage as set out in the template (step 6, 101). Such analysis allows for the refinement of the template (step 7, 103) in order to minimize the purchase of anticipated supplies, or scheduling of resources which are not actually used during the procedure. More detailed analysis of resource consumption over time might be used in order to identify similarities between bills of materials for different procedures, or for multiple doctors performing the same procedure. By identifying such similarities, the bills of materials could be standardized, thus simplifying and reducing the cost of ordering (step 8, 105), stocking, and inventory maintenance.

In the preferred embodiment of the present invention, the templates and completed recordation forms are stored in a computer maintained database (step 9, 107). This database may be specially developed for this purpose, or may be a commercially available database program such as Access, by Microsoft or SQL/Server. Preferably, the information is saved such that it may be sorted in any number of ways. For example, the information could be sorted by procedures originating from a given template; thus for all procedures performed originating from that template, supply usage and deviation from the template could be tracked (step 10, 109) (also, this sort could limit in time the number of procedures tracked). Furthermore, using the report generation function of the database software, usage summaries could be generated (step 11, 111). Alternately, the information could be sorted by physician, thus allowing the usage information of a particular physician to be reviewed over time. This information could be compared to the template, or to other physicians, to determine if possibilities exist to standardize physician preference lists to minimize inventory and labor costs associated with maintaining a large number of physician requested items which deviate from the template (step 12, 113).

It should be apparent to one skilled in the art that a wide variety of database sorts, reports, comparisons, summaries, etc. are easily generated from the information available in the template and the resource consumption. Also, the information so saved can be used in a variety of ways such as cost accounting (step 13, 115), supply standardization, inventory control and reduction, supply requirement projections, etc. Thus, the foregoing description is for the purpose of illustration and not limitation.

Referring now to FIG. 2, there is shown a nested bill of materials 110, on a procedural level, which might form the basis of a template. The first step in implementing the method of the present invention, is to develop a template of all the materials expected to be used in a given medical procedure. Such a bill of materials 110, may be the starting point for developing a template for a particular procedure.

The nested bill of materials 110 has several important features which make it useful for a starting point for a template (although the invention is not limited to a procedural pathway/nested bill of materials as a template starting point). As described above, utilizing the procedural pathway principle to organize a medical procedure as a series of related sub-procedures, provides a nested structure for describing the medical procedure. Similarly, for each sub-procedure in the procedural pathway, a supply bundle may be designated which includes a list of all the supplies for that step in the procedural pathway. For example, on the nested bill of materials 110, part no. 91-OPER0542 (112), refers to an Operative Care Event 113. Upon closer examination, it is seen that the bill of materials also lists at the next level two part numbers (92-DER0542OPER (114) and 92-DLR0542OPER) (116) which correspond to supply bundles for the Operative Care Event 113; the first part number 114 refers to a supply bundle prepared by DeRoyal Industries and the second part number 116 refers to a supply bundle provided by a third party dealer. Moving to the next level of detail, the parts for the DeRoyal™ bundle 92-DER9542OPER are listed; part no. 25-3001 (118) represents a skin staples while part number 89-0308 (120) represents a minor spine surgery kit or tray. At the next level of detail, the components of the minor spine kit are listed; it should be noted that the components of the kit or tray may also be bundles of supplies as is seen with reference to part no. SA89-0308P-1 (which is a cautery pencil with subcomponents 5-3214 and 5-3373). The nested bill of materials 110 is recursive, i.e. each level may contain a part which is in turn made up of individual parts. However, ultimately, individual parts are listed at the level of greatest detail.

In the case of FIG. 2, the nested bill of materials corresponds to a sample bill of materials from a unitized supply delivery system sold by DeRoyal Industries, Inc. under the trademark and service mark TracePak™. The DeRoyal TracePak™ system is a system whereby hospitals, with the assistance of DeRoyal, dealers, and the distributor, build unitized supply delivery bundles by sourcing the components from the most cost effective source (i.e. manufacturer, distributor or end-user). In the TracePak™ system, a computerized bill of materials is created representing all of the components of a particular procedure as included in the TracePak™ system for the customer (the printout of FIG. 2 is a paper version of the computerized bill of materials).

When a procedure is scheduled at a customer's healthcare facility, an order for the corresponding unitized container is transmitted electronically to DeRoyal which assembles sterile supply bundles, places them in the container and then ships it to the distributor for addition of its supply bundles, which then ships it to the user. Alternatively, all supply bundles from all of the suppliers may be shipped to a centralized assembly facility where the container may be filled with the required supply bundles and shipped to the customer. In the case of the preferred embodiment of the present invention, the nested bill of materials is used as the procedural template; however, any list of resources to be used in the procedure could be a starting point for the procedural template. The reason that the nested bill of materials is used in the preferred embodiment is that for users of the TracePak™ system, these bills of materials are stored digitally and may be readily imported into the computer implemented version of the preferred embodiment.

At the time the TracePak is assembled, a work order is generated which corresponds to a list of all the supplies provided in a given TracePak. To the extent that a given supply is out of stock or otherwise unavailable, a substitution is made. As shown in FIGS. 3a and 3b, an inventory list (or "pick list") 124 of all the items actually included in the TracePak being shipped to the hospital is generated and is used as the recordation form referred to in FIG. 1. This recordation form 124 provides for a convenient reference for the healthcare facility personnel to use during the procedure to log usage of supplies at the time of consumption.

Typically, this completed recordation form 124 is entered into electronic form after the procedure for storage and for analysis in comparison to the procedural template. One of the most basic analyses is a comparison of the anticipated supply usage as set out in the template to the actual usage as set out in the recordation form 124. As is seen in FIGS. 3a and 3b, the preferred recordation form 124 shows the scheduled (anticipated) usage of each item 126 and has a blank 128 for entry of the number of items actually used. There are also blanks for showing the number of items scrapped 130 or returned 132 if less than all of the items were used (this information is useful in determining the cost of the procedure since scrapped items are "used" and must be paid for while returned items should not be charged for). The stored version is preferably identical except that all of the usage information is present (there are no blanks); also, to the extent that supplies are used, but not scheduled prior to the procedure, these items are added with the scheduled or issued amount showing zero.

Utilizing this basic comparison, a hospital may compare their custom procedural pack parts list and compare it to actual usage. In situations where a component is not used, that component may be eliminated from the tray, resulting in a cost savings for the hospital or healthcare provider. In situations where a component not scheduled on the template is frequently used in given procedure, it can be added to the procedural pack in order to save the hospital labor costs and inventory costs associated with keeping that component on hand and retrieving it for use during the procedure.

The above example of a preferred embodiment of the present invention is particularly directed to the DeRoyal TracePak custom procedural pack environment and utilizes the nested bill of materials associated with that system as a template. Particulars of such nested bills of materials and methods and systems for ordering medical supplies are described in U.S. Pat. No. 5,682,728, entitled Method For The Supply Of Medical Supplies To A Health-Care Institution Based On A Nested Bill Of Materials On A Procedure Level, the entire specification of which is hereby incorporated by reference thereto as if fully set forth herein.

While the bill of materials for a unitized container delivery system, procedural pack, doctor preference card, or other supply list associated with a certain procedure is a logical starting point for developing a template, template development need not start with such lists or bills of material. For example, in developing a template for use in the present system, the user of the system could start developing by developing a procedural pathway describing each phase of the care event. As each phase of the care event is mapped, more detail is added, until at the end, a procedural pathway listing all or most of the resources used in carrying out a particular procedure is listed. This listing then serves as the template.

For example, a given surgical procedure might consist of multiple distinct phases such as admission to the hospital, blood work/testing, surgical prep, anesthesia, surgery, postoperative recovery, and discharge. Each of these seven phases typically includes one or more care events requiring resource utilization. For example, the surgical prep phase might include the use of an orderly for doing the prep work and a prep tray for preparing the incision site. Further, there is a list of materials comprising the prep tray. Thus, the template for the surgical prep phase of the procedure includes at least the prep tray and could include the orderly (in order to facilitate analysis of labor requirements).

This process of breaking down each phase of the procedure ultimately results in a template that preferably includes all supplies/materials used in the procedure and, if desired, could include all other resources, such as labor resources, re-usable equipment and supplies, etc. Conversely, the template might only include a subset of an overall procedure, such as surgical prep, anesthesia, surgery, post-op, or even just a single phase, if so desired.

The procedural pathway organization of the information is very helpful in that it makes it easier for the care giver responsible for tracking resource consumption to properly associate actual resource consumption with the appropriate portion of the recordation form. For example, a commonly used supply during any medical procedure is a hemostat. Typically, many hemostats are used during various phases of surgery, and if the recordation form and template are not properly organized, it is difficult to determine, after the fact, when a hemostat is used. Thus, without procedural pathway organization of the information, it might not be possible to determine if certain quantities of hemostats were used during anesthesia, during surgery, during closing, or during recovery. For example, if only the total number of hemostats is recorded, and it turns out that five hemostats were not used, it would not be possible to determine where the overage originated (i.e., whether there were too many hemostats in the anesthesia tray, the incision tray, the suture tray, etc.). Thus, it would not be possible to refine the tray contents based upon the recorded information, even though it is known that extra hemostats were included. However, using the procedure based structure for the template and the recordation form, it is possible to track usage at the procedural level and determine exactly where mismatches between expected usage (from the template) and actual usage (from the recordation form) occur.

Furthermore, in the preferred embodiment, the recorded information is provided as input to a historical database. Each record in the database corresponds to a given procedure on a given patient. Thus, utilizing standard database commands and structure, a historical record of resource consumption may be developed and analyzed. For example, the database could be searched to determine the frequency with which the actual usage differed from the expected usage for a given procedure. Thus, looking at the historical data, a supply administrator could then take steps to change the supply orders so that frequently under utilized resources are excluded from future orders. Conversely, if it is observed that products which were not included on the template are frequently used during a given procedure, such products might be added to a custom procedural pack to reduce the labor and inventory costs associated with pulling that item from the hospital supply room and shifting those costs to the manufacturer or supplier.

Additionally, the historical data allows for the analysis of overall resource consumption for desired time periods. This information allows supply users, manufacturers and distributors to review historical usage and plan future production and inventory accordingly. In the current environment of just in time manufacturing and just in time shipping, such data, organized in accordance with the template and the recordation form, allow such users of the information to properly determine how to schedule production, raw material orders, inventory management, delivery, etc. in order to most cost effectively provide the necessary products to the users.

Furthermore, to the extent that labor and re-usable equipment resources are included in the template and recordkeeping, this information could be used for analyzing current staffing requirements, projecting future staffing levels and analyzing re-usable equipment requirements. For example, if labor resources (such as orderlies, nurses and doctors) are included on the template and recordation form, then it is possible to track anticipated labor requirements with actual usage. Using historical data, it is possible to eliminate unnecessary personnel resources, or determine if additional resources are required. Furthermore, since historical usage can be tracked, such data is useful for projecting future needs and cyclical variations for making staffing decisions and scheduling changes. In the area of re-usable medical equipment (such as respirators, heart-lung machines, dialysis machines, etc.) that may be used during the course of a medical procedure, inclusion in the template and the recordation form allows analysis to determine if usage estimates are accurate and allows for more informed decisions concerning new equipment purchases.

As a further benefit of implementation of the present invention, the consumption data generated may be used to assist in more accurately billing for supplies used and services rendered. For example, in some instances it is possible that supplies provided to the care event site and either used or not used may not be properly tracked. This situation results in billing errors, either resulting in the hospital not recovering legitimate expenses, or in patient overcharging. However, with the procedure based organization, the recordation form and the information contained in the template, highly accurate resource utilization information is generated and may be used in the billing of costs to the patient.

EXAMPLE

Deroyal Industries' RCL™ Software

Referring now to FIGS. 4 through 32, a preferred embodiment of a system for implementing the present invention is described. This implementation is made in the context as an additional module for DeRoyal Industries, Inc.'s, TracePak™ unitized medical supply delivery system (this product is currently sold by DeRoyal Industries, Inc. under the trademark RCL (Resource Consumption Log). These figures represent screen shots showing all of the various functions of the RCL software and, as such, represent a preferred embodiment of the present invention. Although this particular embodiment shows cooperation with the DeRoyal TracePak™ unitized delivery system, the software could be adapted to run with other unitized delivery systems, or with any other supply system used by a healthcare provider.

As an initial note, this software is programmed in Visual Basic Enterprise Edition, available from Microsoft, Inc. and versions are compatible with the Microsoft Access database software and/or SQL/Server software running under Microsoft Windows 3.X, Windows 95 or Windows NT. It should be noted that the program could be readily developed in a variety of other programming languages such as C++, could be adapted to work with a variety of other database software, or run under a variety of different operating systems such as DOS, Macintosh, or Unix by one skilled in the art without departing from the scope of the invention. As a final note, database tree structures, tables and schema are included below in Tables I–XVI for the purposes of completeness. It is believed that the following description is sufficient to allow one of ordinary skill in the art to reproduce this preferred embodiment of the invention without reference to Tables I–XVI; however, the included database organization information of Tables I–XVI shows how the database functions described herein are implemented in a Windows NT™ (a trademark of Microsoft Corporation) and SQL/Server environment.

As a final note before discussing the specifics of the preferred embodiment, in the case of the preferred embodiment described below, the necessary background information has already been entered. For example, the initial step of generating bills of materials for each procedure performed by the hospital (Step 1 of FIG. 1) and entering the supply, doctor, employee and other information has already taken place. As the discussion progresses, it will be noted how to input such information; however, the starting point will assume the input of much of the required information.

Logging a Procedure

Referring now to FIG. 4, the initial screen is shown which performs the function of restricting access to the program and database to authorized persons. The user enters the appropriate information in the appropriate blank and then clicks on the OK button 134 to proceed. Not only will the login screen shown in FIG. 4 restrict access to authorized personnel, it will, as is known in the art, call up the appropriate database information for use in the program.

Figure 5:
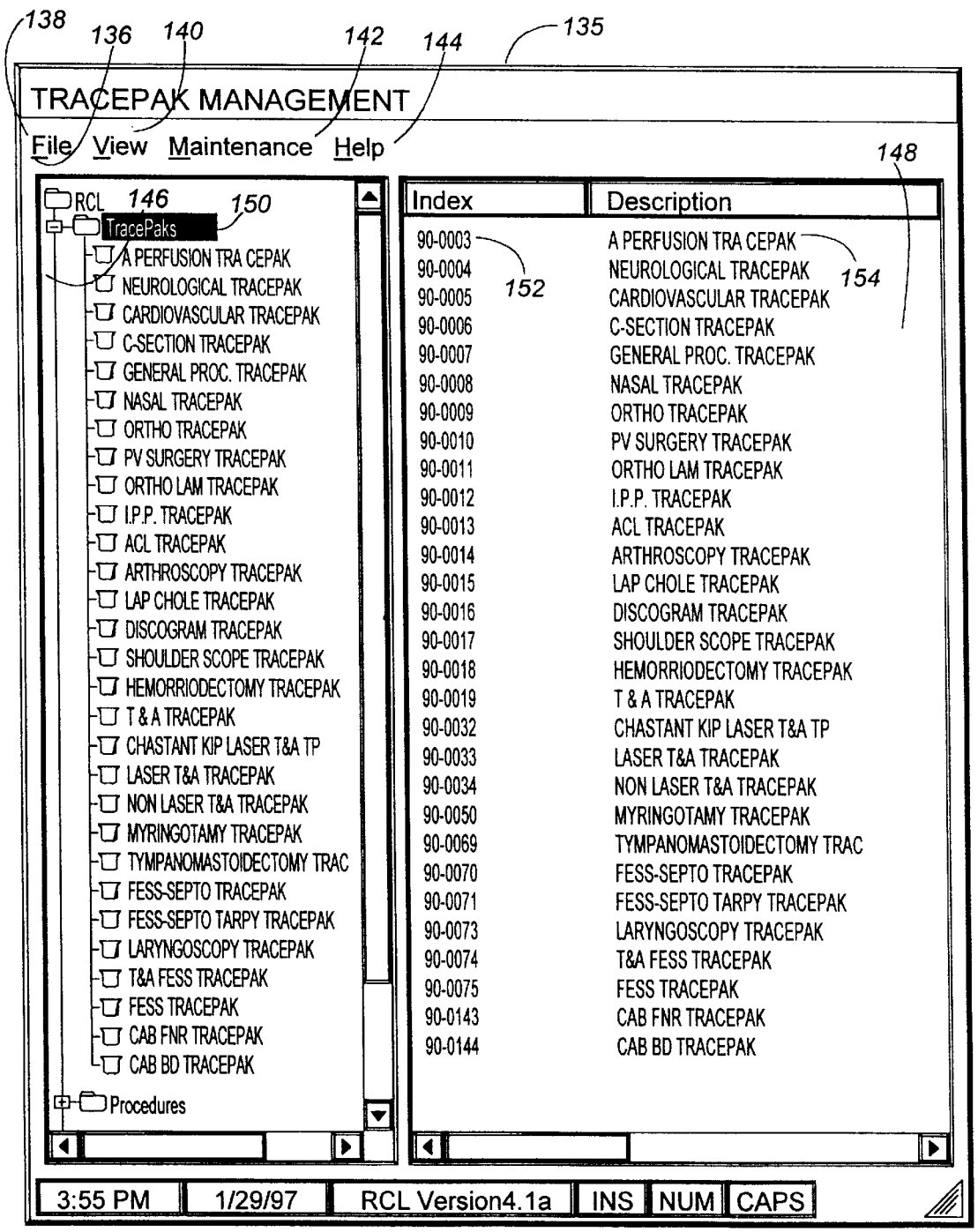
FIGS. 5–12 depict screen shots of various screens encountered in logging a procedure in the example.

FIG. 5 shows the TracePak™ screen 135 which appears after a successful login. As is known to anyone familiar with the Microsoft Windows operating system, the menu bar 136 sits at the top of the screen and has top level menus such as file 138, view 150, maintenance 142 and help 144. Each of these top level menus have sub-menus associated therewith which will allow the user to select certain functions and actions. In the case of the menu bar 135 of the preferred embodiment, the maintenance top level menu 142 provides most of the functionality specific to the preferred embodiment of the present invention and the functions provided thereby are described in detail below.

Also shown in FIG. 5 is a split screen display in which the overall information is shown in a tree display 146 and details of the selected level of the tree are shown in a list display 148. As is shown in FIG. 5, the folder TracePaks 150 is selected in the tree display 146 and, therefore, a list of all the TracePaks for that particular hospital is shown in the list display 148. More specifically, the list display 148 shows the part number 152 and a brief description 154 of each Trace-Pak contained in the TracePak folder 150. In the setting illustrated here, each of the TracePaks represents a supply grouping for a particular procedure. In a setting in which DeRoyal's TracePak system is not in use, the TracePak folder 150 could simply be replaced with a folder for supply lists and each list could then correspond to a type of surgical or medical procedure.

Figure 6:
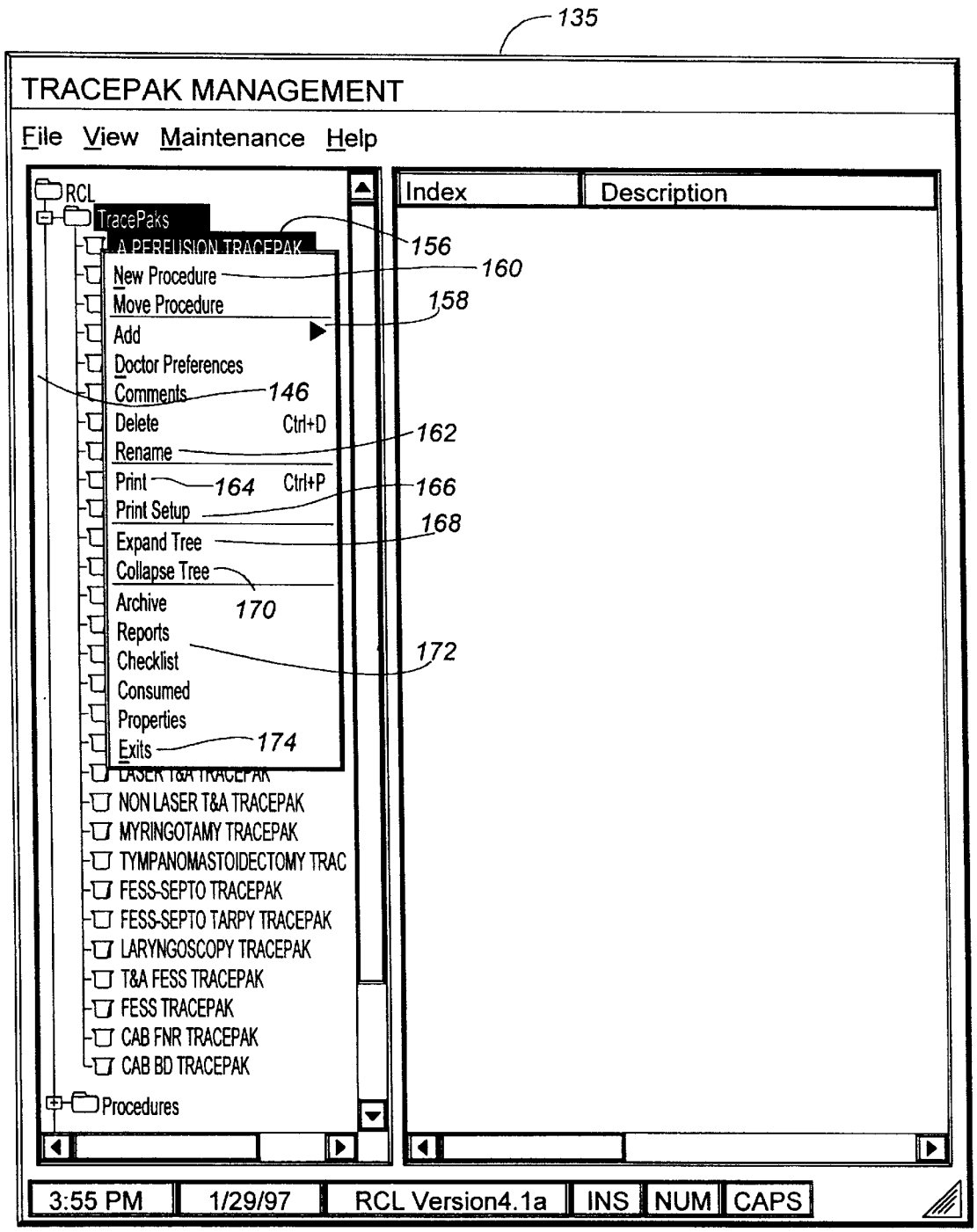

In FIG. 6, A Perfusion TracePak 156 has been selected from the tree display 146 and the properties function has been activated. In this embodiment, the properties function is activated with a click of the right mouse key (a standard operation under the Windows 95 and Windows NT operating systems) and calls up a menu of functions specific to the highlighted item. In particular, the properties function, when activated with this selection, calls a menu 158 which provides the user with the option of entering a new procedure 160, renaming the selected item 162, printing 164, setting up the print characteristics 166, expanding the tree 168 (which would show sub-headings), collapsing the tree 170, generating reports 172 or exiting 174. These choices are known to be available because these selections are shown in bold on the properties menu 158 when that function is available.

Figure 7:
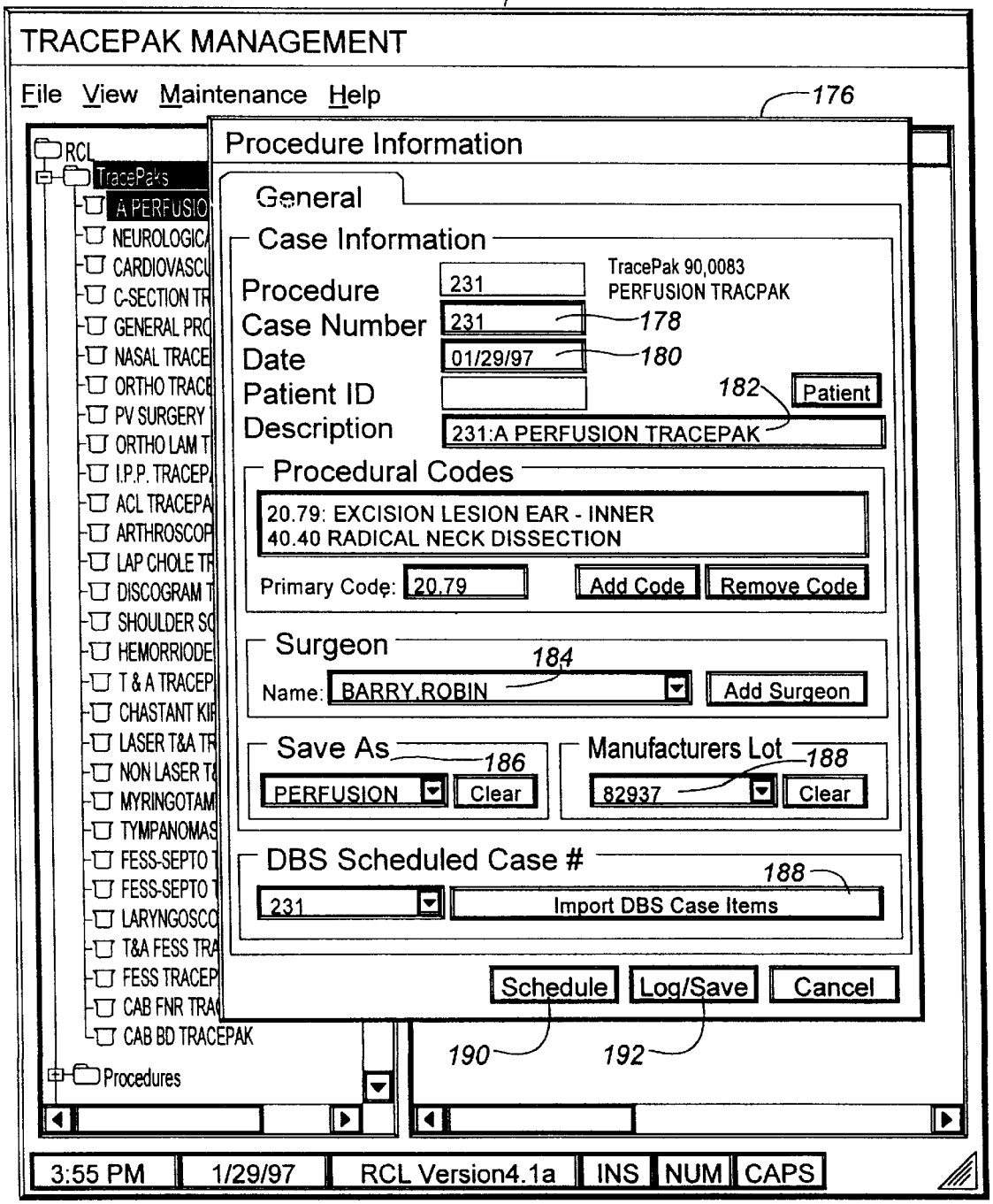

FIG. 7 shows a window which opens when the new procedure function is selected in the properties menu 158 described with respect to FIG. 6. The new procedure function results in the opening of the procedure information screen 176. This screen allows the user to input information concerning a procedure for which supply consumption logging needs to be completed. Each new procedure is assigned a unique case number 178 used for tracking purposes. Either the software provides the number, or alternatively, the hospital may assign a number corresponding to their admissions and patient identification practices. The date on which the procedure takes place is entered in the appropriate blank 180. The description 182 is automatically generated and includes the case number and the type of procedure. The user is also required to enter a surgeon's name in the appropriate location 184. The surgeon may be selected from a pre-entered list, or, if not on the list, may be added (inputting employee information will be described later). The save as box 186 allows the user to select a folder where the information about the procedure is stored for later retrieval. The remaining boxes allow the user to identify the manufacturer's lot number 188, for the supply bundle listed and, import information from another software platform which may include additional items of supply not listed in the bill of materials 188.

Once the information on the new procedure is entered, the user may select the Schedule function 190, if the procedure is to be performed in the future. If the procedure has already been performed, the user may select the Log/Save function 192. If the Schedule function 190 is selected, the user is provided with a location in which to enter the scheduling information before exiting the New Procedure screen 176 and being returned to the TracePak Management screen 135.

Figure 8:
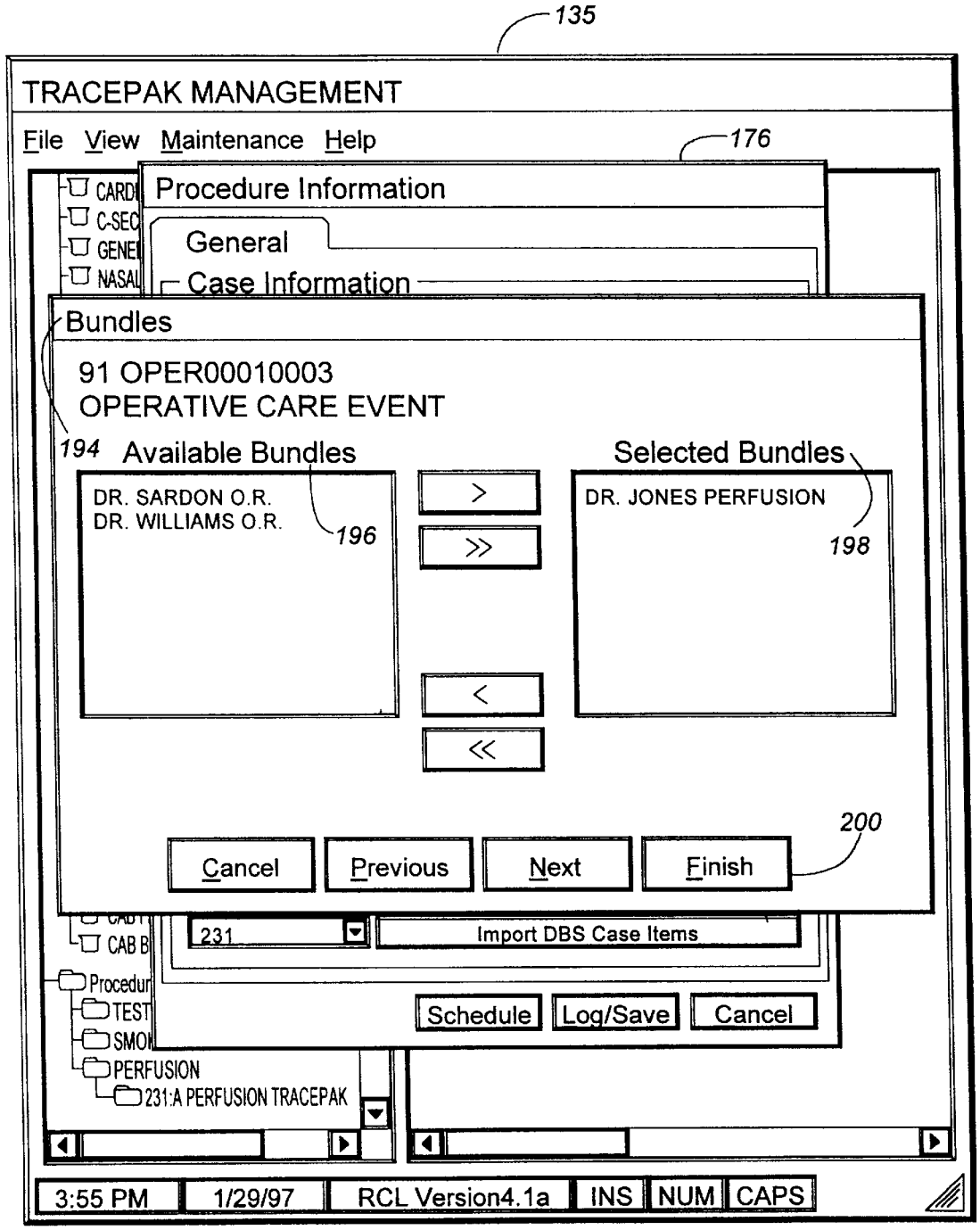

If the Log/Save function 192 is selected, the next screen seen by the user is the Bundles screen 194 shown in FIG. 8. As described previously, the idea of the bill of materials developed at the procedural level is to develop a supply list or bundle which is applicable to all surgical or medical procedures of a given type. For example, when developing a Knee Arthroscopy bill of materials, the goal is to include a standard listing of all supplies that are used in every performance of that procedure. However, individual doctors may require additional and/or specific items which vary from doctor to doctor. The preferred embodiment allows for that type of deviation by allowing the development of Conditional Bundles. These bundles are simply groups of supplies which are not included in the standard procedural bill of materials due to their dependence upon conditions such as who is performing the procedure. These lists may be developed beforehand or, may be developed at the time a new procedure is set up.

Referring now to FIG. 8, when the Bundles screen 194 is shown, the user is presented with information on pre-developed conditional bundles available for the given procedure in the Available Bundles window 196. As shown in the example of FIG. 8, there are two conditional bundles available, one for Dr. Sardon and one for Dr. Williams. Since Dr. Jones is the surgeon for the procedure, his conditional supply bundle is selected in the example of FIG. 8 and therefore appears in the Selected Bundles window 198. As a feature to prevent double listing, once an available conditional supply bundle is selected, it is no long present in the Available Bundles window 196. Once all of the pertinent conditional bundles for the procedure are selected, the user selects the Finish function 200, and the next screen appears.

Figure 9:
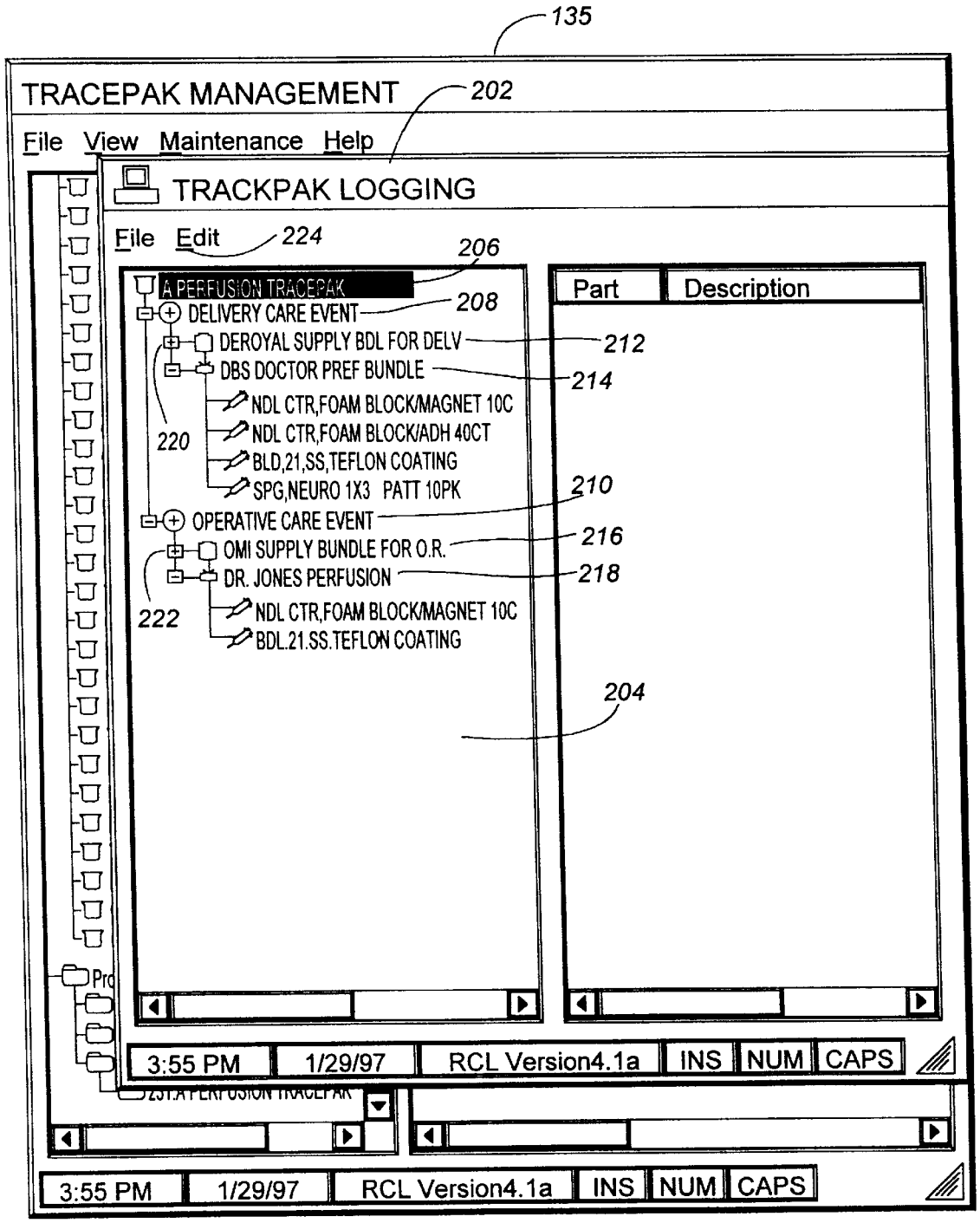

The next screen to appear after selecting the Finish function 200 on the Bundles screen is the TracePak Logging screen 202 shown in FIG. 9. Basically, in the tree window 204, there is provided a nested bill of materials. The highest level is the TracePak level 206, (or for a non-TracePak system user, the highest level is the name of the procedure). Displayed at the next level are the procedural care events 208, 210. In the case of the example, the selected TracePak is an Perfusion TracePak™ with which is associated two care events: (1) delivery care event 208, and (2) operative care event 210. These care events 208,210 represent the procedural level nesting discussed in the Background Of The Invention and represent sub-steps in the completion of the Perfusion procedure. At the next level, supply bundles and individual supplies associated with the care event may be listed. In the example of FIG. 9, the delivery care event 208 has two supply bundles associated with it: 1) a DeRoyal supply bundle for delivery 212 and 2) a DBS doctor preference bundle 214. Although not shown in this example, additional supply bundles or individually listed supplies could also be shown at this level.

Similarly, the operative care event 210 has two supply bundles 216, 218 associated with it. One is an OMI supply bundle for the operating room 216 and the other is the Dr. Jones Perfusion bundle 218 previously discussed with reference to FIG. 8.

At the next level of detail the contents of the supply bundles 214 and 218 are shown. In this example of FIG. 9, this is the most detailed level and individual supplies are shown. However, it is possible that the content of the any of the bundles could also be bundles and additional levels could be present. Furthermore, as is shown in FIG. 9, the plus signs 220 and 222 next to the DeRoyal supply bundle for delivery 212, and the OMI supply bundle for the operating room 216 indicate that there is an additional level of detail. In the case of these examples, selecting the plus icons 220 and 222 results in the revealing of the individual components of these bundles 212, 216.

Figure 10:
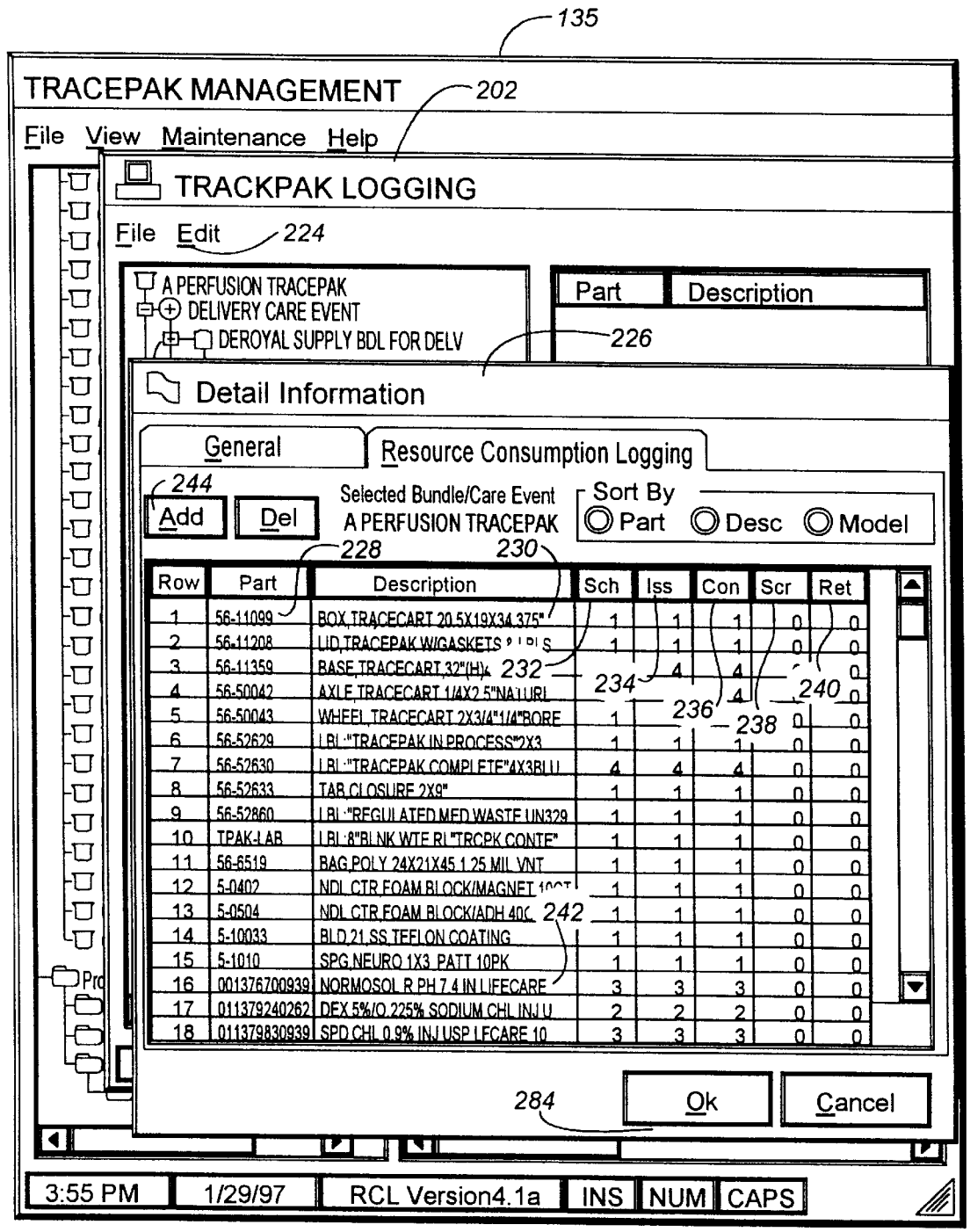

By selecting the highest level of the tree in the TracePak Logging screen (selected by activation of the properties function which is accessible under the Edit menu 224 or by right clicking on the desired level), in this example the Perfusion TracePak level 206 in FIG. 9, the Detail Information Screen 226 of FIG. 10 appears. This screen 226 shows the part no. 228, a description 230, the scheduled amount 232, the issued amount 234, the consumed amount 236, the scrapped amount 238 and the returned amount 240 for each individual supply item listed in the bill of materials for the selected procedure. This list includes the materials originally present in the selected template and the materials added through the addition of conditional supply bundles. It is at this point that resource consumption is logged.

In the DeRoyal TracePak system, each supply container contains a printed sheet similar to that shown as the screen 226 in FIG. 10 (pick list 124 from FIGS. 3a and 3b). This sheet 124 may be used for real time logging of resource consumption as the procedure is performed so that the computer logging can be completed at a later time. However, the information shown on the screen 226 may also be printed to provide such a sheet, or consumption may be logged onto the computer in real-time without the use of a print-out.

The Detail Information screen 226 is basically pre-completed, in that the software assumes that the consumption of an item is equal to the scheduled amount of the item, if no entry is made. This feature makes it easier to log resource consumption, since only exceptions or deviations from the scheduled usage need to be made. For example, if the only deviation from the scheduled usage was that only one unit of part number 001376700939, 242, was used during the procedure, the 3 in the consumed column 236 for that part is changed to 2. If the remaining unit were scrapped or returned, 1 is placed in either the scrapped column 238 or the returned column 240 for that part.

In some circumstances the need arises for a part that was not originally scheduled for a procedure. Where such a part was used during the procedure, it can be added to the Detail Information screen 236 (and thus, included in the logging) by selecting the add function 244 from the Detail Information screen 236.

Figure 11:
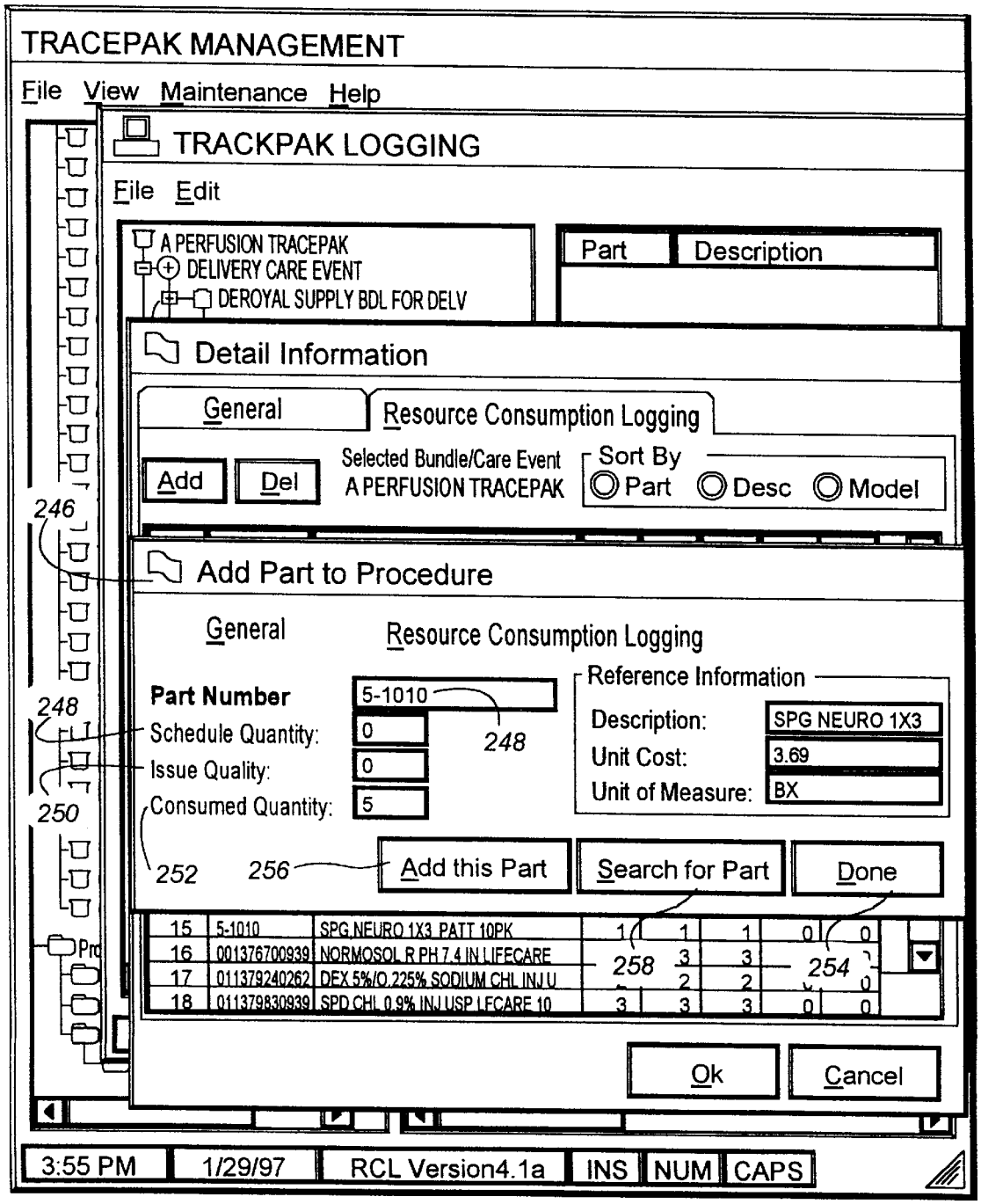
Figure 12:
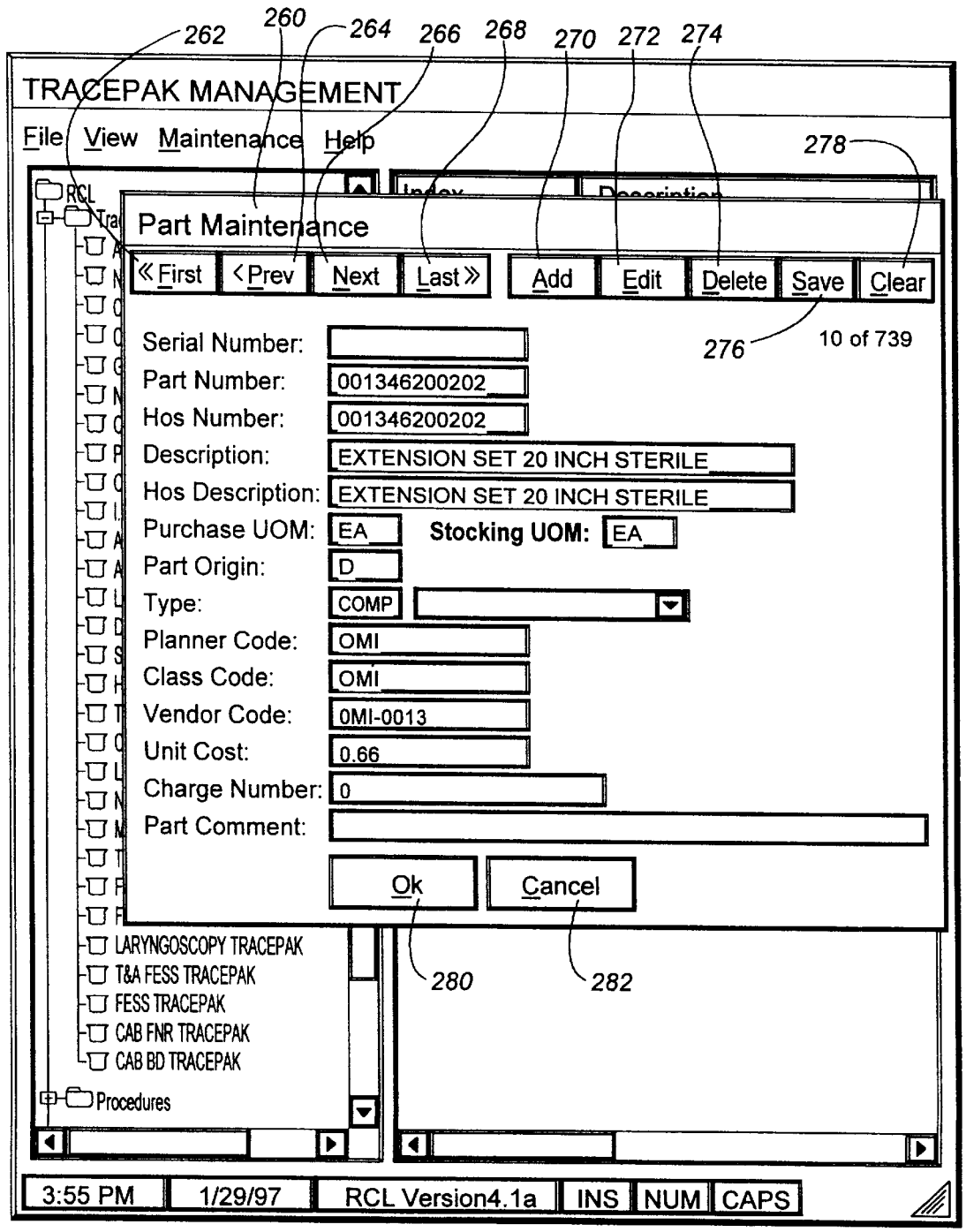

Once selected, the add function 236 causes the Add Part To Procedure screen 246 to appear as shown in FIG. 11. This screen allows the user to add a part number 248 which adds the information to the consumption log. Typically, the only number entered into the quantities boxes 248, 250, 252 is the number consumed (in this case 5) since the part was not previously scheduled or issued. If the part is typed in, and it has already been listed when the database was set up, the user can then select the Done function 254 and be returned to the Detail Information screen 226 of FIG. 10. If the user does not know the part number, or if the part has not previously been entered into the system, the user may select the Add this Part or Search for Part functions, 256, 258 and be transferred to the Part Maintenance screen 260 shown in FIG. 12.

The Part Maintenance screen 260 allows the user search for parts to add to consumption logs in the Detail Information screen 226 of FIG. 10, or to add new parts previously not listed to the database. This function is also accessible under the Maintenance menu selection 142 of FIG. 5 and is used in the setting up of the user's database to enter the parts to be a component of the database.

The Part Maintenance screen 260 provides search functions such as first 262, previous 264, next 266 and last 268 which allows the user to cycle through the individual part records to find a desired part. The add 270, edit 272, delete 274, and save 276 functions allow a user to add a new part, edit the record of the part on the screen, delete the part on the screen or save the information about the part on the screen. The clear function 278 clears the current record from the screen. The various blanks are self explanatory and provide information about the part for use in cost recovery and usage analysis. Once the new part is entered, or changes are made in the Part Maintenance screen 266, the user selects either OK 280 or cancel 282 to exit this function and is returned to wherever the user had been prior to accessing this function. If the user had been logging a procedure, the user could then complete the logging of the procedure.

Once the logging of the procedure has been completed on the Detail Information screen 226 of FIG. 10, the user selects the OK function 284 which ends the consumption logging process for that procedure and returns the user to the TracePak Management screen 135 of FIG. 5. Conversely, in this embodiment, the user has the option of highlighting a supply in the list shown on the TracePak Logging screen 202 of FIG. 9 and selecting the Quick Consume function (by depressing the right mouse button). This activates a small window showing the scheduled, issued, consumed, scrapped, and returned numbers for the item highlighted and the user can enter the appropriate number. This function is particularly useful when the actual consumption varied very little from the scheduled consumption and the user is able to find the information more quickly in the nested bill of materials structure of the TracePak Logging screen 202.

Creating Reports

As was described generally, the function of the software is to allow for the tracking of resource consumption during a procedure for the purposes of analysis. In general, such analysis could consist of cost recovery, historical usage tracking, inventory reduction, procedure standardization, etc. In particular, the use of unitized delivery systems in hospitals is growing in which nearly all supplies needed for a given procedure are packaged into one unit and ordered on a just in time basis. In this manner, the hospital can reduce its in-stock inventory and not have operating capital tied up in supply inventory. However, hospitals typically must maintain supplies which are either not available from the supplier of the unitized package, or vary from procedure to procedure due to doctor preferences, variations in procedures, or from simply not having the information available in a readily accessible form.

Figure 13:
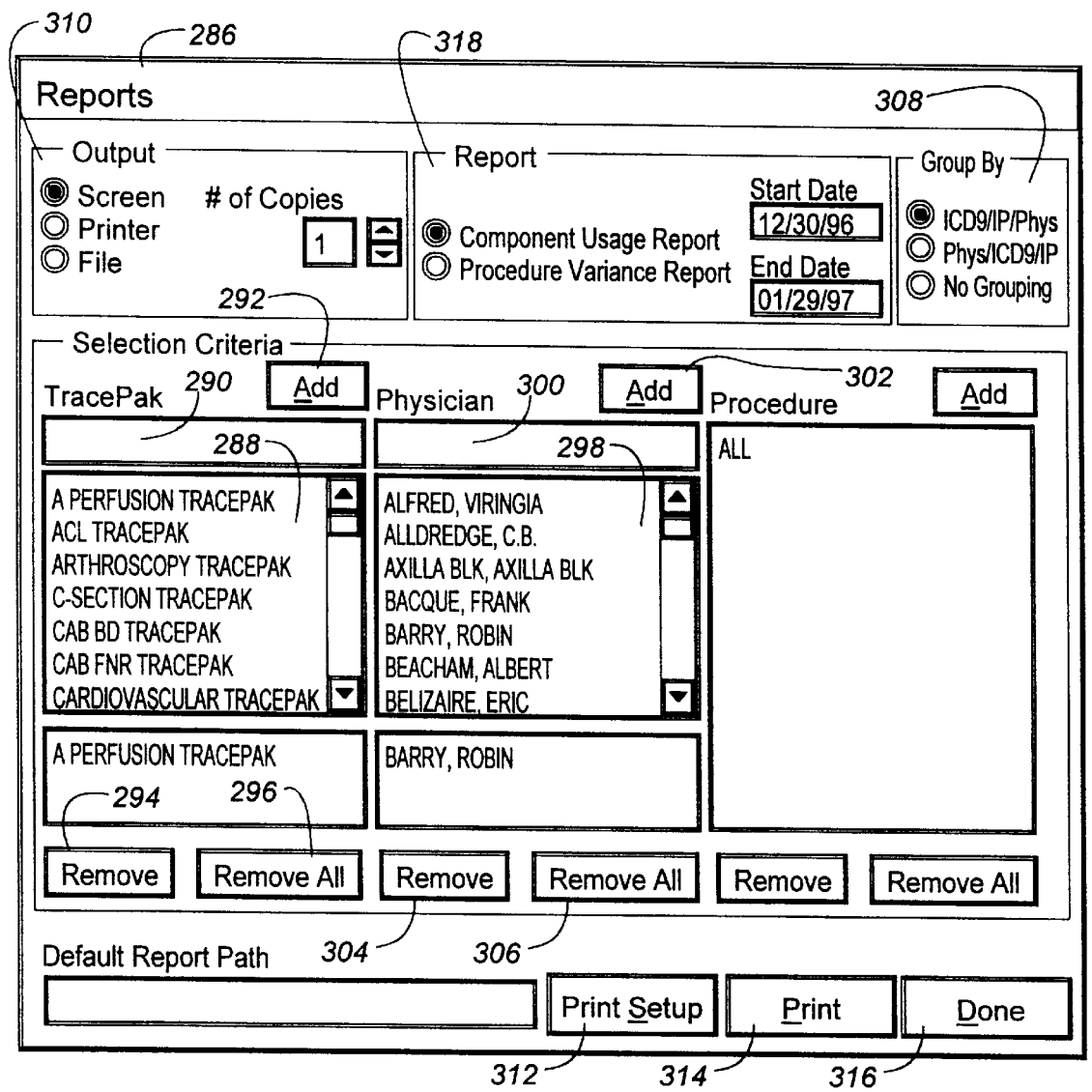
FIG. 13 depicts a screen shot showing the creation of reports in the example.

The RCL™ software of this Example, provides for analyzing the data input during the logging process by generating a variety of reports. Referring now to FIG. 13, the Reports screen 286 is shown. The Reports screen 286 allows the user to select the procedure(s) to be analyzed by selecting a procedure from a window 288 showing all available procedures. The procedure(s) selected will be shown in window 290. With the procedure selection, the user may elect to add 292, remove 294 or remove all 296 procedures by selecting the appropriate button. Likewise, the user may select from a list of all doctors shown in window 298, with the selected doctor's name appearing in a window 300. Also like the procedure selection, the user may add 302, remove 304 or remove all 306 doctors available for inclusion in the report. For the output of the information, the user may select the information to be grouped according to a particular hierarchy, this function is shown in the Group by window 308. The user may also select the location where the report will be output in the Output window 310. Furthermore, the printer functions of Print Setup 312 and Print 314 may be selected by selecting the proper button. Finally, the Done function 316 may be selected to exit the Reports screen 286 when finished.

Referring now to the Report window 318, once all of the other information is selected by the user, the user may specify the type of report and the time range for which the report will be generated. Currently, with this Example, three types of report are available: a Volatility report (one page shown in FIG. 14), a Usage report (one page shown in FIG. 15) and a Procedure Variance report (one page shown in FIG. 16).

Referring to FIG. 14 the Volatility report 319 provides information regarding what the expected supply usage is (based upon the procedural template) and how actual usage compares to the expected usage. In the example of FIG. 14, the report is sorted by the doctors using a procedural pack for C-sections. In the Occurrences category 320, there are three columns, Exp 322, Var 324, and Pct 326. The Exp column 322 show the number of procedures in which a particular component of a procedural pack was scheduled to be used by the surgeon. The Var column 324 shows the number of times the usage of that component did not equal the amount scheduled to be used. The Pct column 326 shows the percentage of procedures where the actual usage varied from the scheduled usage. It should be noted that not all items from the procedural template will appear in the Volatility report 319. The only items that appear are those items where a variance between scheduled usage and actual usage occurred. For Dr. Bernard in the example, there were three C-Sections performed during the report period (indicated by the 3 in the Exp column 322). In two of these C-Sections, the actual usage of the Irrigation Bulb Syringe 328, varied from the scheduled usage in two cases (indicated by the 2 in the Var column 324).

The next category in the Volatility report 319 is the Components category 330. This category has two columns, a Sch column 332 and a Use column 334. For parts where a variance has occurred, the Sch column 332 shows the total number of components expected to be used in the procedures performed by the given doctor (in the case of Dr. Bernard in the example, a total of 3 irrigation bulb syringes were scheduled to be used in the 3 C-Sections summarized in the Volatility report 319) while the Use column 334 shows the actual number of components used (in the case of Dr. Bernard in the example, only one bulb syringe was used in three procedures).

The next report category is the Under-Use category 336. In the Qty column 338, the reports shows the total quantity of under usage for the component for all procedures for a given doctor. In the Exp column 340, the number of times under-usage of the component was experienced is provided. In the % of Exp column 342, the percentage of cases in which a under usage occurred for a component is shown. In the Avg. Under column 344, the average under usage of the components, on a per procedure basis is provided. For example, in the case of the Dr. Bernard C-Section list, the total quantity of bulb syringe under usage is 2 (shown in the Qty column 338), the number of cases in which under usage occurred is 2 (shown in the Exp column 340), the percentage of total cases in which under usage occurred is 66% (shown in the % of Exp column 342) and the average under usage of this component is 1.00 (shown in the Avg. Under column 344; the average under is the Qty fig. divided by the Exp fig.). The same information is provided in the Over-Use category 346 and the explanation will not be repeated.

This Component Volatility Report 319 provides a supply manager with a quick review of the variation in actual usage of components versus scheduled usage. By utilizing this type of information, the manager may review component volatility to determine when additional items should be stocked in addition to the procedural packs ordered for a given procedure. Also, to the extent that the over-use or under-use of a component is consistent, the manager might wish to adjust the bill of materials for the given procedure to minimize waste of components (under use) or to add components to minimize additional inventory requirements (a consistent over-use situation). Also, to the extent that the bill of materials is adjusted, the corresponding procedural template needs to be adjusted as well.

Another type of report, the Component Usage Report 348, is shown in FIG. 15. Basically, the Component Usage Report 348 provides an actual component usage history, component by component, for a desired procedural template. The example of FIG. 15 shows a component usage report for a procedural template for a C-Section and is sorted by doctor. The component usage report may reflect usage for a given time period, for all procedures, for all procedures for a given doctor, or various combinations of the foregoing. This report is useful for looking at historical consumption for manufacturing purposes, ordering of raw materials, forecasting future orders, etc.

A final type of standard report generated by the software of the example is the Procedure Variance Report 256, shown in FIG. 16. This report is sorted by doctor and under the doctor's name shows all of the various types of procedures performed by the doctor (each procedure corresponding to a procedural template) along with costing information relevant to the historical usage information.

For example, for Dr. Bernard's C-Section historical procedure usage, a total of 3 C-Sections (shown in the Total Procedures column 352) were performed during the reporting period. The total cost of the supplies used in the three procedures was $390.25 (shown in the Total Cost column 354). The lowest cost of supplies for a procedure was $129.31 (shown in the Minimum column 356). The average cost for supplies for a procedure was $130.08 (shown in the Average column 358). The highest cost of supplies for a procedure was $185.75 (shown in the Maximum column 360). Finally, the standard cost deviation was $18.09 (shown in the Standard Deviation column 362). This information allows the hospital or other care-giver to track costs and compare costs from procedure to procedure, doctor to doctor or other relationships. This type of information is useful for budget forecasting, cost analysis, etc.

It should be noted that while one page from three standard reports is described with respect to the example, a variety of different reports could be generated by one skilled in the art. For example, since all of the information is provided in searchable fields and records, a variety of custom reports could be generated with simple database commands. Again, the key item is that the procedural template architecture provides a common framework for the collection, organization, entry and retrieval of data in a manner which maximizes its usefulness to the user.

Patient Information

Figure 17:
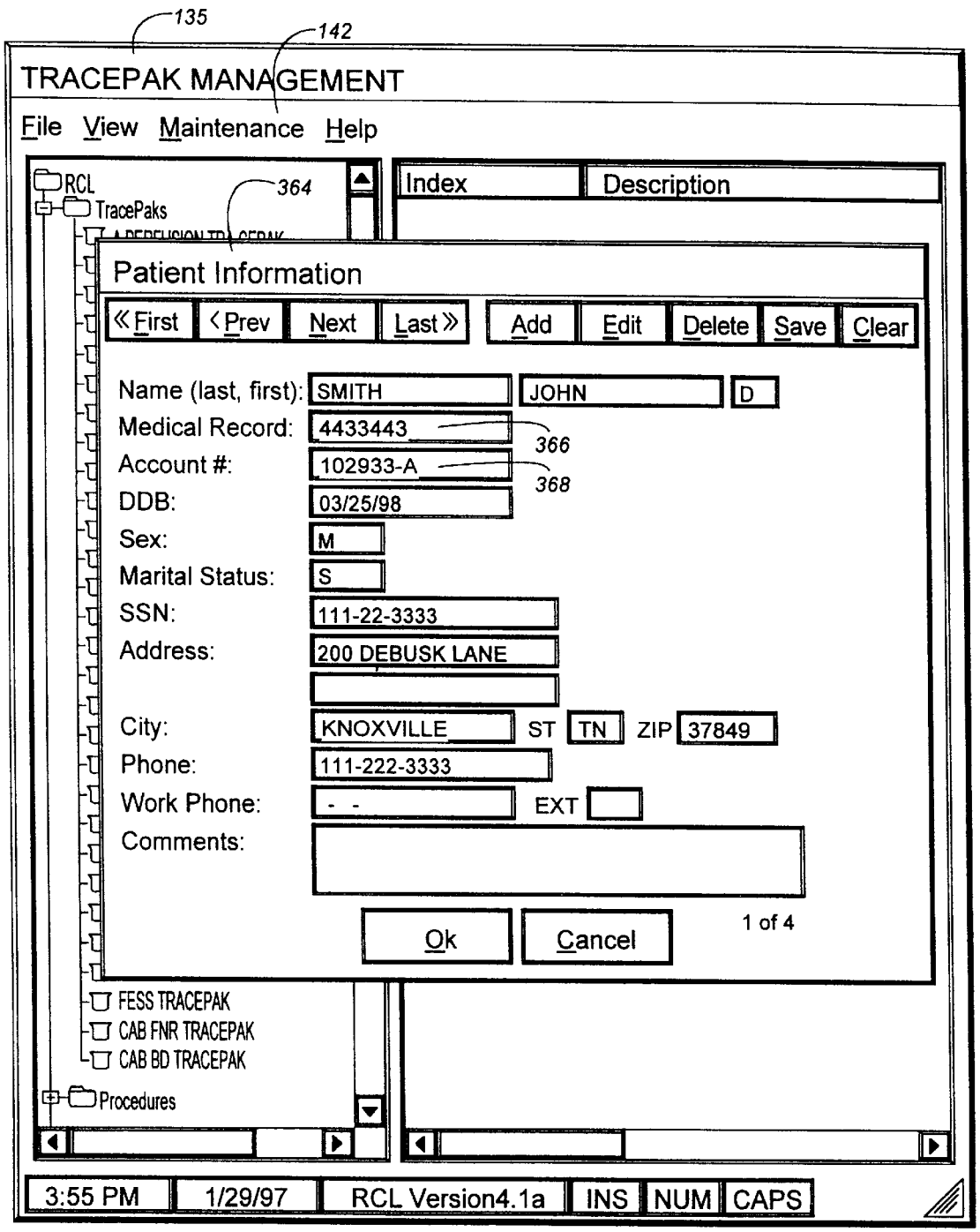
FIG. 17 depicts a screen shot showing the input of patient information in the example.
Figure 18:
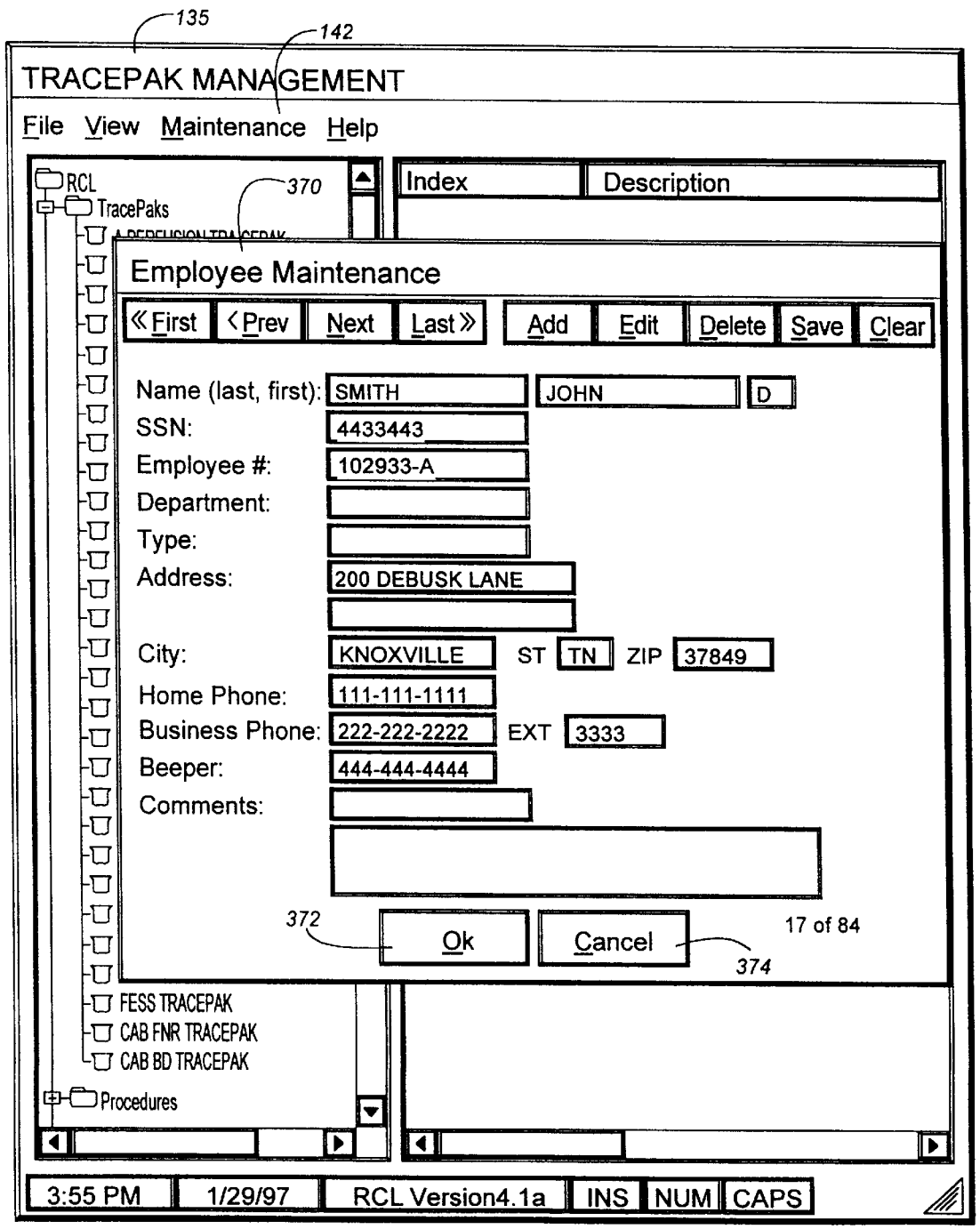
FIG. 18 depicts a screen shot showing the input of employee information in the example.

The Patient Information screen 364 of the RCL™ software of the example is shown in FIG. 17. This function is activated by selecting the patient selection under the Maintenance menu 142 and allows for the entry of information concerning a particular patient. If desired, the relevant information about a given patient could be entered into the system and, when a procedure is being scheduled or logged as previously described, the patient record could be associated with the procedure record. Completion of this record allows for better tracking of costs for billing purposes, location of past patient histories for previous procedures, and a variety of other information. As is seen in the Patient Information screen 364, the user may toggle between different patient records by selecting the First function, the Previous function, the Next function or the Last function. Also, for record maintenance, the user may add a new patient record by selecting the Add function, may edit a patient record by selecting the proper record and selecting the Edit function, may delete a patient record by selecting the Delete function, may save the patient record by selecting the Save function, and may clear the present record by selecting the Clear function (clearing all of the fields of information)(these functions are the same database maintenance functions previously described).

The available information fields allow the storage of useful information about the patient and allow for the correlation of the patient record to other hospital information. For example the number entered into the Medical Record field 266 typically corresponds to the patient identification number used in the medical chart while the Account # field 268 corresponds to the billing number assigned to the patient. Thus, to the extent that separate information systems were used to track medical history and/or billing, the Patient Information function of RCL™ software allows for the cross-correlation of the separate information systems.

Employee Maintenance

The Employee Maintenance screen 370 allows the user of the RCL™ software of the example to input and/or edit information concerning employees who will be performing procedures in the healthcare institution. The Employee Maintenance screen 370 is selected from the drop down Maintenance menu 192 previously described. Potentially, all employees providing any service along the procedural pathway could be entered; however, typically the surgeons are entered at a minimum. Like other informational records described herein, the Employee Maintenance screen 370 has a number of informational fields which allow for the entering of information such as Name, Social Security Number 374, Employee Number, Department, Type, Address, City, State, Zip Code, Phone Numbers and, Beeper (or Pager) Number, and text Comments.

In addition, since the Employee Maintenance Screen 370 is used to call up a list of records, there are search functions provided as well. For example, the First function takes the user to the first record in the list, the Prev function takes the user to the immediately preceding record in the list, the Next function takes the user to the next record in the list and the Last function takes the user to the last record in the list. Also, for entering new information or editing information in the selected record, the Add function allows the user to add a new employee record, the Edit function allows the user to edit the current employee record, the Delete function allows the user to delete the current employee record and the Save function allows the user to save the current record. The Clear function clears the current record from the list. Once the user has finished with the Employee Maintenance screen 370 the OK 372 or Cancel 374 function is used to exit the Employee Maintenance screen 370.

Bundle Maintenance

Previously, the process of adding a pre-configured bundle was described with respect to the scheduling of a procedure in the RCL™ software. As was described, bundles can be added to a procedural template in order to customize a procedure for a given doctor or to include special components for a particular patient. In particular, some bundles, standard items of supplies used at a particular point in the clinical pathway, are bundled as a standard item; other bundles, conditional bundles, are built from the available parts (entered through the parts maintenance function) and are only used with certain procedures (i.e., procedures performed by a particular doctor).

Figure 19:
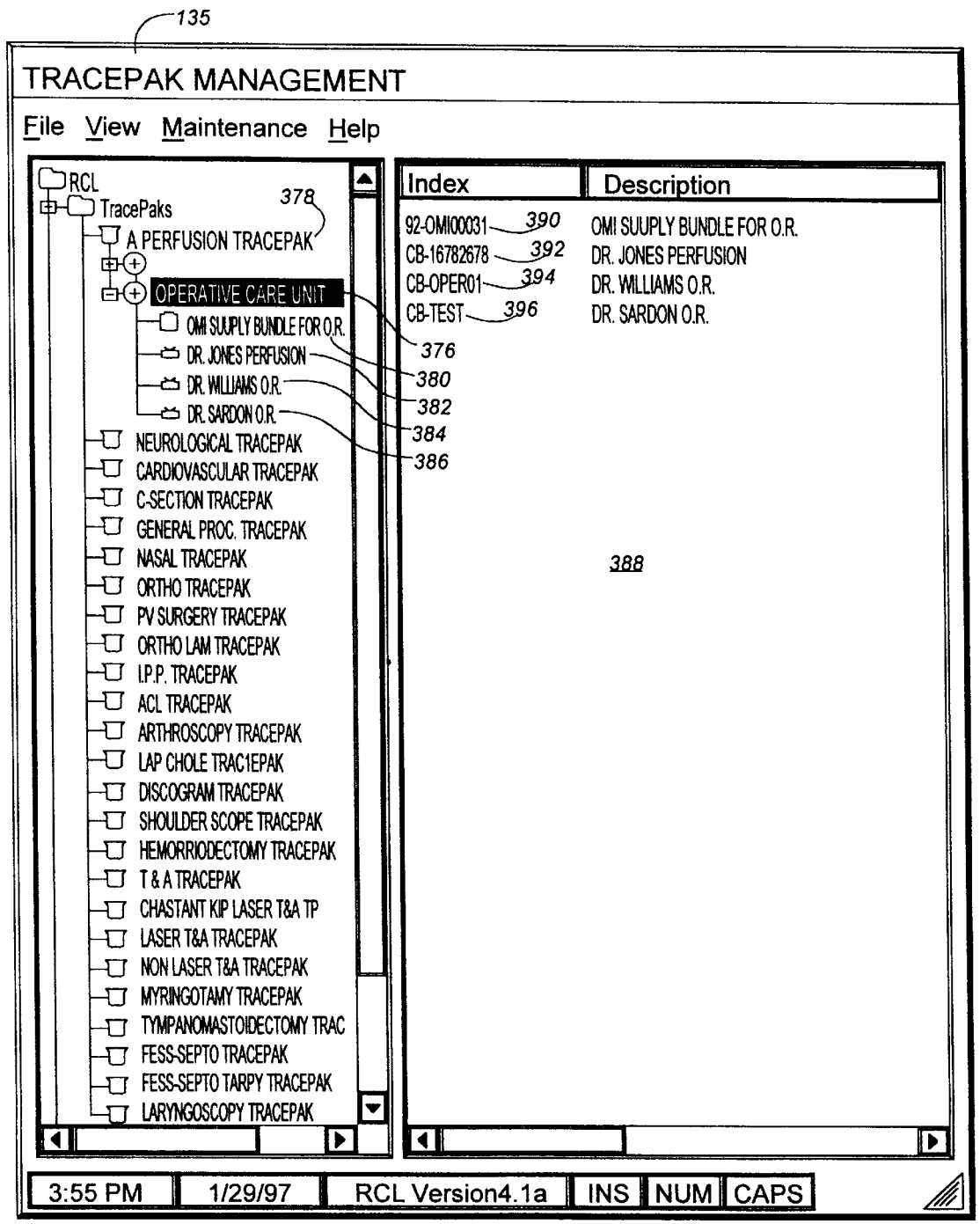
FIGS. 19–26 depict screen shots showing the creation and maintenance of bundles in the example.

FIGS. 19 through 26 show the functions associated with building and maintaining supply bundles in the RCL™ software. Referring now to FIG. 19, the TracePak Management screen 135 is shown with the Operative Care Event 376 of the Perfusion TracePak™ 378 selected. Shown under the selected Operative Care Event 376 are supply bundles. The first, the OMI Supply Bundle For O.R. 386, is a standard supply bundle which is a part of the standard procedural template for the Perfusion Tracepak™ 378. However, shown below the OMI Supply Bundle 380 are three conditional supply bundles 382, 384, and 386 (identified by an icon which is different from the standard supply bundle icon). With the Operative Care Event 376 selected, the available supply bundles for that care event are also shown in the right hand window 388, which also shows the part numbers 390, 392, 394 and 396 for those bundles.

Figure 20:
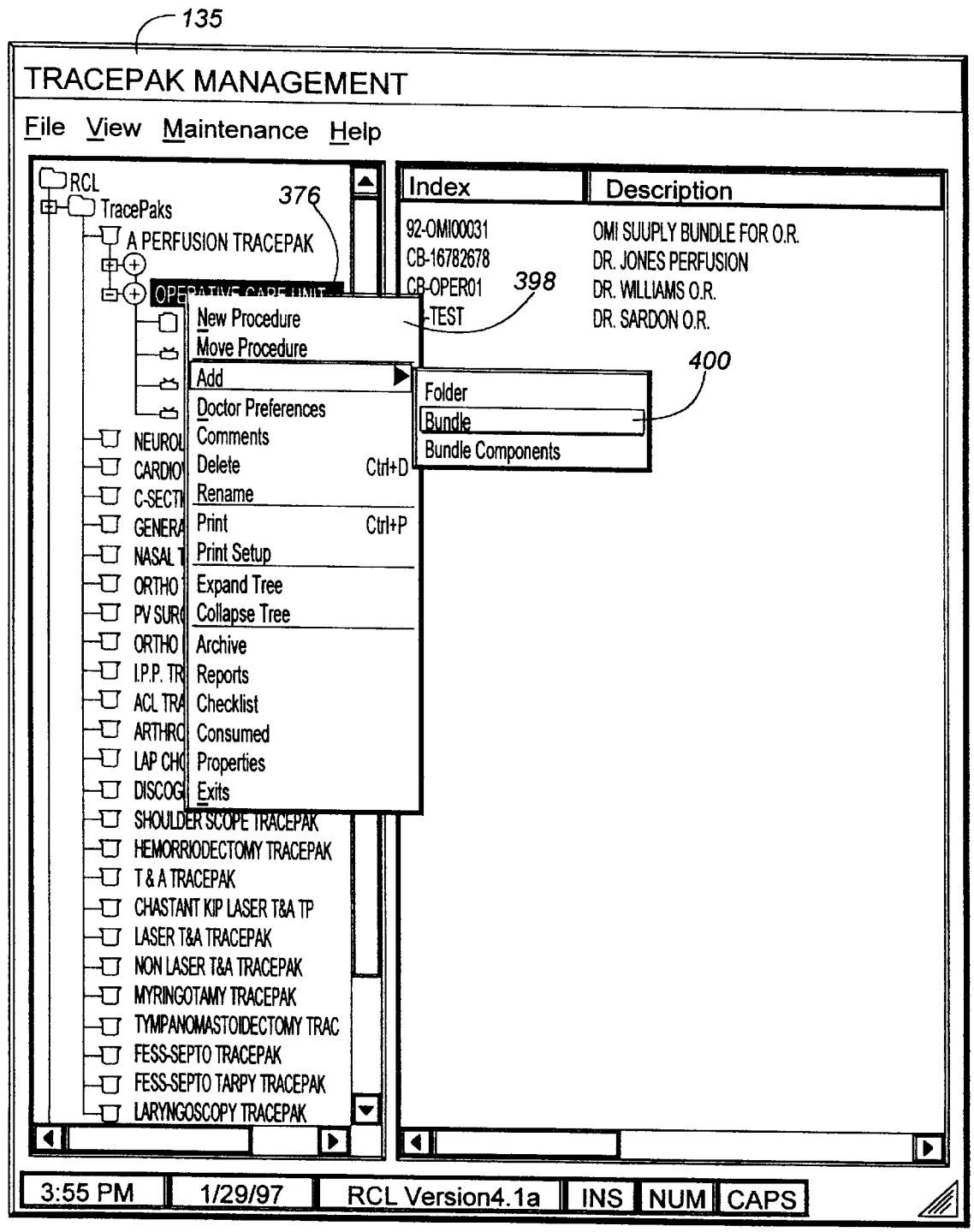

Referring now to FIG. 20, with the Operative Care Event 376 highlighted by placing the cursor over that item, a menu 398 may be called by depressing the right mouse key (or other action defined in the software). In the example of FIG. 20, the Add function is selected which calls the sub-menu 400 shown. Also in the example of FIG. 20 the Bundle function is selected under the Add function which allows the user to add a bundle to the list of conditional bundles.

Figure 21:
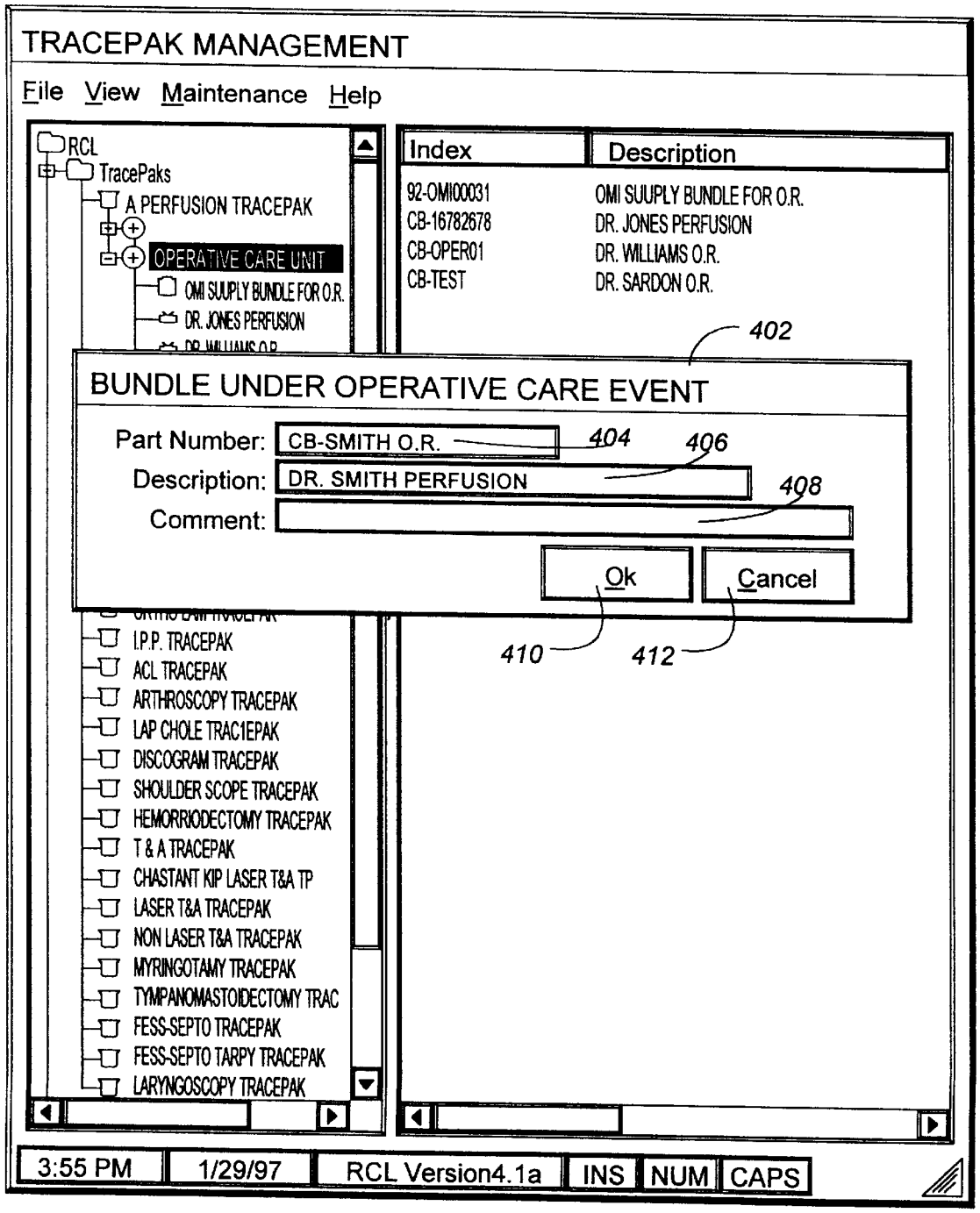

Referring now to FIG. 21, after selecting the add bundle function previously, the user is presented with a Bundle screen 402. The user is prompted to enter a part number or name in the Part Number field 404, a description in the Description field 406 and may add additional comments in the comment field 408. After entering the desired information, the user may proceed with creation of the bundle by selecting the OK function 410 or may cancel the add bundle feature by selecting the Cancel function 412 and be returned to the TracePak™ Management screen 135 of FIG. 19.

Figure 22:
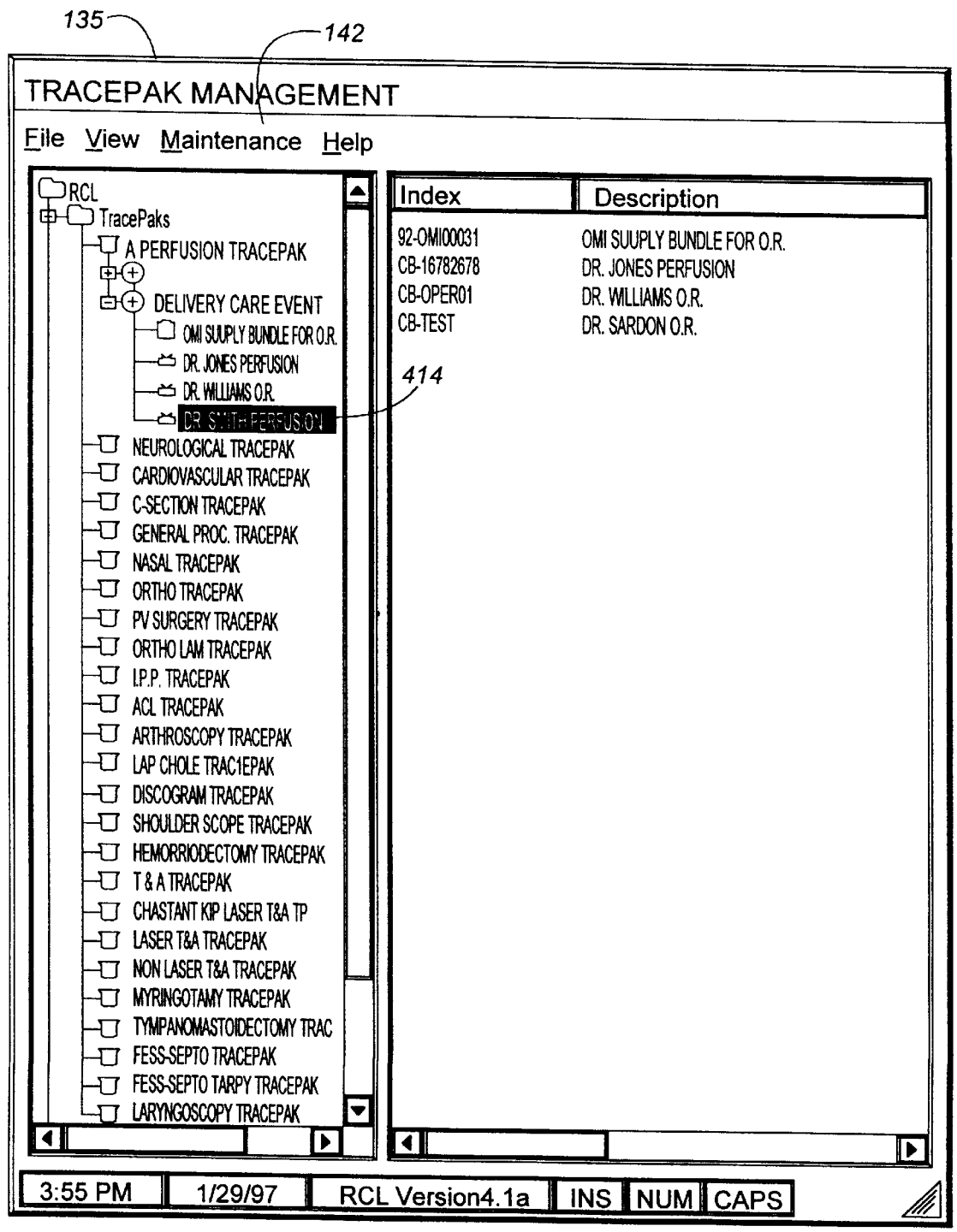
Figure 23:
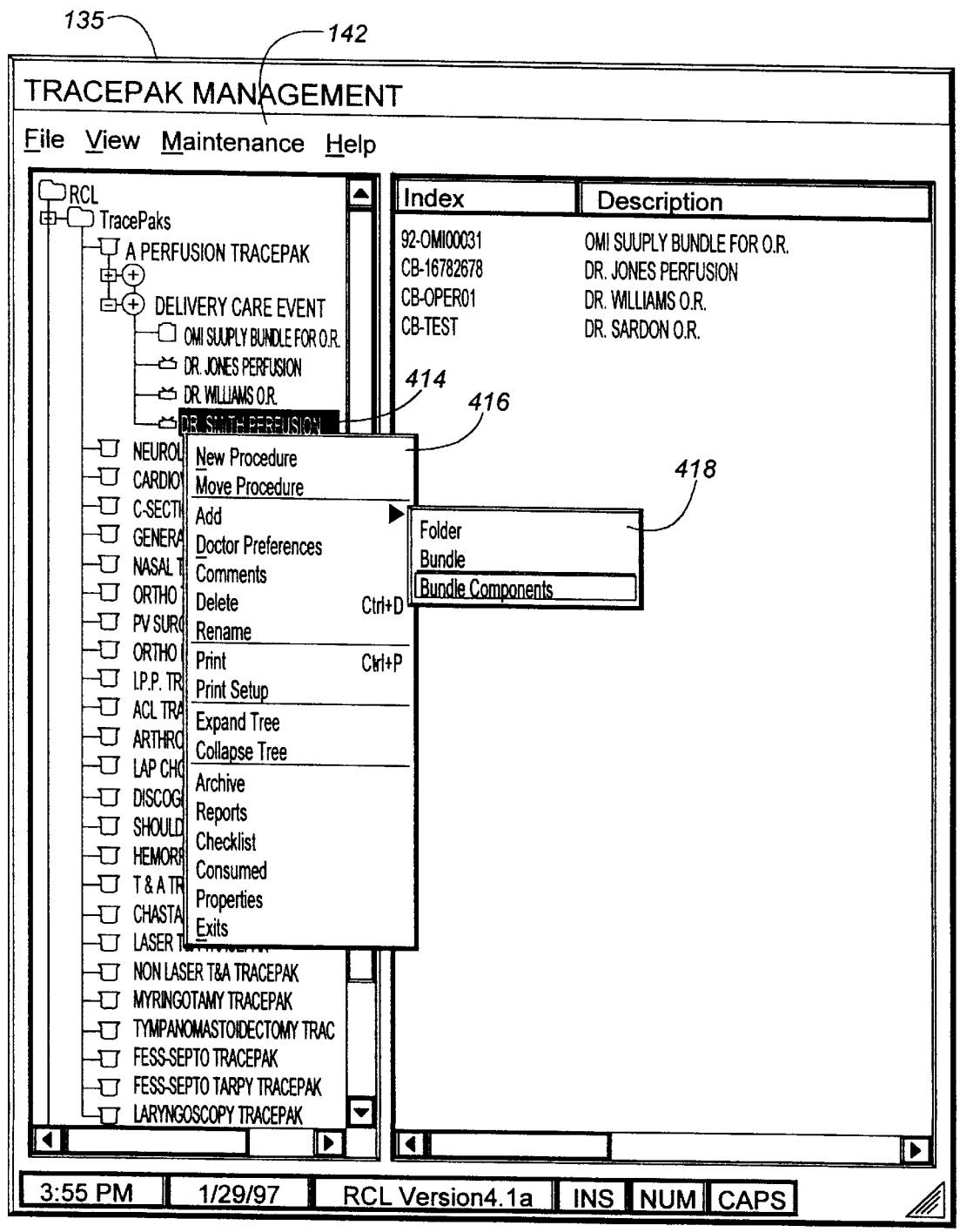
Figure 24:
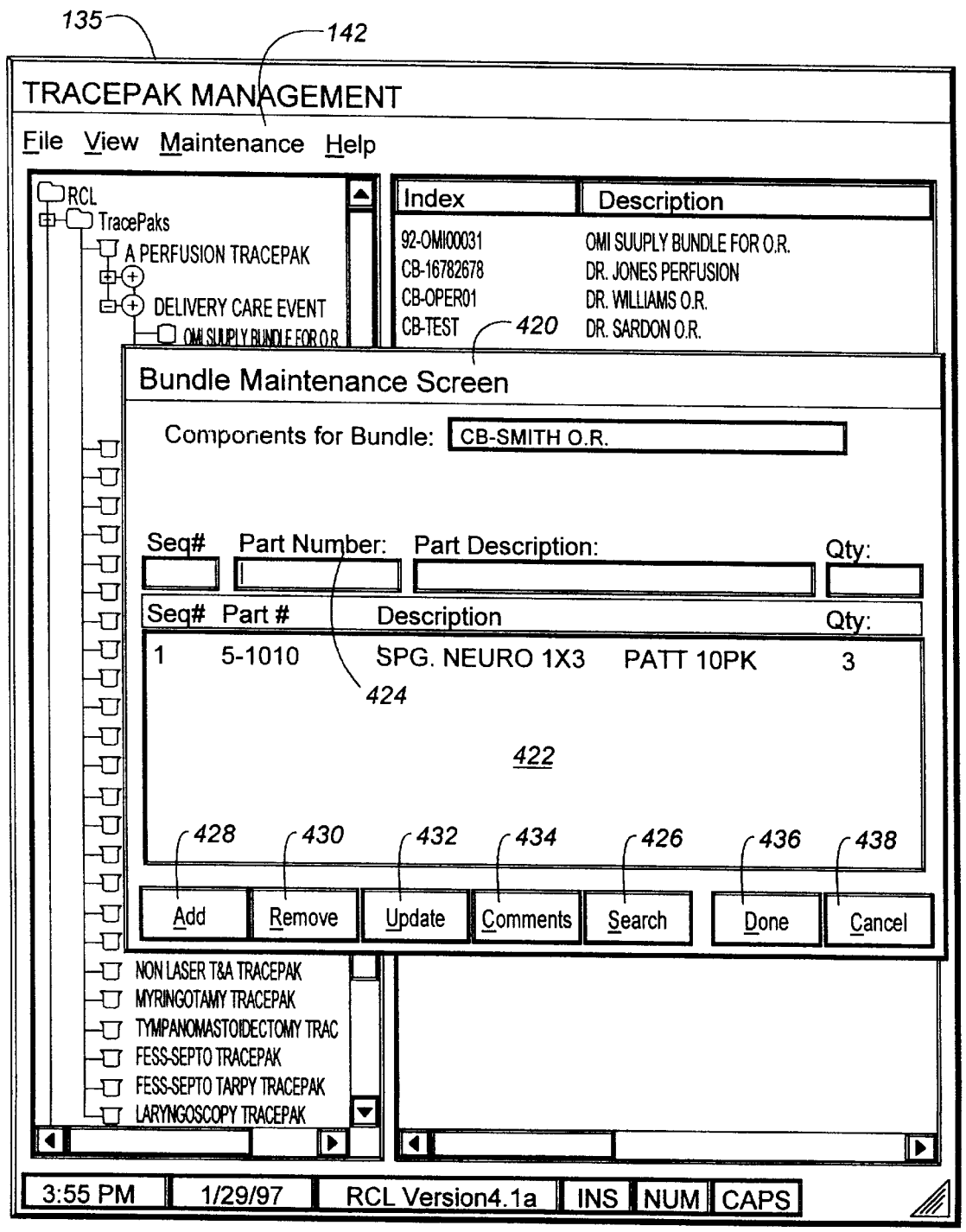

Once the OK function 410 is selected, the new bundle 414 appears in the TracePak™ Management screen 135, as shown in FIG. 22. By highlighting the new bundle 414 and clicking the right mouse button (the standard "properties" function under Windows 95 and Windows NT) the properties menu 416 appears for the selected bundle and lists choices for that bundle (since a bundle is selected in this case, as opposed to an operative care event was selected for the addition of a new bundle as was the case with reference to FIG. 20, there are more available choices for actions as indicated by the darker menu choices) as shown in FIG. 23. A new bundle was just created as described with Reference to FIG. 22. Now, in order to add the desired parts to the new bundle, the choice selected under the properties menu 416 is Add, which shows the Add sub-menu 418 with the Bundle Components selection highlighted. By selecting the Bundle Components choice under the Add sub-menu 418, the Bundle Maintenance Screen 420 is accessed as shown in FIG. 24. The Bundle Maintenance Screen 420 identifies the bundle being maintained and shows the parts selected for the chosen bundle in the part window 422. If a new part is to be added, that number may be typed into the part number box 424. Alternatively, if the part number is not known, the user may search the parts database by selecting the Search function 426. Selecting this function will activate the Parts Maintenance feature which was previously described, which will allow the parts database to be searched for the purposes of determining which parts to add to the Bundle. Also, if the desired part is found, it can be added to the bundle by selecting the Add function 428, an undesired part may be removed from the bundle by selecting the Delete function 430, new information about the part may be retrieved by selecting the Update function 432, or additional comments about the parts or the bundle may be added by selecting the Comment function 434. Once the user is finished with the bundle, the Done function 436 may be selected, or if the user wants to exit without changing anything, the Cancel function 438 may be selected which will return the user to the TracePak™ Management Screen 135.

Figure 25:
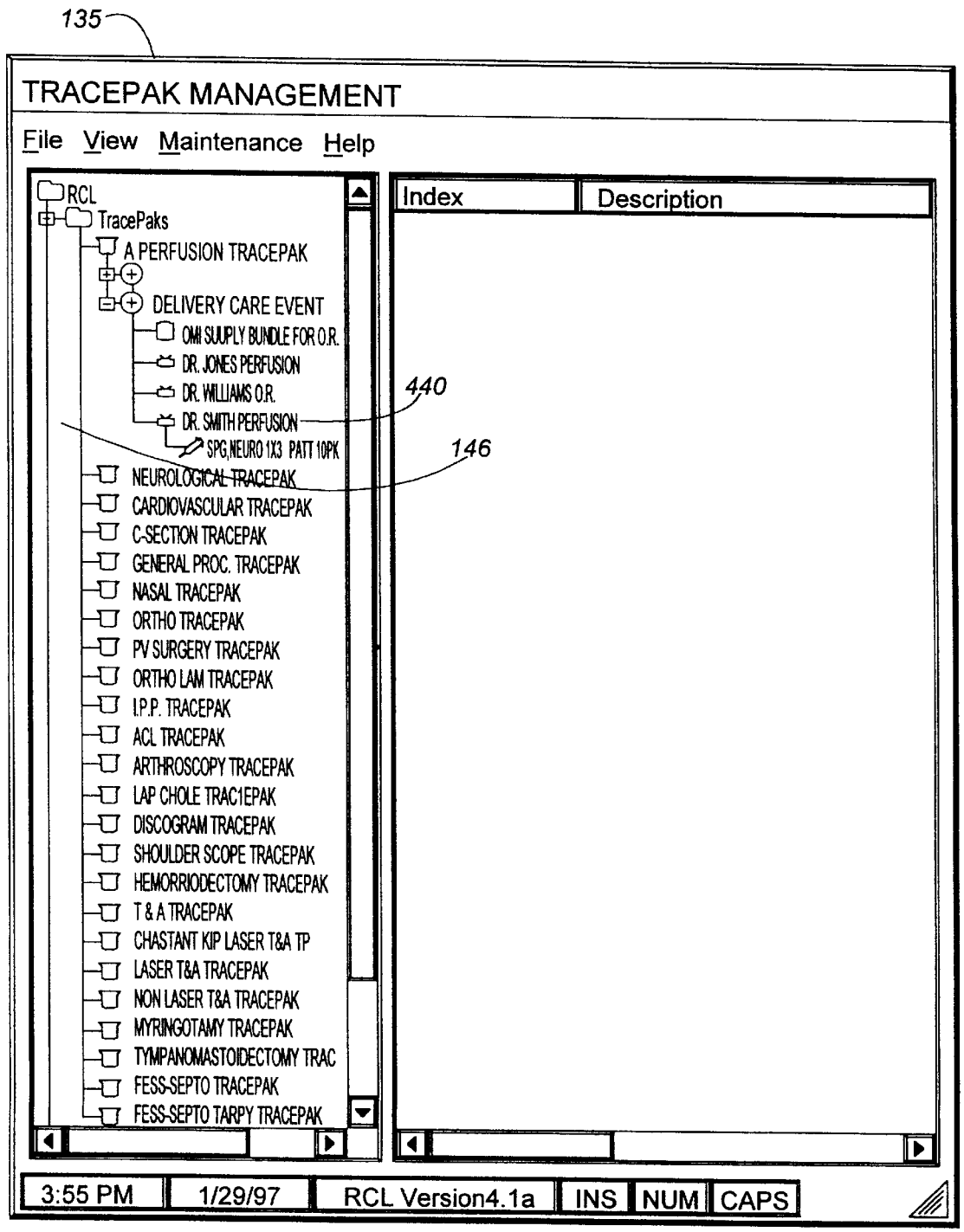
Figure 26:
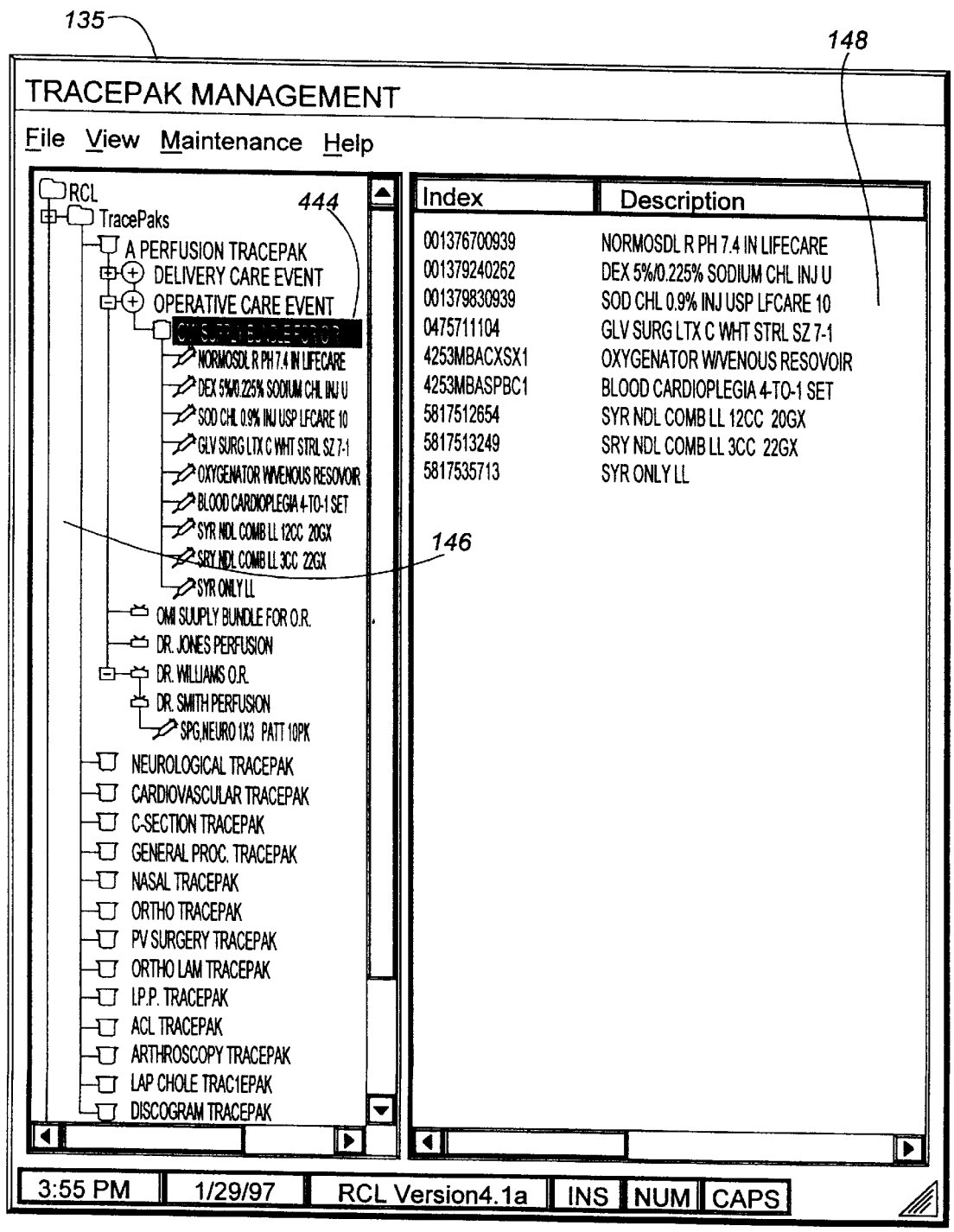

Referring now to FIG. 25, once the new part has been added in the Bundle Maintenance screen, it appears as an item under that Bundle in the tree view 146 of the Trace-Pak™ Management Screen 135. As is shown in FIG. 25, the Dr. Smith Perfusion bundle 440 now shows a new part 442 as being a component of that bundle. Referring now to FIG. 26, the contents of any supply bundle may be seen by clicking on that bundle's icon. In FIG. 26, the OMI Supply Bundle For OR 444 has been highlighted in the tree view 146. This action serves to expand the bundle and show its components in the tree view 146 as well as show a more detailed listing of components in the list display 148. This feature allows the user to view components of procedures at varying levels of detail, depending on the information required.

Query Procedure

Figure 27:
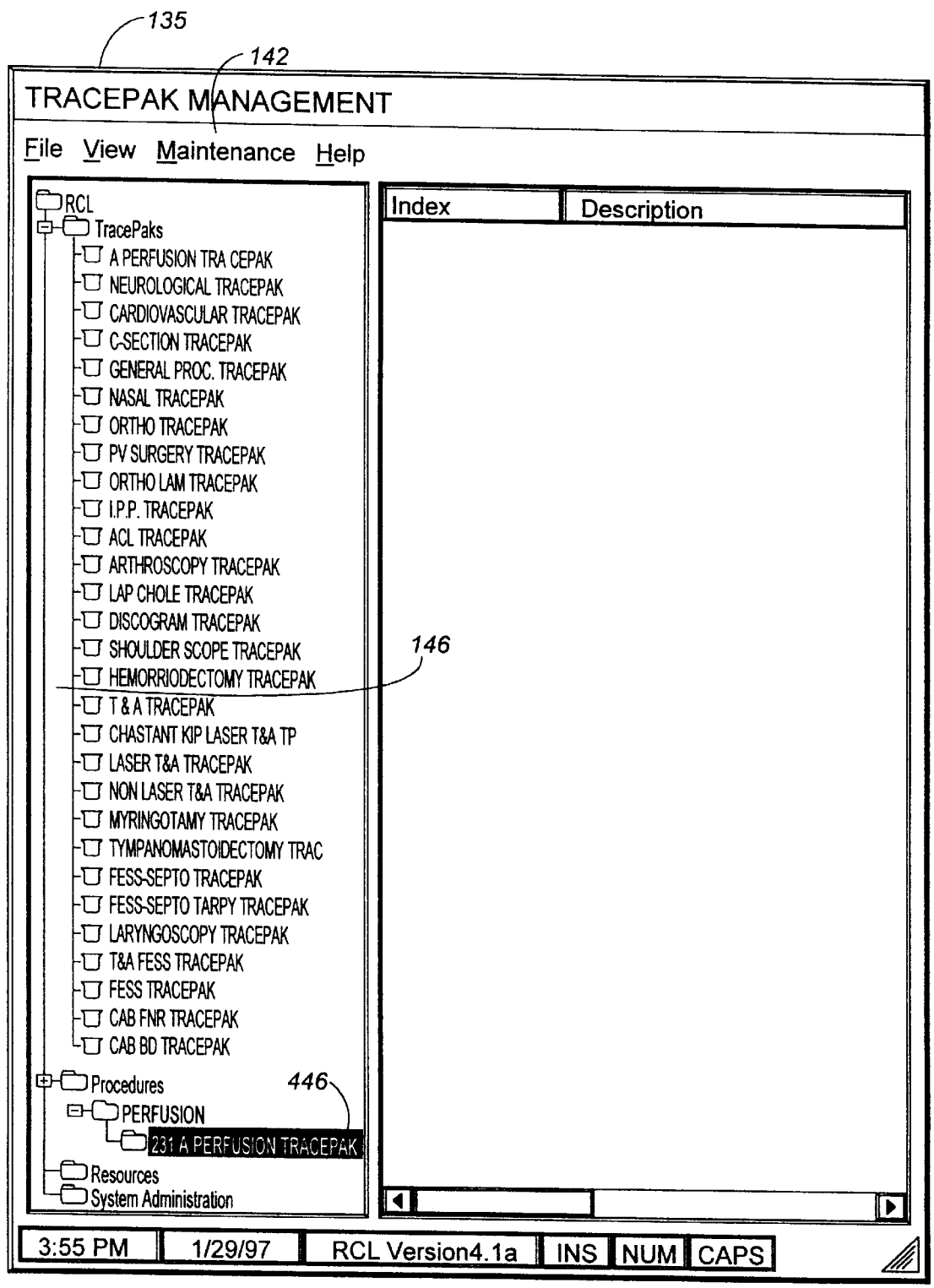
FIGS. 27–32 depict screen shots showing the searching, editing and completion of procedures in the example.
Figure 28:
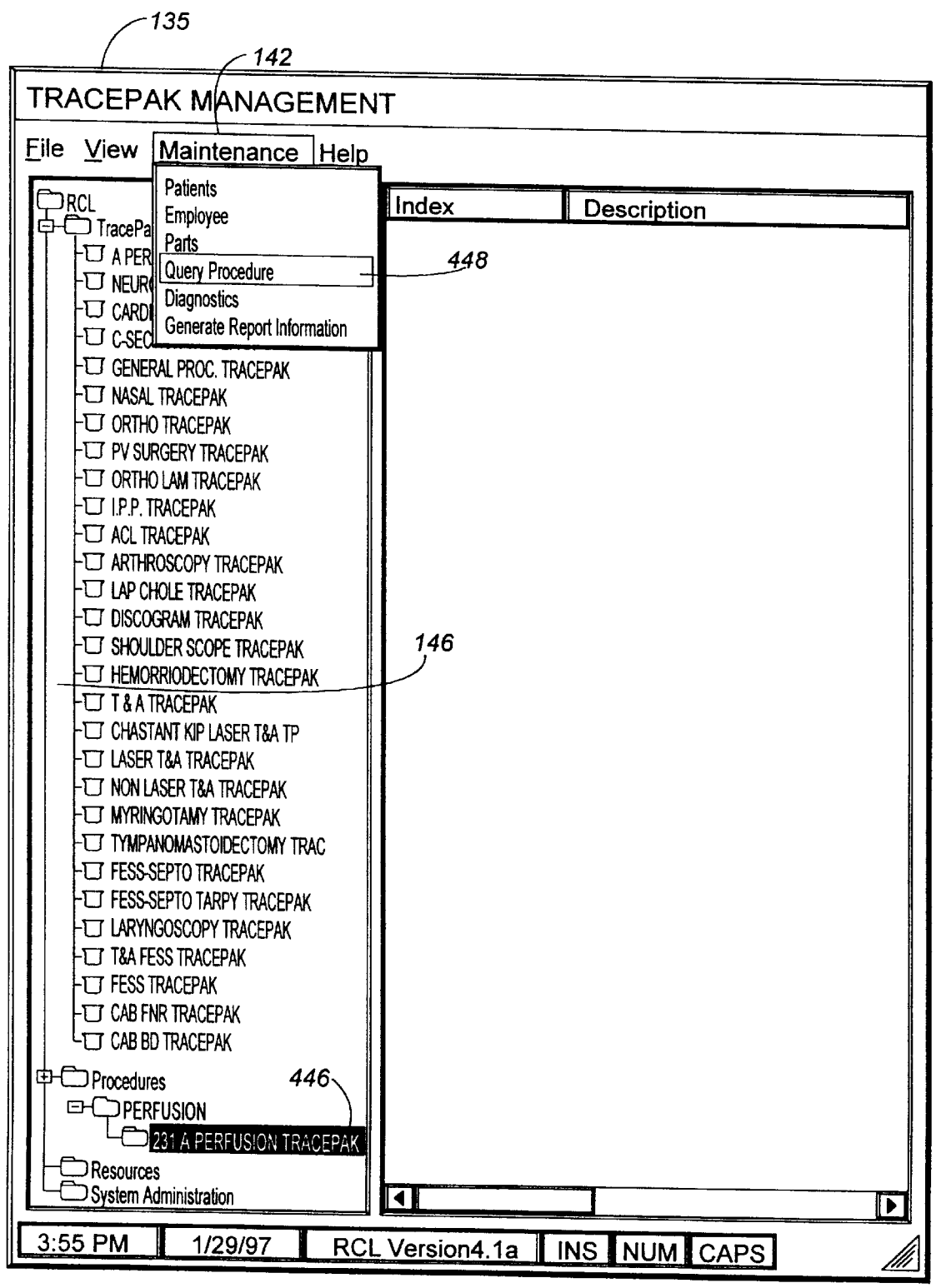

As with patients, employees, bundles and parts, the RCL™ software of the example allows for the maintenance of procedural templates and stored historical information of completed procedures. To perform procedure maintenance, the desired procedure, such as a Perfusion TracePak™ 446, shown in FIG. 27, is highlighted by selection with the cursor in the TracePak™ Management Screen 135. Once the desired procedure is highlighted (446), the user selects the Maintenance drop down menu 142 and selects the Query Procedure function 448 from that menu 142 as shown in FIG. 28.

Figure 29:
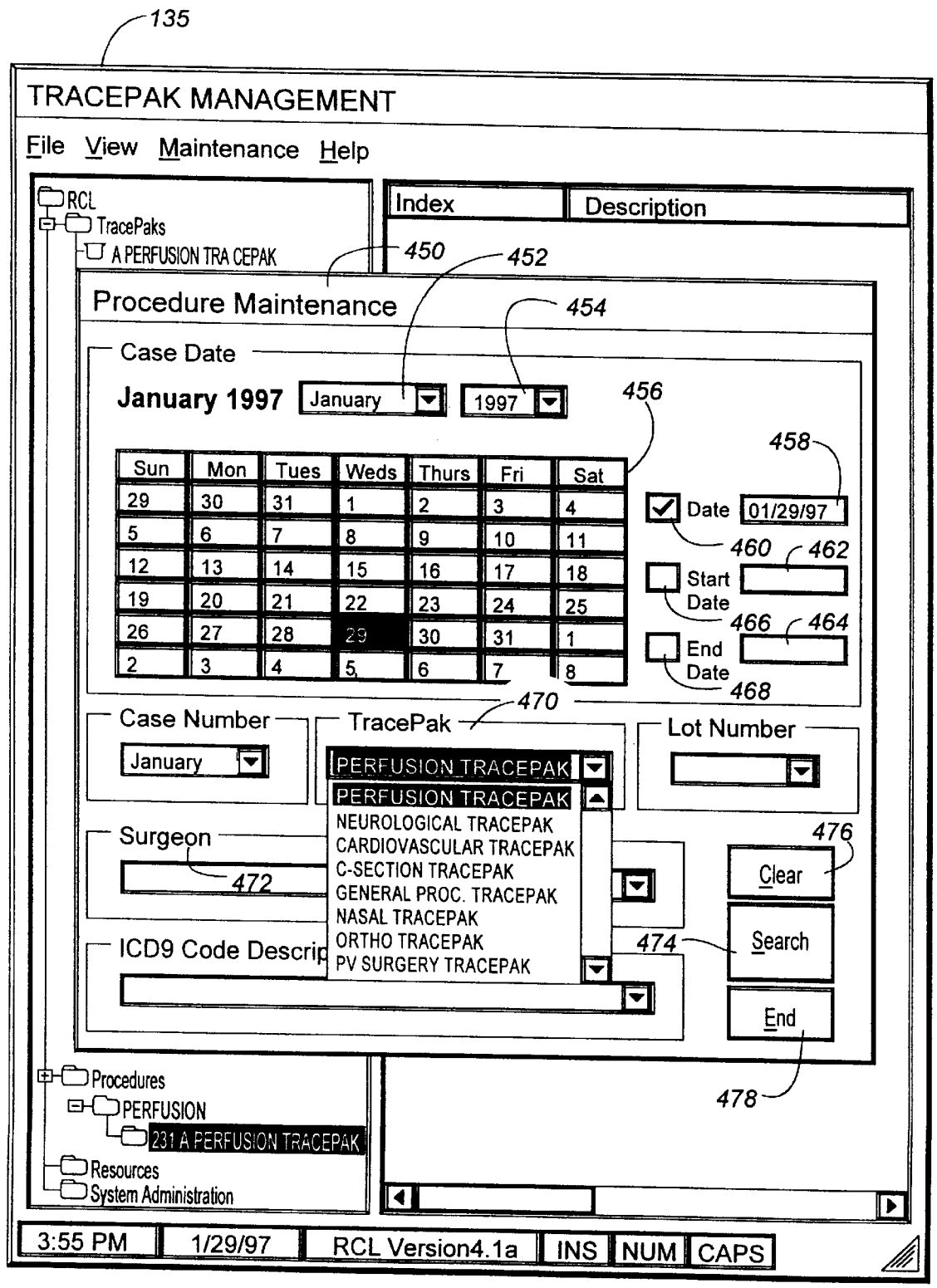
Figure 30:
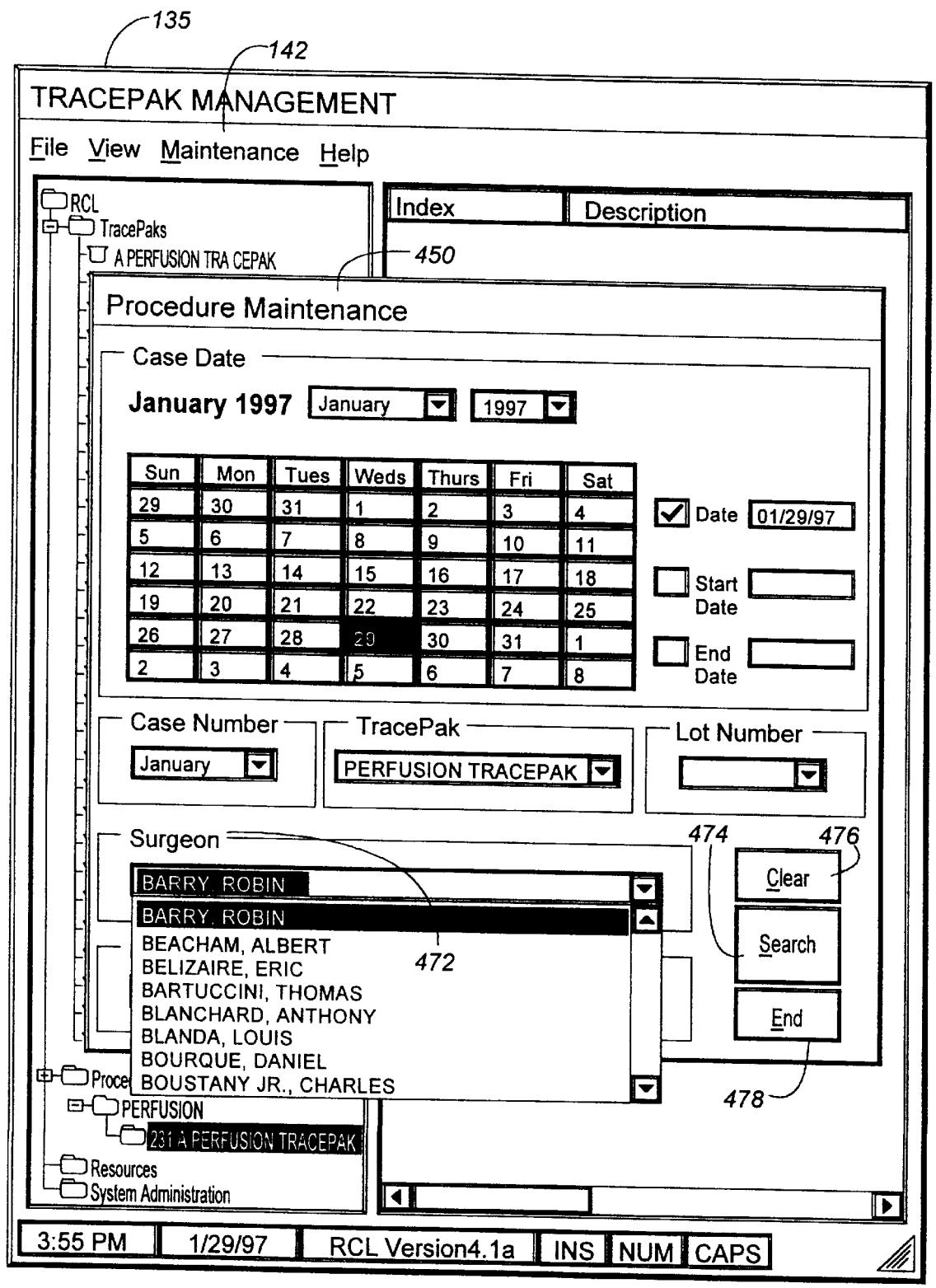

Referring now to FIG. 29, selection of the Query Procedure function 448 calls the Procedure Maintenance screen 450 which assists the user in finding the procedure history for which maintenance is to be performed. The user may use the date fields 452 and 454 to select the month and day of the procedure and may select the exact date using the calendar 456 provided. By completing the Date field 458 and checking the date box 460 the user may restrict the search to procedures performed on an exact date. If only a range of dates is known, the user may enter the beginning date in the start date field 462 and the ending date in the end date field 464 and check the appropriate start date 466 and end date 468 boxes. Alternatively, if only a start date is known or only an end date is known, the procedures may be searched with the single criterion. The Procedure Maintenance Screen 450 also allows the search to be narrowed by the type of procedure (in this example shown in the TracePak™ field 470, which provides the user with a selection of all of the procedural templates which have been configured for the particular hospital). Also, as shown in FIG. 30, the search can be limited to specific surgeons by selection of the appropriate surgeon from the Surgeon field 472. The list of surgeons preferably includes all of the surgeons that have been configured in the employee maintenance function described previously.

Once the appropriate search criteria have been entered, the user then executes the search for the procedure(s) by selecting the search function 474. If the criteria were entered improperly, or if another search is to be conducted, the user selects the Clear function 476 to empty all of the search criteria from the respective fields. If the procedure maintenance was completed, the user can end the session by selecting the End function 478.

Figure 31:
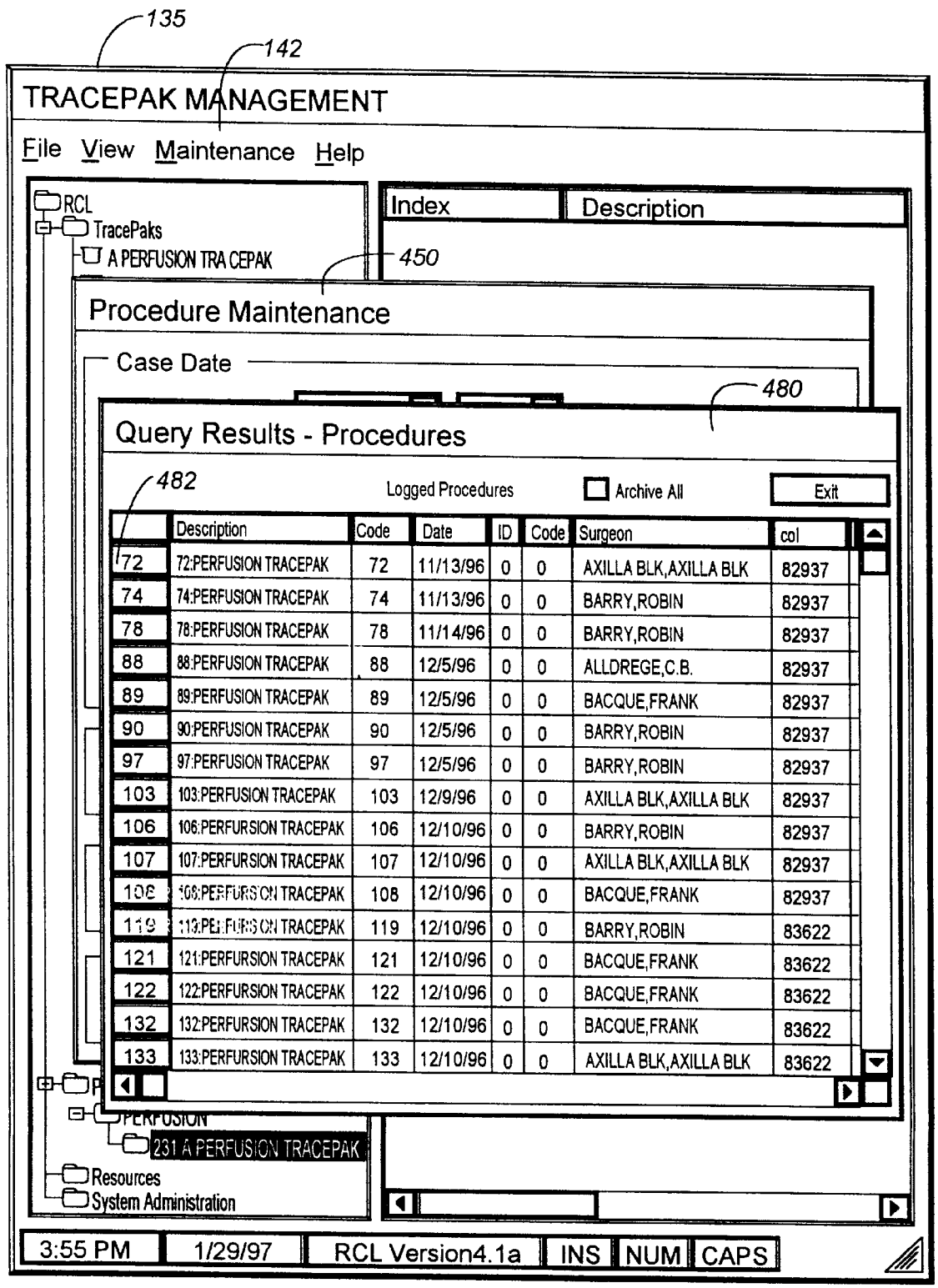
Figure 32:
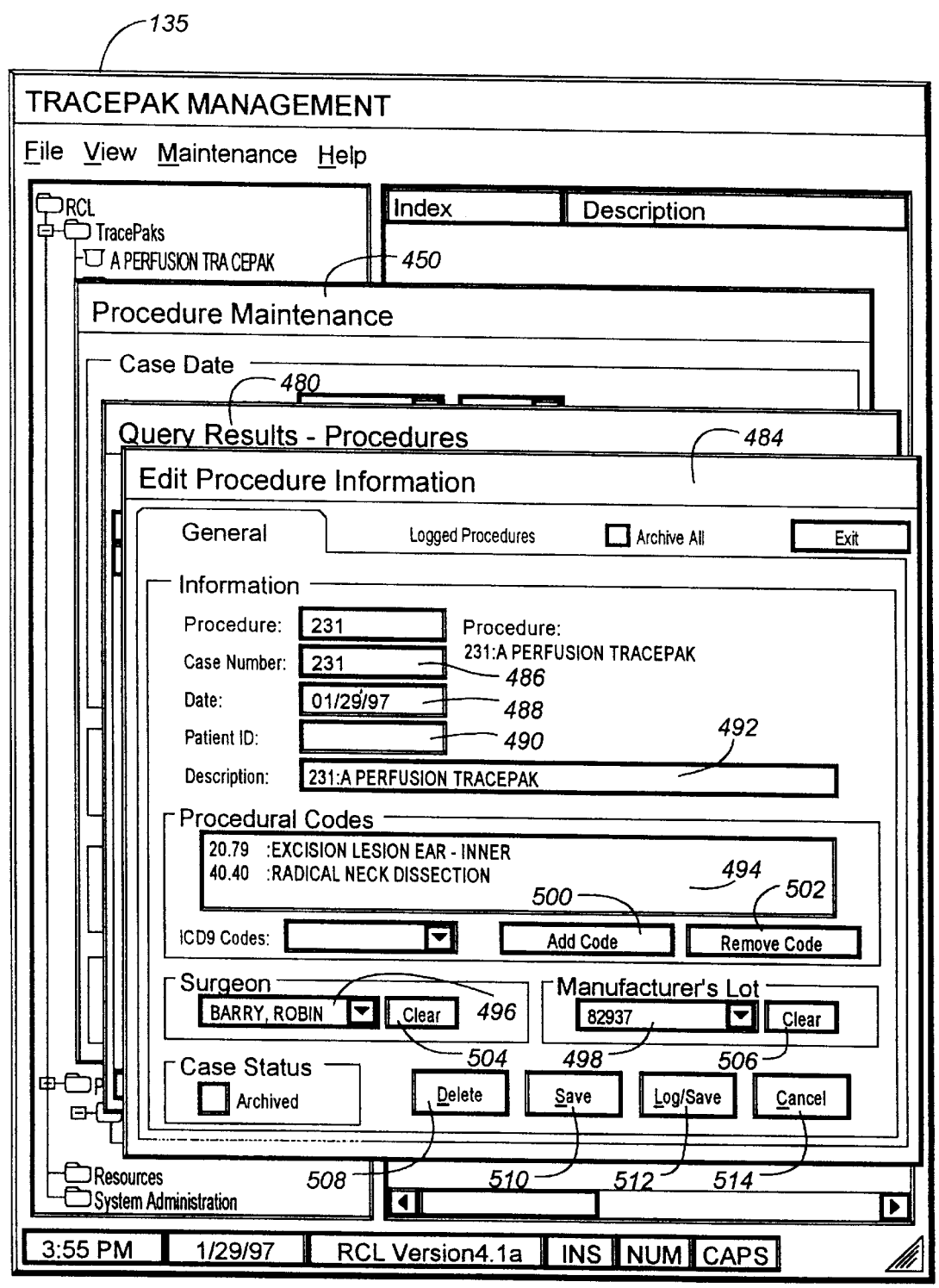

Once the search has been executed, a Query Results screen 480 appears as shown in FIG. 31. This screen 480 shows a list of procedures meeting the search criteria. From this list, the user selects the desired procedure for maintenance, in the example, Perfusion procedure number 72 482, such as by pointing to a particular procedure and double clicking with the left mouse button. This action calls the Edit Procedure Information Screen 484, as shown in FIG. 32. This screen 489 has fields 486, 488, 490, 492, 494, 496, and 498 for the procedure specific information which may be changed by the user. In the Procedural Codes field 494 the user may add a new code by selecting the Add Code 500 function or may remove a code by selecting the Remove Code 502 function. The user may select a new surgeon in the Surgeon field or may clear the current surgeon by selecting the Clear 504 function. Similarly, in the Manufacturer's Lot field 498, the user may clear the field by selecting the Clear 506 function or may enter a new lot number.

Also, the user may Delete 508 the procedure, Save 510 the edited procedure, may access the logging file (where component usage was stored) with the Log/Save 512 function, or Cancel 514 the editing by selecting the appropriate function button.

Database Organization

The structure, organization and relationships between objects for the database structure are outlined in Tables I–XVI. Tables I–XVI contain the tree structure of the database, the registration and other tables, the definition of objects and the schema.

TABLE I

Function: Designation of object types.

| Column | Type | Description |
| --- | --- | --- |
| type_serial | Integar | Unique serial identification number. |
| type_class | char (64) | Object type description. |
| type_ocxid | Text | Object type system application. |
| type_class_serial | Integar | Object type category identification number. |
| type_serial | unique index | type_serial |

TABLE II

OBJECT CATEGORY MASTER FILE
Table: sys_class
Function: Designation of object type categories.

| Column | Type | Description |
| --- | --- | --- |
| class_serial | Integer | Unique serial identification number. |
| class_description | char (30) | Object type category description. |
| class_serial | unique index | class_serial |

TABLE III

DATABASE TABLE MASTER FILE
Table: sys_file
Function: Designation of object database tables.

| Column | Type | Description |
| --- | --- | --- |
| file_serial | Serial | Unique serial identification number. |
| file_table | char (30) | SQL Server database table name. |
| file_index | char (30) | SQL Server database index name. |
| file_identity | Integer | Maximum key index serial number. |
| File_serial | unique index | file_serial |
| file_table | unique index | file_table |

TABLE IV

OBJECT TREE MASTER FILE
Table: sys_tree
Function: Designation of resource object hierarchy.

| Column | Type | Description |
| --- | --- | --- |
| tree_serial | integer | Unique serial identification number. |
| tree_handle | integer | Serial identification number of case. |
| tree_parent | integer | Serial identification number of container. |
| tree_object | integer | Serial identification number of resource object. |
| tree_number | float | Resource object sequence number. |
| tree_origin | char (1) | Resource object data entry origin: (I)nternal/(E)xternal. |
| tree_schedule | float | Resource object quantity scheduled. |
| tree_issue | float | Resource object quantity issued. |
| tree_consume | float | Resource object quantity consumed. |
| tree_scrap | float | Resource object quantity scrapped. |
| tree_return | float | Resource object quantity returned. |
| tree_created_by | char (20) | System user name record created by. |
| tree_modified_by | char (20) | System user name record modified by. |
| tree_created_date | datetime | Date record created. |
| tree_modified_date | datetime | Date record modified. |
| tree_serial | unique index | tree_serial |
| tree_unique_key | unique index | tree_handle, tree_parent, tree_object, tree_number |

TABLE V

OBJECT TREE RESOURCE COST FILE
Table: sys_cost
Function: Designation of resource object cost.

| Column | Type | Description |
| --- | --- | --- |
| cost_serial | integer | Unique serial identification number. |
| cost_object | integer | Serial identification of resource object. |
| cost_active_date | datetime | Resource object active date. |
| cost_inactive_date | datetime | Resource object inactive date. |
| cost_price | float | Resource object cost. |
| cost_serial | unique index | cost_serial |

TABLE VI

OBJECT ATTRIBUTE MASTER FILE
Table: att_master
Function: Designation of object attributes.

| Column | Type | Description |
|---|---|---|
| attr_serial | integer | Unique serial identification number. |
| attr_mnemonic | char (10) | Attribute mnemonic. |
| attr_description | char (50) | Attribute description. |
| attr_type_serial | integer | Serial identification number of attribute type. |
| attr_serial | unique index | attr_serial |

TABLE VII

OBJECT ATTRIBUTE TYPE MASTER FILE
Table: att_type
Function: Designation of object attribute types.

| Column | Type | Description |
|---|---|---|
| attp_serial | integer | Unique serial identification number. |
| attp_description | char (30) | Attribute description. |
| attp_serial | unique index | attp_serial |

TABLE VIII

OBJECT ATTRIBUTE CROSS REFERENCE FILE
Table: sys_xref
Function: Designation of object attribute correlation.

| Column | Type | Description |
|---|---|---|
| xref_node_serial | integer | Unique serial identification number. |
| xref_attr_serial | integer | Serial identification of resource attribute. |
| xref_node_serial | unique index | xref_node_serial |

TABLE IX

OBJECT MEMO TEXT FILE
Table: sys_text
Function: Designation of resource object documentation.

| Column | Type | Description |
|---|---|---|
| text_serial | integer | Unique serial identification number. |
| text_id | integer | Serial identification of resource object. |

TABLE IX-continued

OBJECT MEMO TEXT FILE
Table: sys_text
Function: Designation of resource object documentation.

| Column | Type | Description |
|---|---|---|
| text_type | char (1) | Object type identification: (N) sys_node/ (T) sys_tree |
| text_comment | text | Object text. |
| text_serial | unique index | text_serial |

TABLE X

OBJECT RESOURCE DATA FILE
Table: sys_resource
Function: Designation of resource object data.

| Column | Type | Description |
|---|---|---|
| resc_node_serial | integer | Unique serial identification number. |
| resc_cost_gl | float | Resource object gl cost. |
| resc_charge_gl | float | Resource object gl charge. |
| resc_cost | float | Resource object cost. |
| resc_charge | float | Resource object charge. |
| resc_uoi | char (2) | Resource object unit of issue. |
| resc_capacity | float | Resource object capacity. |
| resc_sch_type | char (1) | Resource object scheduled type. |
| resc_pin_type | char (1) | Resource object plan type. |
| resc_lead_time | datetime | Resource object lead time. |
| resc_node_serial | unique index | Resc_node_serial |

TABLE XI

OBJECT RESOURCE TIMES FILE
Table: sys_time
Function: Designation of resource object times.

| Column | Type | Description |
|---|---|---|
| time_tree_serial | integer | Unique serial identification number. |
| time_sch_start | datetime | Resource scheduled start time. |
| time_sch_stop | datetime | Resource scheduled stop time. |
| time_plan_start | datetime | Resource planned start time. |
| time_plan_stop | datetime | Resource planned stop time. |
| time_actual_start | datetime | Resource actual start time. |
| time_actual_stop | datetime | Resource actual stop time. |
| time_offset | datetime | Resource offset time. |
| time_duration | datetime | Resource duration time. |
| time_tree_serial | unique index | time_tree_serial |

TABLE XII

| sys_tree | sys_node | sys_xref | att_master | att_type |
|---|---|---|---|---|
| tree_serial | | | | |
| tree_handle | | | | |
| tree_parent | | | | |
| tree_object | node_serial | xref_node_serial | | |
| tree_number | node_sys_type | xref_attr_serial | attr_serial | |
| tree_origin | node_sys_file | | attr_mnemonic | |
| tree_schedule | node_key | | attr_description | |
| tree_issue | node_mnemonic | | attr_attp_serial | attp_serial |
| tree_consume | node_description | | | attp_mnemonic |
| tree_scrap | | | | attp_description |
| tree_return | | | | |

TABLE XIII

TEMPLATE CONFIGURATION

| | |
|---|---|
| 90-1001 | CardioVascular TracePak |
| 91-ANES1001 | CV-Anesthesia Care Event |
| 92-DER1001ANES | CV-Anesthesia DeRoyal Supply Bundle |
| 50-1001 | CV-Surgical Pack |
| 5-1001 | Catheter, Foley Temperature Probe |
| 92-DLR1001ANES | CV-Anesthesia Distributor Supply Bundle |
| 92-HOS1001ANES | CV-Anesthesia Hospital Supply Bundle |
| 91-OPER1001 | CV-Operative Care Event |
| 92-DER1001OPER | CV-Operative DeRoyal Supply Bundle |
| 50-1001 | CV-Surgical Pack |
| 5-1001 | Foley Temperature Probe Catheter |
| 92-DLR1001OPER | CV-Operative Distributor Supply Bundle |
| 92-HOS1001OPER | CV-Operative Hospital Supply Bundle |

TABLE XIV

SYS_NODE REGISTRY

| node_serial | Node_key | node_mnemonic | node_description |
|---|---|---|---|
| 10 | 1 | 90-1001 | CardioVascular TracePak |
| 20 | 2 | 91-ANES1001 | CV-Anesthesia Care Event |
| 30 | 3 | 91-OPER1001 | CV-Operative Care Event |
| 40 | 4 | 92-DER1001ANES | CV-Anesthesia DeRoyal Supply Bundle |
| 50 | 5 | 92-DLR1001ANES | CV-Anesthesia Distributor Supply Bundle |
| 60 | 6 | 92-HOS1001ANES | CV-Anesthesia Hospital Supply Bundle |
| 70 | 7 | 92-DER1001OPER | CV-Operative DeRoyal Supply Bundle |
| 80 | 8 | 92-DLR1001OPER | CV-Operative Distributor Supply Bundle |
| 90 | 9 | 92-HOS1001OPER | CV-Operative Hospital Supply Bundle |
| 100 | 10 | 50-1001 | CV-Surgical Pack |
| 110 | 11 | 5-1001 | Foley Temperature Probe Catheter |
| 120 | 12 | 1001 | Surgical Case Identification Number |

TABLE XV

Sys_TREE CARD

| tree_serial | tree_handle | tree_parent | tree_object | tree_number |
|---|---|---|---|---|
| 1001 | 0 | CARD | 10 | 1 |
| 1002 | 0 | 10 | 20 | 1 |
| 1003 | 0 | 20 | 40 | 1 |
| 1004 | 0 | 40 | 100 | 1 |
| 1005 | 0 | 100 | 110 | 1 |
| 1006 | 0 | 20 | 50 | 1 |
| 1007 | 0 | 20 | 60 | 1 |
| 1008 | 0 | 10 | 30 | 1 |
| 1009 | 0 | 30 | 70 | 1 |
| 1010 | 0 | 70 | 100 | 1 |
| 1011 | 0 | 100 | 110 | 1 |
| 1012 | 0 | 30 | 80 | 1 |
| 1013 | 0 | 30 | 90 | 1 |

TABLE XVI

SYS_TREE CASE

| tree_serial | tree_handle | Tree_parent | tree_object | tree_number |
|---|---|---|---|---|
| 2001 | 120 | CASE | 120 | 1 |
| 2002 | 120 | 2001 | 20 | 1 |
| 2003 | 120 | 2002 | 40 | 1 |
| 2004 | 120 | 2003 | 100 | 1 |
| 2005 | 120 | 2004 | 110 | 1 |
| 2006 | 120 | 2002 | 50 | 1 |
| 2007 | 120 | 2002 | 60 | 1 |
| 2008 | 120 | 2001 | 30 | 1 |
| 2009 | 120 | 2008 | 70 | 1 |
| 2010 | 120 | 2009 | 100 | 1 |
| 2011 | 120 | 2010 | 110 | 1 |
| 2012 | 120 | 2008 | 80 | 1 |
| 2013 | 120 | 2008 | 90 | 1 |

Selection Criteria
if (tree_handle)
    select from sys_tree where tree_object=node_serial and node_sys_type=type_serial and tree_parent=? and tree_handle=?
else
    select from sys_tree where tree_object=node_serial and node_sys_type=type_serial and tree_parent=? and (tree_handle=? or tree_handle=tree_object)

Sys_Node Registration

Sys_node is the main resource master table. Every resource that could be used in way is registered once and only once in sys_node (labor, supplies, equipment). All organizational nodes are also registered in sys_node (care events, templates, resource bundles). Tree_object is the main field in sys_tree. This field always corresponds with a sys_node record. The tree_parent record corresponds with a sys_node record if in a Template Pathway. However, it corresponds with a tree location (tree_serial) if in a specific case. To find out information about a node, the sys_node table links with the sys_type table that has information about the type and where the master file data resides.

Sys_Tree

Sys_tree is the database table that holds the structure of the Bill of Resources. The tree_number fields allows for sequencing of resources in the pathway. Tree_serial is the serial number of the record, Tree_handle indicates whether it is a specific case or in the Templates. Tree_parent is either the sys_node registration number of the containing object or the location to this record in sys_tree, and tree_object is the object in question always.

Reusable Components

A tray is a recursive table that enables reusable components. For example if a tray "50-1234" is used in more than one procedure, the tray has unlimited reusability. One record can be added to each procedure that uses the Tray. The record is where the tree_parent is equal to the container of the tray and the tree_object is the tray. From this point down all references are looking at literally the same records. Therefore, if a change is made inside the tray, it is reflected in all cases that used the tray without any behind the scenes processing to allow this to happen.

Unique Components

In order to enable logging specific cases there needs to be the ability to make a change in a case that is not reflected in all other references to a given tray. To accommodate this, the invention uses a field called tree_handle. The tree_handle is always ZERO when dealing with a BOR, however it is always non-zero when dealing with a specific case. This results in a unique copy of the entire pathway so if a line is added, deleted, or modified, it will only be reflected in this group of records with a common handle. The start of a Case is where the tree_handle is equal to the tree_object. Also, to accommodate proper traversing of the tree, the serial number of sys_tree is used for the tree_parent field as opposed to the sys_node registration number as is done in a template. This is needed in the case of the same tray being used in two different locations in the same Case. Different data may be logged for the same tray in the anesthesia care event than in the operative care event.

This system allows the use of one table to accommodate both template configuration and case logging. Therefore, the same programmatic functions can be used to traverse and log data for both scenarios.

The foregoing description of the preferred embodiments, and in particular the Example, are for the purposes of illustration and not limitation. The basic functions and methods set out in the following claims could be implemented in a variety of different ways using a variety of different techniques. For example, although use of computer technology is the preferred manner for implementing the invention, it could be implemented in a variety of other ways, including manually. Also, while the Example describes a particular software structure which implements the invention, the invention could be implemented using different types of hardware, operating systems, programming languages, database programs, etc. by one of ordinary skill in the art. Throughout the claims, the terms supply and/or resource are used to refer to items "used" during a medical procedure; it is within the scope of the present invention that the term supply and the term resource may be used interchangeably to refer to consumable medical supplies, reusable medical supplies, disposable medical supplies, disposable or reusable items of equipment, labor resources, or any other item, resource, device, etc. utilized in the provision of medical care can be included within the definition of "supply" or "resource" as used herein and in the following claims. Such numerous modifications, additions, deletions, substitutions, etc., may be made by one of ordinary skill in the art without departing from the scope of the invention set forth in the following claims.

Further, while the preferred embodiment is described as being implemented in the Windows 95 or NT environment using ActiveX or OLE controls from Microsoft Corp., the modular software object approach described could be implemented in other standards or operating environments such as Delphi. Furthermore, while the objects described above are preferentially written in Visual C++, any other common programming language may be used as well. Finally, although the computer environment is preferentially a PC environment, either networked or stand-alone, other computer systems such as RISC servers, workstations, mainframes, or access to processors through the Internet may be substituted.

What is claimed is:

1. An information management system for tracking and analyzing information relating to medical supply usage on a procedural level in a clinical setting, the system comprising:

a general purpose computer system, including:

storage means for storing data corresponding to the information;

processing means for processing instructions relating to tracking and analyzing the information;

display means for presenting the information in a human perceptible format; and input means for receiving user input relating to tracking and analyzing the information;

information management software installed on the general purpose computer system, including:

node software objects, each of the node software objects providing a health-care information management function, including:

a clinical pathway node software object for selectively creating, managing, and maintaining user-defined, user-configurable clinical pathway module software objects adapted to function with the clinical pathway node software object and representing provider-specific procedural templates of the information relating to health care services procedures, the clinical pathway module software objects including:

resource software objects, corresponding to resources to be used in providing health care services, including:

a list of supplies predetermined to be preferred by a particular healthcare provider for use during a given medical procedure; and a recordation form for the given procedure based upon at least one of the provider-specific procedural templates for the given procedure, the recordation form including at least a partial listing of the supplies predetermined to be preferred by a particular healthcare provider for use during the given procedure based upon the at least one provider-specific procedural template, the recordation form including a scheduled amount of each of the supplies included in the at least one provider-specific procedural template to be used during the given medical procedure; and container software objects for containing software objects having at least one common characteristic;

a case management node software object for selectively creating, managing, and maintaining a user-defined, user-configurable case management module software object adapted to function with the case management node software object from the clinical pathway module software object, the case management module software object representing a selected clinical pathway module software object as modified to reflect a prospective patient-specific case, and containing patient-specific information, and adapted to receive additional patient-specific information; and a resource utilization tracking node software object for selectively creating, managing, and maintaining at least one user-defined, user-configurable model module software object adapted to function with the resource utilization tracking node software object and the case management module software object, the model module software object representing the case management module software object as modified by at least the patient-specific information to reflect a historical patient-specific case by recording on the recordation form actual usage information reflecting actual usage of supplies during the given procedure, the recording including:

recording an issued amount of each of the supplies included in the at least one provider-specific procedural template, where the issued amount is an amount issued for use in the given procedure;

recording a consumed amount of each of the supplies included in the at least one provider-specific procedural template, where the consumed amount is an amount actually consumed during the given procedure;

recording a returned amount of each of the supplies included in the at least one provider-specific procedural template, where the returned amount is an amount returned to storage after the given procedure; and recording a scrapped amount of each of the supplies included in the at least one provider-specific procedural template, where the scrapped amount is an amount disposed of but not consumed during the given procedure nor returned to storage;

the resource utilization tracking node software object further for selectively creating, managing, and maintaining a user-defined, user-configurable utilization study module software object from the at least one model module software object; and the resource utilization tracking node software object further for analyzing the utilization study module software object to determine supply request and actual usage patterns on a procedural level over a given time period for the particular healthcare provider by comparing the issued, consumed, returned, and scrapped amounts, and modifying the provider-specific procedural template to more fully conform to the actual usage patterns based on the analyzing.

2. The system of claim 1 wherein the container software objects comprise a plurality of container software object types, each type providing a specific container software object functionality.

3. The system of claim 1 wherein the container software objects comprise:

a user-configurable care event container software object representing a specific health care services care event, the care event container software object functional to contain container software objects and resource software objects related to the specific health care services care event represented by the care event container software object; and a user-configurable bundle container software object functional to contain resource software objects corresponding to specific related health care resources which would be provided in a group or bundle.

4. The system of claim 1 further comprising data software objects selectively associated with a software object selected from the group consisting of the clinical pathway module software object, the case management module software object, and the container software object, the data software objects suitable for collecting and maintaining information related to the software object with which the data software object is selectively associated.

5. The system of claim 1 further comprising a library node software object for selectively creating, collecting, and organizing reusable, user-defined, user-configurable container software objects and resource software objects for use in the clinical pathway node software object and the case management node software object.

6. An information management system for tracking and analyzing information relating to medical supply usage on a procedural level in a clinical setting, the system comprising:

a general purpose computer system, including:

storage means for storing data corresponding to the information;

processing means for processing instructions relating to tracking and analyzing the information;

display means for presenting the information in a human perceptible format; and input means for receiving user input relating to tracking and analyzing the information;

information management software installed on the general purpose computer system, including:

node software objects, each of the node software objects providing a health-care information management function, including:

a clinical pathway node software object for selectively creating, managing, and maintaining user-defined, user-configurable clinical pathway module software objects adapted to function with the clinical pathway node software object and representing provider-specific procedural templates of the information relating to health care services procedures, the clinical pathway module software objects including:

resource software objects, corresponding to resources to be used in providing health care services, including:

a list of supplies predetermined to be preferred by a particular healthcare provider for use during a given medical procedure; and a recordation form for the given procedure based upon at least one of the provider-specific procedural templates for the given procedure, the recordation form including at least a partial listing of the supplies predetermined to be preferred by a particular healthcare provider for use during the given procedure based upon the at least one provider-specific procedural template, the recordation form including a scheduled amount of each of the supplies included in the at least one provider-specific procedural template to be used during the given medical procedure; and container software objects for containing software objects having at least one common characteristic, wherein the container software objects comprise a plurality of container software object types, each type providing a specific container software object functionality, the container software objects including:

a user-configurable care event container software object representing a specific health care services care event, the care event container software object functional to contain container software objects and resource software objects related to the specific health care services care event represented by the care event container software object; and a user-configurable bundle container software object functional to contain resource software objects corresponding to specific related health care resources which would be provided in a group or bundle;

a case management node software object for selectively creating, managing, and maintaining a user-defined, user-configurable case management module software object adapted to function with the case management node software object from the clinical pathway module software object, the case management module software object representing a selected clinical pathway module software object as modified to reflect a prospective patient-specific case, and containing patient-specific information, and adapted to receive additional patient-specific information;

data software objects selectively associated with a software object selected from the group consisting of the clinical pathway module software object, the case management module software object, and the container software object, the data software objects suitable for collecting and maintaining information related to the software object with which the data software object is selectively associated;

a resource utilization tracking node software object for selectively creating, managing, and maintaining at least one user-defined, user-configurable model module software object adapted to function with the resource utilization tracking node software object and the case management module software object, the model module software object representing the case management module software object as modified by at least the patient-specific information to reflect a historical patient-specific case by recording on the recordation form actual usage information reflecting actual usage of supplies during the given procedure, the recording including:

recording an issued amount of each of the supplies included in the at least one provider-specific procedural template, where the issued amount is an amount issued for use in the given procedure;

recording a consumed amount of each of the supplies included in the at least one provider-specific procedural template, where the consumed amount is an amount actually consumed during the given procedure;

recording a returned amount of each of the supplies included in the at least one provider-specific procedural template, where the returned amount is an amount returned to storage after the given procedure; and recording a scrapped amount of each of the supplies included in the at least one provider-specific procedural template, where the scrapped amount is an amount disposed of but not consumed during the given procedure nor returned to storage;

the resource utilization tracking node software object further for selectively creating, managing, and maintaining a user-defined, user-configurable utilization study module software object from the at least one model module software object;

the resource utilization tracking node software object further for analyzing the utilization study module software object to determine supply request and actual usage patterns on a procedural level over a given time period for the particular healthcare provider by comparing the issued, consumed, returned, and scrapped amounts, and modifying the provider-specific procedural template to more fully conform to the actual usage patterns based on the analyzing; and a library node software object for selectively creating, collecting, and organizing reusable, user-defined, user-configurable container software objects and resource software objects for use in the clinical pathway node software object and the case management node software object.

* * * * *